United States Patent [19]
Palmer et al.

[11] Patent Number: 5,563,142
[45] Date of Patent: Oct. 8, 1996

[54] DIAROMATIC SUBSTITUTED COMPOUNDS AS ANTI-HIV-1 AGENTS

[75] Inventors: John R. Palmer; Donna L. Romero; Paul A. Aristoff; Richard C. Thomas; Herman W. Smith, all of Kalamazoo, Mich.

[73] Assignee: The Upjohn Company, Kalamazoo, Mich.

[21] Appl. No.: 198,428

[22] Filed: Feb. 22, 1994

Related U.S. Application Data

[60] Continuation of Ser. No. 57,041, Apr. 30, 1993, abandoned, which is a division of Ser. No. 904,247, Jun. 25, 1992, abandoned, which is a continuation-in-part of Ser. No. 603,838, Oct. 25, 1990, abandoned, which is a continuation-in-part of Ser. No. 457,483, Dec. 28, 1989, abandoned.

[51] Int. Cl.$^6$ ............... A61K 31/495; A61K 31/50; A61K 31/535; C07D 413/00; C07D 401/00; C07D 211/68

[52] U.S. Cl. ............... 514/253; 514/252; 514/318; 514/233.5; 514/233.8; 514/234.5; 514/235.2; 514/235.5; 514/235.8; 514/236.8; 514/237.2; 544/121; 544/129; 544/130; 544/124; 544/360; 544/362; 544/364; 546/193

[58] Field of Search .................... 544/364, 360; 514/253, 318; 546/193

[56] References Cited

U.S. PATENT DOCUMENTS

| | | | |
|---|---|---|---|
| 3,146,234 | 8/1964 | Archer | 260/268 |
| 3,188,313 | 6/1965 | Archer | 260/268 |
| 3,362,956 | 1/1968 | Archer | 260/268 |
| 3,472,854 | 10/1969 | Archer | 260/268 |
| 3,472,855 | 10/1969 | Archer | 260/268 |
| 3,491,098 | 1/1970 | Archer | 260/268 |
| 3,511,841 | 5/1970 | Archer | 268/268 |
| 3,562,278 | 2/1971 | Archer | 260/268 |
| 4,302,589 | 11/1981 | Fanshawe et al. | 546/201 |
| 4,613,598 | 9/1986 | Fukami et al. | 514/211 |
| 4,724,232 | 2/1988 | Rideout et al. | 514/50 |
| 4,728,650 | 3/1988 | Okayama et al. | 514/253 |
| 5,032,598 | 7/1991 | Baldwin et al. | 514/318 |
| 5,120,843 | 6/1992 | McCall et al. | 544/123 |
| 5,175,281 | 12/1992 | McCall et al. | 540/94 |
| 5,215,989 | 6/1993 | Baldwin et al. | 514/252 |

FOREIGN PATENT DOCUMENTS

| | | |
|---|---|---|
| 0154969 | 9/1985 | European Pat. Off. . |
| 345808 | 12/1989 | European Pat. Off. . |
| 370381A2 | 5/1990 | European Pat. Off. . |
| 01132579 | 11/1987 | Japan . |
| WO87/01706 | 3/1987 | WIPO . |
| WO88/08424 | 11/1988 | WIPO . |
| 9849 | 7/1991 | WIPO .................... 544/364 |

OTHER PUBLICATIONS

*Science*, 234, pp. 661–662 (1986).
*Science*, 229, pp. 1352–1357 (1985).
*Nature*, 343, pp. 470–474 (1990).
*Science*, 250, pp. 1411–1413 (1990).
*Indian J Med Res*, 63, pp. 1418–1425 (1975).
*Chemical Abstracts*, 100, p. 578, abstract 51549b (1984).
*Drug News & Perspectives*, 5(3) 153–169 (1992).
*AIDS Research and Human Retroviruses*, 8(6), 963–990 (1992).
VINITI, 3979–82 (1982).
*Indian J. Chem. Sect. B*, 17B(3), 246–9 (1979).

Primary Examiner—Cecilia Tsang
Attorney, Agent, or Firm—Bruce Stein

[57] ABSTRACT

The present invention includes diaromatic substituted heterocyclic compounds (III)

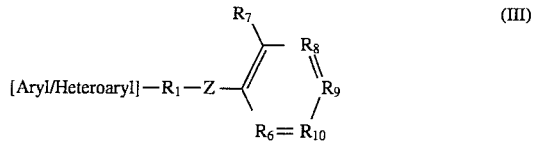

which are useful in treating individuals infected with the HIV virus.

11 Claims, No Drawings

DIAROMATIC SUBSTITUTED COMPOUNDS AS ANTI-HIV-1 AGENTS

CROSS REFERENCE TO RELATED APPLICATIONS

This application is continuation patent application of U.S. patent application Ser. No. 08/057,041, filed Apr. 30, 1993 now abandoned, which was a divisional patent application of U.S. patent application Ser. No. 07/904,247 filed Jun. 25, 1992 now abandoned which was the the continuing (national phase) application of PCT application PCT/US90/07390, filed Dec. 24, 1990, now WO91/09849, which is a continuation-in-part of U.S. Ser. No. 07/603,838, filed Oct. 25, 1990, now abandoned, which is a continuation-in-part of U.S. Ser. No. 07/457,483, filed Dec. 28, 1989, now abandoned.

BACKGROUND OF THE INVENTION

1. Field of the Invention

The diaromatic substituted compounds (III), the anti-AIDS piperazines (IV), the indoles (V) and the anti-AIDS amines (X) of the invention are useful in the treatment of individuals who are HIV positive whether or not they show AIDS symptoms at the present time.

2. Description of the Related Art

International Publication No. 87/01706, now U.S. Pat. No. 5,175,281, discloses compounds which can be visualized as steroid-piperazine-[substituted aromatic] or steroid-piperazine-[substituted heteroaromatic]. The steroid and piperazine being "connected" via the $C_{17}$ side-chain of the steroid.

International Publication No. WO 88/08424 disclosed compounds which can be visualized as

[trolox or indole]-connector-piperazine-[substituted aromatic]

[trolox or indole]-connector-piperazine-[substituted heteroaromatic]

in particular see the compounds of formula (III). None of those compounds were disclosed as having the utility set forth in this invention. In U.S. Pat. No. 5,120,843 it was disclosed that the compounds of formula (I) of International Publication No. WO 88/08424 were useful against AIDS. The anti-AIDS piperazines (IV) of the present invention are a few particular piperazines previously generically disclosed in International Publication No. WO 88/08424. The indoles compounds (V) of the present invention have been previously generically disclosed in International Publication No. WO 88/08424, see the bicyclic compounds of formula (III) therein.

U.S. Pat. No. 4,728,650 (Kuraray I) discloses hydroxytrolox compounds similar to the compounds of formula (III) of International Publication No. WO 88/08424. WO 87/05020 (Kuraray II) discloses additional compounds of the same type.

An estimated one to one and one-half million people in the United States are infected with a human retrovirus, the human immunodeficiency virus type I (HIV-1) which is the etiological agent of acquired immunodeficiency syndrome, AIDS, see Science, 661–662 (1986). Of those infected, an estimated two hundred and fifty thousands people will develop AIDS in the next five years, see Science, 1352–1357 (1985). On Mar. 20, 1987, the FDA approved the use of the compound, AZT (zidovudine), to treat AIDS patients with a recent initial episode of pneumocystis carinii pneumonia, AIDS patients with conditions other than pneumocystis carinii pneumonia or patients infected with the virus with an absolute CD4 lymphocyte count of less than $200/mm^3$ in the peripheral blood. AZT is a known inhibitor of viral reverse transcriptase, an enzyme necessary for human immunodeficiency virus replication.

U.S. Pat. No. 4,724,232 claims a method of treating humans having acquired immunodeficiency syndrome utilizing 3'-azido-3'-deoxy-thymidine (azidothymidine, AZT).

It is known in the art that certain antibiotics and polyanionic dyes inhibit retrovirus reverse transcriptase.

Many publications have reported the ability of various sulfated compounds to inhibit virus replication, including HIV.

Nature 343, 470 (1990) and Science 250, 1411 (1990) discloses potent benzodiazepin type reverse transcriptase inhibitors. The compounds of the present invention are not benzodiazepin type compounds.

Following the discovery of the anti-HIV activity of AZT, much effort has been focused on a wide variety of other dideoxynucleoside analogues in the search for superior agents. In the case of the 2',3'-dideoxy series, ddC and ddI have shown potent activity against HIV in vitro and have been evaluated in clinical trials, see *Drug News & Perspectives*, 5(3) 153–169 (1992) in particular page 160. The FDA has approved ddI for the treatment of HIV-1 infections in adults and pediatrics patients who are intolerant to, or whose health has significantly deteriorated while on, AZT treatment, see *AIDS research and Human Retroviruses*, 8(6), 963–990, (1992) in particular page 966.

U.S. Pat. Nos. 3,146,234 and 3,188,313 disclose compounds of the general formula

[substituted indol-2-yl]-$(CH_2)_n$-[piperazinyl type]-[aryl/heteroaryl]

The diaromatic substituted compounds (III) and the anti-AIDS piperazines (IV) of the present invention differ from the prior art compounds in that for the heteroaryl group they require substitution on the heteroaryl group and for the aryl group they require the substitution to be a group different than that of the groups in U.S. Pat. No. 3,188,313.

U.S. Pat. Nos. 3,472,855 and 3,562,278 disclose 3-indolinyl compounds which are useful as psychomotor depressants. The 2-indolinyl compounds of the present invention are useful for a totally different purpose, inhibition of HIV-RT and treatment of AIDS.

U.S. Pat. No. 3,362,956 discloses compounds of the general formula

[3-quinolyl]-$(CH_2)_n$-[piperazinyl type]-[pyridinyl/phenyl].

The diaromatic substituted compounds (III) of the present invention differ from the prior art compounds in that they do not include 3-quinolyl type compounds.

U.S. Pat. No. 3,472,854 discloses compounds of the general formula

[2-benzimidazolyl]-$(CH_2)_n$-[piperazinyl type]-[pyridinyl/phenyl].

The diaromatic substituted compounds (III) of the present invention differ from the prior art compounds in that they do not have a methylene linker, —$(CH_2)_n$-, when the heteroaryl group is 2-benzimidazolyl.

U.S. Pat. No. 3,491,098 discloses compounds of the general formula

[4(5)-imidazolyl]-$(CH_2)_n$-[piperazinyl type]-[pyridinyl/phenyl].

The diaromatic substituted compounds (III) of the present invention differ from the prior art compounds in that they require the substitution on —ϕ to be a group different than that of the group in the U.S. Pat. No. 3,491,098.

U.S. Pat. No. 3,511,841 discloses compounds of the general formula

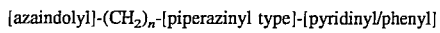

[azaindolyl]-(CH$_2$)$_n$-[piperazinyl type]-[pyridinyl/phenyl]

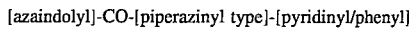

[azaindolyl]-CO-[piperazinyl type]-[pyridinyl/phenyl]

The diaromatic substituted compounds (III) of the present invention differ from the prior art compounds in that they require the substitution on —ϕ to be a group different than that of the group in U.S. Pat. No. 3,188,313.

U.S. Pat. No. 4,302,589 discloses 3-indolinyl compounds with a methyl group at the C$_2$ position of the indole and an ethyl bridge between the indole and piperazine which are useful as anti-psychotics. The 2-indolinyl compounds of the present invention are useful for a totally different purpose, inhibition of HIV-RT and treatment of AIDS.

European patent publication 345,808 discloses 3-indolinyl-piperazinyl-[substituted 2-pyridinyl] compounds (example 66) which are useful as anti-depressants. The 2-indolinyl compounds of the present invention are useful for a totally different purpose, inhibition of HIV-RT and treatment of AIDS.

There are a number of other chemically unrelated compounds which have been reported to inhibit HIV and/or be useful in the treatment of AIDS.

EP 0 154 969 and U.S. Pat. No. 4,613,598 disclose compounds of the formula

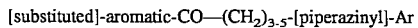

[substituted]-aromatic-CO—(CH$_2$)$_{3-5}$-[piperazinyl]-Ar

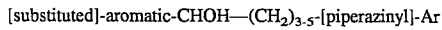

[substituted]-aromatic-CHOH—(CH$_2$)$_{3-5}$-[piperazinyl]-Ar where Ar is pyridinyl, —ϕ or substituted —ϕ which have the ability to lower blood pressure.

*VINITI*, 3979–82 (1982) in Russian and *Chem. Abst.* 100(7) 51549b (1984) discloses a compound which can be represented as 5-methoxy[indol-2-yl]-CO-piperazinyl-[2-quinolinyl] which differes from the claimed compounds in that none of the claimed compounds have quinoline structure or any bicyclic structure attached to the piperazinyl moiety.

JP 01132579 (1987) discloses compounds which can be represented as (optionally substituted)-[indol-2-yl]-CO-piperazinyl-(CH$_2$)$_n$-[pyridinyl] which have very strong blood platelet agglutination inhibiting activity where n is 1–5 which differs from the claimed compounds in that the claimed compounds do not permit any linking group between the piperazinyl moiety and the phenyl or pyridinyl substitutent.

*Indian J. Chem. Sect. B*, 17B(3), 246–9 (1979) and *Indian J. Med. Res.*, 63(10), 1418–25 (1975) disclose compounds which can be represented as

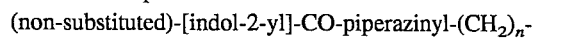

(non-substituted)-[indol-2-yl]-CO-piperazinyl-(CH$_2$)$_n$-[optionally substituted) phenyl] The *Indian J. Chem. Sect. B*, 17B(3), 246–9 (1979) reported on p. 247 that none of the compounds showed any noteworthy (CNS) biological activity. The *Indian J. Med. Res.*, 63(10), 1418–25 (1975) reported some of the compounds they prepared had anti-viral activity against Semliki forest virus (SFV) in mice. One compound, a dihydroisoquinolin was tested and found to be inactive against new castle disease virus in chick embryo. These compounds differ from the claimed compounds in that the claimed compounds require the indole group to be substituted and have a heteroaryl moiety (2-pyridinyl) attached directly to the piperazinyl substituent, not an aryl group (phenyl).

International Publication EP 370 381 A2, published 5 May 90 discloses compounds which can be represented as

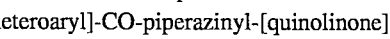

[heteroaryl]-CO-piperazinyl-[quinolinone]

where heteroaryl includes 2-indolyl which differ from the claimed compounds in that none of the claimed compounds have quinoline structure or any bicyclic structure attached to the piperazinyl moiety. The disclosed compounds possess cardiotonic and hypotensiv activities and the capability of reducing the heart rate.

U.S. Pat. Nos. 5,032,598 and 5,215,989 disclose anti-arrhythmic compounds of the formula

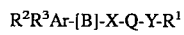

R$^2$R$^3$Ar-[B]-X-Q-Y-R$^1$ which if the appropriate substitutents were selected generically encompasses the diaromatic substituted compounds of formula (III), anti-AIDS piperazines (IV) and the indoles compounds (V) of the present invention.

SUMMARY OF INVENTION

Disclosed are diaromatic substituted compounds of formula (III)

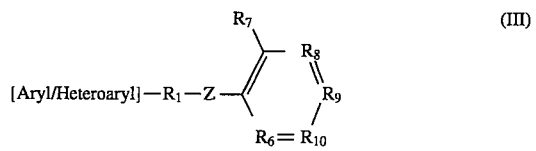

(III)

where R$_1$ is —CH$_2$—,
—CO—,
—CO—CH$_2$—,
—CH═CH—CO—;
where Z is

(Z-I)

where (I) R$_2$ is ═O or R$_{2-1}$:R$_{2-2}$ where one of R$_{2-1}$ and R$_{2-2}$ is —H and the other of R$_{2-1}$ and R$_{2-2}$ is —H or —CH$_3$, R$_3$ is ═O or R$_{3-1}$:R$_{3-2}$ where one of R$_{3-1}$ and R$_{3-2}$ is —H and the other of R$_{3-1}$ and R$_{3-2}$ is —H or —CH$_3$, R$_4$ is R$_{4-1}$:R$_{4-2}$ and R$_5$ is R$_{5-1}$:R$_{5-2}$ where one of R$_{4-1}$ and R$_{4-2}$ is —H and the other of R$_{4-1}$ and R$_{4-2}$ is —H or —CH$_3$, where one of R$_{5-1}$ and R$_{5-2}$ is —H and the other of R$_{5-1}$ and R$_{5-2}$ is —H or —CH$_3$, (II) R$_4$ is R$_{4-3}$:R$_{4-4}$ and R$_5$ is R$_{5-3}$:R$_{5-4}$ where one of R$_{4-3}$ and R$_{4-4}$ and one of R$_{5-3}$ and R$_{5-4}$ are taken together to form —CH$_2$— and the other of R$_{4-3}$ and R$_{4-4}$, and R$_{5-3}$ and R$_{5-4}$ are —H, R$_2$ and R$_3$ are —H:—H, (III) R$_2$ is R$_{2-5}$:R$_{2-6}$ and R$_5$ is R$_{5-5}$:R$_{5-6}$ where one of R$_{2-5}$ and R$_{2-6}$ and one of R$_{5-5}$ and R$_{5-6}$ are taken together to form —CH$_2$—CH$_2$—and the other of R$_{2-5}$ and R$_{2-6}$, and R$_{5-5}$ and R$_{5-6}$ are —H, and R$_3$ and R$_4$ are —H:—H, (IV) R$_3$ is R$_{3-5}$:R$_{3-6}$ and R$_4$ is R$_{4-5}$:R$_{5-6}$ where one of R$_{3-5}$ and R$_{3-6}$ and one of R$_{4-5}$ and R$_{4-6}$ are taken together to form —CH$_2$—CH$_2$— and the other of R$_{3-5}$ and R$_{3-6}$, and R$_{4-5}$ and R$_{4-6}$ are —H, and R$_2$ and R$_5$ are —H:—H, $$-Y_1-(CH_2)_{n11}-Z_2-(CH_2)_{n26}-Y_2- \quad \text{(Z-II)}$$

where $n_{11}$ is 1 thru 5, $n_{26}$ is 1 thru 5, $Y_1$ is —O—, —S—,
—N($Y_{1-1}$)— where $Y_{1-1}$ is $C_1$–$C_4$ alkyl,
—C($Y_{1-2}$)($Y_{1-3}$) where $Y_{1-2}$ and $Y_{1-3}$ are the same or different and are —H or $C_1$–$C_4$ alkyl, $Y_2$ is —O—, —S—,
—N($Y_{2-1}$)— where $Y_{2-1}$ is $C_1$–$C_4$ alkyl,
—C($Y_{2-2}$)($Y_{2-3}$) where $Y_{2-2}$ and $Y_{2-3}$ are the same or different and are —H or $C_1$–$C_4$ alkyl, $Z_2$ is nothing (a bond), —O—, —S—,
—N($Z_{2-1}$)— where $Z_{2-1}$ is —H or $C_1$–$C_4$ alkyl,
—C≡C—,
—C($Z_{2-2}$)($Z_{2-3}$)— where $Z_{2-2}$ and $Z_{2-3}$ are the same or different and are —H or $C_1$–$C_4$ alkyl,
cis and trans —C($Z_{2-2}$)=C($Z_{2-3}$)— where $Z_{2-2}$ and $Z_{2-3}$ are the same or different and are —H or $C_1$–$C_4$ alkyl, with the provisos (1) that when $Y_1$ is —O—, —S— or —N($Y_{1-1}$)—, then $n_{11}$ is 1 only when $Z_2$ is nothing (a bond), —C≡C—, —C($Z_{2-2}$)($Z_{2-3}$)— or —C($Z_{2-2}$)=C($Z_{2-3}$)— and (2) that when $Y_2$ is —O—, —S— or —N($Y_{2-1}$)—, then $n_{26}$ is 1 only when $Z_2$ is nothing (a bond), —C≡C—, —C($Z_{2-2}$)($Z_{2-3}$)— or —C($Z_{2-2}$)=C($Z_{2-3}$)—, $$-N\begin{matrix} (CH_2)_{n12} \\ \diagup \quad \diagdown \\ \diagdown \quad \diagup \\ (CH_2)_{n13} \end{matrix} N- \quad \text{(Z-III)}$$

where $n_{12}$ is 1 or 2 and $n_{13}$ is 1 or 2, with the proviso that $n_{12}$ and $n_{13}$ can not both be 1, $$-CH\begin{matrix} (CH_2)_{n12} \\ \diagup \quad \diagdown \\ \diagdown \quad \diagup \\ (CH_2)_{n13} \end{matrix} N- \quad \text{(Z-IV)}$$

where $n_{12}$ and $n_{13}$ are as defined above, $$-N\begin{matrix} (CH_2)_{n13} \\ \diagup \quad \diagdown \\ \diagdown \quad \diagup \\ (CH_2)_{n12} \end{matrix} CH-Y_3- \quad \text{(Z-V)}$$

where $Y_3$ is —N($Y_{3-1}$)— where $Y_{3-1}$ is $C_1$–$C_4$ alkyl and $n_{12}$ and $n_{13}$ are as defined above;

$R_6$ is —N=,
—CH=,
—N(O)=, $R_7$ is —CO—N($R_{7-3}$)($R_{7-4}$) where $R_{7-3}$ and $R_{7-4}$ are the same or different and are —H or $C_1$–$C_6$ alkyl,
—N($R_{7-5}$)($R_{7-6}$) where $R_{7-5}$ is
  $C_1$–$C_6$ alkyl,
  —C($R_{7-15}$)($R_{7-16}$)—($R_{7-17}$) where $R_{7-15}$ and $R_{7-16}$ are the same or different and are —H or $C_1$–$C_3$ alkyl and where $R_{7-17}$ is $C_2$–$C_5$ alkenyl containing 1 or 2 double bonds or $C_2$–$C_5$ alkynyl containing 1 triple bond,
  —CH$_2$—CH$_2$—OH,
  —CH$_2$—CH$_2$—CH$_2$—OH,
  —CH(CH$_3$)CH$_2$—O—CH$_3$,
  —CH(CH$_3$)CH$_2$—OH,
  —CH$_2$—CF$_3$,
  —CH$_2$—cyclopropyl,
  —CH$_2$—CH$_2$F,
  —CH$_2$—CH$_2$—C≡N,
  —C*$R_{7-18}$—(CH$_2$)$_{n14}$—C*H$_2$ where $R_{7-18}$ is —H or —CH$_3$, $n_{14}$ is 1 thru 5 and the carbon atoms marked with an asterisk (*) are bonded to each other to resulting in the formation of a ring,
  —(CH$_2$)$_{n1}$—N($R_{7-7}$)($R_{7-8}$) where $n_1$ is 2 or 3 and where $R_{7-7}$ and $R_{7-8}$ are the same or different and are —H or $C_1$–$C_4$ alkyl, and where $R_{7-7}$ and $R_{7-8}$ are taken together with the attached nitrogen atom to form a heterocyclic ring selected from the group consisting of 1-pyrrolidinyl, 1-piperidinyl, 1-piperazinyl or N-morpholinyl, 1-aziridinyl,
and where $R_{7-6}$ is —H,
  $C_1$–$C_6$ alkyl,
  —C($R_{7-15}$)($R_{7-16}$)—($R_{7-17}$) where $R_{7-15}$, $R_{7-16}$ and $R_{7-17}$ are as defined above,
  —CH$_2$—CH$_2$—OH,
  —CH$_2$—CH$_2$—CH$_2$—OH,
  —CH$_2$CF$_3$,
  —CH$_2$—CH$_2$F,
  —CH$_2$—CH$_2$—C≡N,
or where $R_{7-5}$ and $R_{7-6}$ are taken together with the attached nitrogen atom to form a heterocyclic ring selected from the group consisting of 1-pyrrolidinyl, 1-piperidinyl, 1-piperazinyl, N-morpholinyl or 1-aziridinyl,
—(CH$_2$)$_{n4}$—N($R_{7-9}$)($R_{7-10}$) where $n_4$ is 1 or 2 and where $R_{7-9}$ and $R_{7-10}$ are the same or different and are —H or $C_1$–$C_4$ alkyl, and where $R_{7-9}$ and $R_{7-10}$ are taken together with the attached nitrogen atom to form a heterocyclic ring selected from the group consisting of 1-pyrrolidinyl, 1-piperidinyl, 1-piperazinyl or N-morpholinyl, $R_8$ is —N=,
—C$R_{8-1}$= where $R_{8-1}$ is —H, —F, —Cl, —Br, —CF$_3$,
  —NO$_2$, —COCF$_3$,
  $C_1$–$C_6$ alkyl,
  $C_1$–$C_3$ alkylthio,
  —OH,
  —O—$R_{8-2}$ where $R_{8-2}$ is $C_1$–$C_6$ alkyl, —φ, —CO—$R_{8-3}$ where $R_{8-3}$ is $C_1$–$C_6$ alkyl or —φ,
  —NH($R_{8-4}$) where $R_{8-4}$ is
    $C_1$–$C_6$ alkyl,
    —C($R_{8-7}$)($R_{8-8}$)—($R_{8-9}$) where $R_{8-7}$ and $R_{8-8}$ are the same or different and are —H or $C_{1-C3}$ alkyl and where $R_{8-9}$ is $C_2$–$C_5$ alkenyl containing 1 or 2 double bonds or $C_2$–$C_5$ alkynyl containing 1 triple bond,
  —N$R_{8-5}$—CO—$R_{8-6}$ where $R_{8-5}$ is —H or $C_1$–$C_6$ alkyl and $R_{8-6}$ is —H, $C_1$–$C_6$ alkyl or $C_1$–$C_3$ alkoxy;

$R_9$ is —N=,
—C$R_{9-1}$= where $R_{9-1}$ is —H, —F, —Cl, —Br,
  —NO$_2$, —COCF$_3$,
  $C_1$–$C_6$ alkyl,
  $C_1$–$C_3$ alkylthio,
  —OH,
  —O—$R_{9-2}$ where $R_{9-2}$ is $C_1$–$C_6$ alkyl, —φ, —CO—$R_{9-3}$ where $R_{9-3}$ is $C_1$–$C_6$ alkyl or —φ,
  —N($R_{9-4}$)($R_{9-5}$) where $R_{9-4}$ and $R_{9-5}$ are the same or different and are
    —H,
    $C_1$–$C_6$ alkyl,
    —C($R_{9-8}$)($R_{9-9}$)—($R_{9-10}$) where $R_{9-8}$ and $R_{9-9}$ are the same or different and are —H or $C_1$–$C_3$ alkyl and where $R_{9-10}$ is $C_2$–$C_5$ alkenyl containing 1 or 2 double bonds or $C_2$–$C_5$ alkynyl containing 1 triple bond, $R_{9-4}$ and $R_{9-5}$ are taken together with the attached nitrogen atom to form a heterocyclic ring selected from the group consisting of 1-pyrrolidinyl, 1-piperidinyl, 1-piperazinyl or N-morpholinyl, —$NR_{9-6}$—CO—$R_{9-7}$ where $R_{9-6}$ is —H or $C_{-C6}$ alkyl and $R_{9-7}$ is —H, $C_1$–$C_6$ alkyl or $C_1$–$C_3$ alkoxy;

$R_{10}$ is —N=,

—$CR_{10-1}$= where $R_{10-1}$ is —H, —F, —Cl, —Br,
—$CF_3$,
—$NO_2$, —$COCF_3$,
$C_1$–$C_6$ alkyl,
$C_1$–$C_3$ alkylthio,
—OH,
—O—$R_{10-2}$ where $R_{10-2}$ is $C_1$–$C_6$ alkyl, —$\phi$,
—CO—$R_{10-3}$ where $R_{10-3}$ is $C_1$–$C_6$ alkyl or —$\phi$,
—$N(R_{10-4})(R_{10-5})$ where $R_{10-4}$ and $R_{10-5}$ are the same or different and are —H,
$C_1$–$C_6$ alkyl,
—$C(R_{10-8})(R_{10-9})$—$(R_{10-10})$ where $R_{10-8}$ and $R_{10-9}$ are the same or different and are —H or $C_1$–$C_3$ alkyl and where $R_{10-10}$ is $C_2$–$C_5$ alkenyl containing 1 or 2 double bonds or $C_2$–$C_5$ alkynyl containing 1 triple bond,
—$NR_{10-6}$—CO—$R_{10-7}$ where $R_{10-6}$ is —H or $C_1$–$C_6$ alkyl and $R_{10-7}$ is —H, $C_1$–$C_6$ alkyl or $C_1$–$C_3$ alkoxy;

with the proviso that not more than two of $R_6$, $R_8$, $R_9$ and $R_{10}$ are —N=;

Aryl/Heteroaryl is a substituent selected from the group of substituents of formula (1)

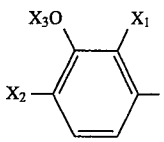

(1)

where $X_1$ is —H, $C_1$–$C_6$ n-alkyl,
$X_2$ is —H, $C_1$–$C_6$ n-alkyl,
$X_3$ is $C_1$–$C_6$ alkyl,
—CO—$X_{3-1}$ where $X_{3-1}$ is $C_1$–$C_4$ alkyl or —$\phi$,
—$CH_2$—$\phi$,
—$\phi$;

of formula (2)

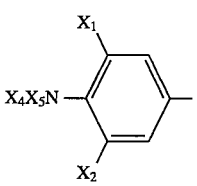

(2)

where $X_4$ and $X_5$ are the same or different and are —H, $C_1$–$C_4$ alkyl,
—$(CH_2)_{n5}$—$N(X_{4-1})(X_{4-2})$ where $n_5$ is 2 or 3 and where $X_{4-1}$ and $X_{4-2}$ are the same or different and are —H or $C_1$–$C_4$ alkyl or where $X_{4-1}$ and $X_{4-2}$ are taken together with the attached nitrogen atom to form a heterocyclic ring selected from the group consisting of 1-pyrrolidinyl, 1-piperidinyl, 1-piperazinyl or N-morpholinyl, and where $X_4$ and $X_5$ are taken together with the attached nitrogen atom to form a heterocyclic ring selected from the group consisting of 1-pyrrolidinyl, 1-piperidinyl, 1-piperazinyl or N-morpholinyl, and where $X_1$ and $X_2$ are as defined above, with the proviso that both $X_4$ and $X_5$ are not both —H;

of formula (3)

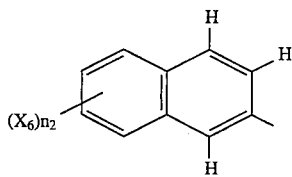

(3)

where
$X_6$ is —H,
$C_1$–$C_6$ alkyl,
—F, —Cl, Br,
—OH, —O—$CH_2$—$\phi$, —O—$CF_3$,
—O—$CH_2$—$COOX_{6-14}$ where $X_{6-14}$ is —H, $C_1$–$C_6$ alkyl, —$\phi$, —$CH_2$—$\phi$,
—CHO,
$C_1$–$C_3$ alkoxy,
$C_1$–$C_3$ alkylthio,
—O—CO—$X_{6-1}$ where $X_{6-1}$ is —H, $C_1$–$C_4$ alkyl or —$\phi$,
—O—$SO_2$—$X_{6-12}$ where $X_{6-12}$ is $C_1$–$C_4$ alkyl,
—COO—$X_{6-13}$ where $X_{6-13}$ is —H, $C_1$–$C_4$ alkyl, —$\phi$ or —$CH_2$—$\phi$,
—C≡N,
—$NO_2$, —$N_3$,
—$NX_{6-10}X_{6-11}$ where $X_{6-10}$ and $X_{6-11}$ are the same or different and are —H or $C_1$–$C_5$ alkyl or where $X_{6-10}$ and $X_{6-11}$ are taken together with the attached nitrogen atom to form a heterocyclic ring selected from the group consisting of 1-pyrrolidinyl, 1-piperidinyl, 1-piperazinyl, N-morpholinyl or 1-aziridinyl,
—$N(X_{6-2})(CH_2)_{n3}$—$N(X_{6-3})(X_{6-4})$ where $n_3$ is 2 thru 5, $X_{6-2}$ is —H or $C_{1-4}$ alkyl, $X_{6-3}$ is —H or $C_{1-4}$ alkyl, $X_{6-4}$ is —H or $C_{1-4}$ alkyl, or where $X_{6-3}$ and $X_{6-4}$ are taken together with the attached nitrogen atom to form a heterocyclic ring selected from the group consisting of 1-pyrrolidinyl, 1-piperidinyl, 1-piperazinyl, N-morpholinyl or 1-aziridinyl,
—O—CO—$(CH_2)_{n3}$—COOH, where $n_3$ is as defined above,
—O—$(CH_2)_{n3}$—$N(X_{6-3})(X_{6-4})$ where $n_3$, $X_{6-3}$ and $X_{6-4}$ are as defined above,
—$(CH_2)_{n24}$—OH, where $n_{24}$ is 1 thru 5,
—$(CH_2)_{n6}$—$N(X_{6-5})(X_{6-6})$ where $n_6$ is 1 thru 5 and $X_{6-5}$ and $X_{6-6}$ are the same or different and are —H, $C_1$–$C_4$ alkyl or where $X_{6-5}$ and $X_{6-6}$ are taken together with the attached nitrogen atom to form a heterocyclic ring selected from the group consisting of 1-pyrrolidinyl, 1-piperidinyl, 1-piperazinyl or N-morpholinyl,
—NH—$SO_2$—$X_{6-7}$ where $X_{6-7}$ is $C_1$–$C_4$ alkyl, $C_3$–$C_7$ cycloalkyl, —$\phi$ or —$CH_2$—$\phi$,
—N=$C(X_{6-4})$—$N(X_{6-7})(X_{6-8})$ where
  (a) $X_{6-8}$ is $C_1$–$C_4$ alkyl, $C_3$–$C_7$ cycloalkyl or —$\phi$ and where $X_{6-4}$ is —H or $C_{1-4}$ alkyl, and $X_{6-7}$ is as defined above,
  (b) $X_{6-7}$ and $X_{6-8}$ are taken together with the attached nitrogen atom to form a heterocyclic ring selected from the group consisting of 1-pyrrolidinyl, 1-piperidinyl, 1-piperazinyl or N-morpholinyl,
  (c) $X_{6-4}$ and $X_{6-7}$ are taken together with the attached nitrogen atom to form a heterocyclic ring selected from the group consisting of 1-pyrrolidinyl or 1-piperidinyl,
—$NX_{6-4}$—CO—$X_{6-9}$ where $X_{6-9}$ is —H, $C_1$–$C_4$ alkyl or —$\phi$ and where $X_{6-4}$ is —H or $C_{1-4}$ alkyl,
—O—prodrug where prodrug is —$PO_2$—$O^-$cation$^+$,
—CO—$CH_2$—CO—NH—$CH_2$—$SO_2$—$O^-$cation$^+$,
—CO—$(CH_2)_{n21}$—$R_{51}$ where $n_{21}$ is 1–7 and $R_{51}$ is
—$COO^-$ cation$^+$,
—$NR_{51-1}R_{51-2}$ where $R_{51-1}$ and $R_{51-2}$ are the same or different and are —H or $C_1$–$C_3$ alkyl,
—$N^+R_{51-1}R_{51-2}R_{51-3}$ halide$^-$ where $R_{51-1}$, $R_{51-2}$ and $R_{51-3}$ are the same or different and are —H or $C_1$–$C_3$ alkyl, and where halide is —Cl or —Br,
—CO—CH(AA)—$NH_2$ where AA is —$CH_3$, —$CH(CH_3)_2$, —$CH_2$—$CH(CH_3)_2$, —$CH_2$—OH, —CH(OH)($CH_3$), —$CH_2$—$\phi$, —$CH_2$—[p-hydroxyphenyl], —$CH_2$—[3-indolyl], —$CH_2$—S—S—$CH_2$—$CH(NH_2)$—COOH, —$CH_2$—SH, —$CH_2CH_2$—S—$CH_3$, —$CH_2$—COOH, —$CH_2$—CO—$NH_2$, —$CH_2$—$CH_2$—COOH, —$CH_2$—$CH_2$—CO—$NH_2$, —$CH_2$—[2-HISTIDYL], —$(CH_2)_3$—NH—C(NH)—$NH_2$, —$(CH_2)_4$—$NH_2$, —$CH_2$—$CH_2$—CH(OH)—$CH_2$—$NH_2$, —$(CH_2)_3$—$NH_2$, —$(CH_2)_3$—NH—CO—$NH_2$ —$CH_2CH_2$—OH,
—CO—CH=CH—CO—$O^-$cation$^+$,
—CO—N*—CH=CH—N=CH* where the atoms marked with an asterisk (*) are bonded to each other resulting in the formation of a ring,
4—(NHR$_{52}$)-benzoyl,
—CO—C*=CH—CH=C(—$NR_{52}$)—CH=CH* where $R_{52}$ is —H or $C_1$–$C_3$ alkyl and where the atoms marked with an asterisk (*) are bonded to each other resulting in the formation of a ring,
—CO—$(CH_2)_{n21}$—CO—O—[$C_6H_{12}O_6$ sugars],
—CO—O—$CH(CH_2$—O—CO—$R_{53})_2$ where the $R_{53}$'s are the same or different and are $C_1$–$C_{18}$,
—CO—$(CH_2)_6$—CO—N($CH_3$)—$CH_2$—$CH_2$—$SO_3^-$cation$^+$,
—$CH_2$—O—CO—$(CH_2)_{n21}$—$NR_{51-1}R_{51-2}$ where $n_{21}$, $R_{51-1}$ and $R_{51-2}$ are as defined above,
—CO—NH—$C_6H_4$—$R_{55}$ where $R_{55}$ is —H or $C_1$–$C_3$ alkyl, —$NO_2$, —$NR_{51-1}R_{51-2}$ where $R_{51-1}$ and $R_{51-2}$ are as defined above,
—$NX_{6-4}$-prodrug where $X_{6-4}$ and prodrug are as defined above except that prodrug is not —$PO_2$—$O^-$, $n_2$ is 1 thru 3, the $X_6$'s can be the same or can be different and where when $n_2$ is 2 and the two $X_6$ groups are ortho to each other they can be taken together to form —O—$CH_2$—O—; with the proviso that if $n_2$ is 2 or 3, only one of the $X_6$'s can be a prodrug, of formula (4)

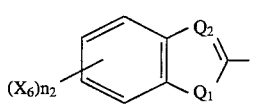
(4)

where $Q_1$ is —$NX_{11}$- where $X_{11}$ is —H, —$SO_2$—$\phi$, —$SO_2$—$CH_3$, —CO—$X_{11-1}$ where $X_{11-1}$ is $C_1$–$C_4$ alkyl, —$CF_3$ or —$\phi$;

$Q_2$ is —N= provided $R_1$ is not —$CH_2$—,
—$CX_{12}$= where $X_{12}$ is
—COO—$X_{12-1}$ where $X_{12-1}$ is —H or $C_1$–$C_4$ alkyl,
—CO—$N(X_{12-2})(X_{12-3})$ where $X_{12-2}$ and $X_{12-3}$ are the same or different and are —H, $C_1$–$C_4$ alkyl or where $X_{12-2}$ and $X_{12-3}$ are taken together with the attached nitrogen atom to form a heterocyclic ring selected from the group consisting of 1-pyrrolidinyl, 1-piperidinyl, 1-piperazinyl or N-morpholinyl,
—CO—COO—$X_{12-1}$ where $X_{12-1}$ is as defined above,
$C_1$–$C_3$ alkyl,
—CO—$\phi$,
—CO—$X_{12-1}$ where $X_{12-1}$ is as defined above,
—CO—CO—$N(X_{12-2})(X_{12-3})$ where $X_{12-2}$ and $X_{12-3}$ are as defined above,
—$(CH_2)_{n23}$—OH where $n_{23}$ is 1 or 2,
and where $X_6$ and $n_2$ are as defined above, of formula (6)

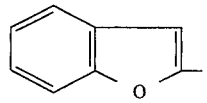
(6)

of formula (7)

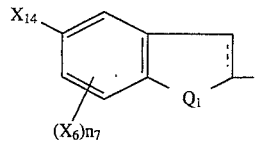
(7)

where .... is a single or double bond,
$X_{14}$ is —H,
—O—$CH_2$—$\phi$, —O—$CF_3$,
—O—$CH_2$—$COOR_{14-10}$ where $R_{14-10}$ is —H, $C_1$–$C_4$ alkyl, —$\phi$ or —$CH_2$—$\phi$,
$C_1$–$C_6$ alkyl,
—F, —Cl, Br,
—O—$SO_2$—$X_{14-11}$ where $X_{14-11}$ is $C_1$–$C_4$ alkyl,
—C≡N,
—CHO,
—$(CH_2)_{n25}$—OH where $n_{25}$ is 1 thru 5,
—$NO_2$, —$NH_2$, —$N_3$,
—NH—$CH_2$—$\phi$, —NH—$SO_2$—$X_{14-1}$ where $X_{14-1}$ is $C_1$–$C_6$ alkyl, $C_3$–$C_7$ cycloalkyl or —$\phi$,
—$NX_{14-2}(CH_2)_{n3}$—$N(X_{14-3})(X_{14-4})$ where $n_3$ is 2 thru 5, $X_{14-2}$ is —H or $C_{1-4}$ alkyl, $X_{14-3}$ is —H or $C_{1-4}$ alkyl, $X_{14-4}$ is —H or $C_{1-4}$ alkyl, or where $X_{14-3}$ and $X_{14-4}$ are taken together with the attached nitrogen atom to form a heterocyclic ring selected from the group consisting of 1-pyrrolidinyl, 1-piperidinyl, 1-piperazinyl or N-morpholinyl,
—$NX_{14-13}X_{14-14}$ where $X_{14-13}$ and $X_{14-14}$ are the same or different and are —H or $C_1$–$C_5$ alkyl or where $X_{14-13}$ and $X_{14-14}$ are taken together with the attached nitrogen atom to form a heterocyclic ring selected from the group consisting of 1-pyrrolidinyl, 1-piperidinyl, 1-piperazinyl or N-morpholinyl,
—$(CH_2)_{n6}$—$N(X_{14-5})(X_{14-6})$ where $n_6$ is 1 thru 5 and $X_{14-5}$ and $X_{14-6}$ are the same or different and are —H, $C_1$–$C_4$ alkyl or where $X_{14-5}$ and $X_{14-6}$ are taken together with the attached nitrogen atom to form a heterocyclic ring selected from the group consisting of 1-pyrrolidinyl, 1-piperidinyl, 1-piperazinyl or N-morpholinyl,
—N=$C(X_{14-4})$—$N(X_{14-7})(X_{14-8})$ where
(a) $X_{14-7}$ and $X_{14-8}$ are $C_1$–$C_6$ alkyl, $C_3$–$C_7$ cycloalkyl or —$\phi$, where $X_{14-4}$ is as defined above,
(b) $X_{14-7}$ and $X_{14-8}$ are taken together with the attached nitrogen atom to form a heterocyclic ring selected from the group consisting of 1-pyrrolidinyl, 1-piperidinyl, 1-piperazinyl or N-morpholinyl, (c) $X_{14-4}$ and $X_{14-7}$ are taken together with the attached nitrogen atom to form a heterocyclic ring selected from the group consisting of 1-pyrrolidinyl or 1-piperidinyl, —CO—O—$X_{14-7}$ where $X_{14-7}$ is as defined above, —CO—N($X_{14-7}$)($X_{14-8}$) where $X_{14-7}$ and $X_{14-8}$ are as defined above, —N($X_{14-2}$)—CO—$X_{14-9}$ where $X_{14-9}$ is —H, $C_1$–$C_4$ alkyl or —φ where $X_{14-2}$ is defined above, —N($X_{14-2}$)-prodrug, where prodrug is as defined above except that it is not —$PO_2$—O—, and when $X_{14-2}$ is as defined above, $n_7$ is 0 thru 2, $X_6$ and $Q_1$ are as defined above;

of formula (8)

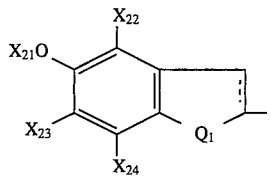

(8)

where $X_{21}$ is —H, $C_1$–$C_4$ alkyl, —CO—($C_1$–$C_4$ alkyl), —$CH_2$—φ, —CO—φ or —prodrug where prodrug is as defined above, $X_{22}$, $X_{23}$ and $X_{24}$ are the same or different and are
- —F, —Cl, Br,
- —OH, —O—$CH_2$—φ, —O—$CF_3$, —O—$CH_2$—COOH,
- $C_1$–$C_3$ alkoxy,
- $C_1$–$C_3$ alkylthio,
- —O—CO—$X_{22-1}$ where $X_{22-1}$ is —H, $C_1$–$C_4$ alkyl or —φ
- —$NO_2$, —$NH_2$, —$N_3$,
- —C≡N,
- —$NX_{22-2}(CH_2)_{n9}$—N($X_{22-3}$)($X_{22-4}$) where $n_9$ is 2 thru 5, $X_{22-2}$ is —H or $C_1$–$C_4$ alkyl, $X_{22-3}$ is —H or $C_1$–$C_4$ alkyl, $X_{22-4}$ is —H or $C_1$–$C_4$ alkyl, and where $X_{22-3}$ and $X_{22-4}$ are taken together with the attached nitrogen atom to form a heterocyclic ring selected from the group consisting of 1-pyrrolidinyl, 1-piperidinyl, 1-piperazinyl or N-morpholinyl,
- —O—CO—$(CH_2)_{n9}$—COOH, where $n_9$ is as defined above,
- —O—$(CH_2)_{n9}$—N($X_{23-3}$)($X_{22-4}$) where $n_9$, $X_{22-3}$ and $X_{22-4}$ are as defined above,
- —$(CH_2)_{n10}$—N($X_{22-5}$)($X_{22-6}$) where $n_{10}$ is 1 thru 5 and $X_{22-5}$ and $X_{22-6}$ are the same or different and are —H, $C_1$–$C_4$ alkyl and where $X_{22-5}$ and $X_{22-6}$ are taken together with the attached nitrogen atom to form a heterocyclic ring selected from the group consisting of 1-pyrrolidinyl, 1-piperidinyl, 1-piperazinyl or N-morpholinyl,
- —N($X_{22-7}$)($X_{22-8}$) where $X_{22-7}$ and $X_{22-8}$ are $C_1$–$C_6$ alkyl, $C_3$–$C_7$ cycloalkyl or —φ, and where any adjacent two of —O—$X_{21}$, $X_{22}$, $X_{23}$ or $X_{24}$ are taken together to form a methylenedioxy group (—O—$CH_2$—O—), $Q_1$ and ⋯ are as defined above;

of formula (9)

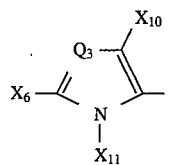

(9)

where $X_{10}$ is —H, —F, —Cl or —Br, $Q_3$ is —CH= or $Q_2$ where $Q_2$ is as defined above, $X_6$ and $X_{11}$ are as defined above;

of formula (10)

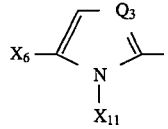

(10)

where $X_6$, $X_{11}$ and $Q_3$ are as defined above;

of formula (11)

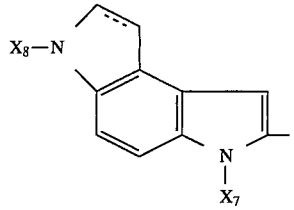

(11)

where $X_7$ is —H, —$SO_2$—φ, —$SO_2$—$CH_3$, —CO—$X_{7-1}$ where $X_{7-1}$ is $C_1$–$C_4$ alkyl or —φ, $X_8$ is —H, $C_1$–$C_6$ alkyl, —$CH_2$—φ, —$SO_2$—φ, —$SO_2$—$CH_3$, —CO—$X_{8-1}$ where $X_{8-1}$ is $C_1$–$C_4$ alkyl or —φ, ⋯ is as defined above;

of formula (15)

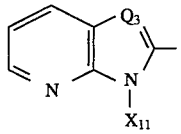

(15)

where $Q_3$ and $X_{11}$ are as defined above;

of formula (16)

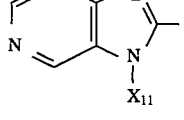

(16)

where $Q_3$ and $X_{11}$ are as defined above;

of formula (17)

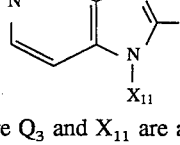

(17)

where $Q_3$ and $X_{11}$ are as defined above;

of formula (18)

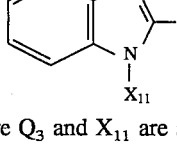

(18)

where $Q_3$ and $X_{11}$ are as defined above;

of formula (19)

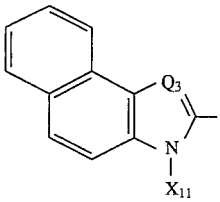
(19)

where $Q_3$ and $X_{11}$ are as defined above;
of formula (20)

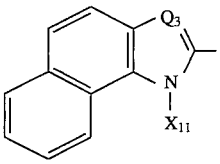
(20)

where $Q_3$ and $X_{11}$ are as defined above;
of formula (21)

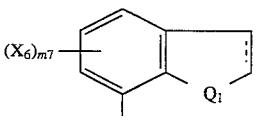
(21)

where $Q_1$, $X_6$ and $n_7$ are as defined above;
with the proviso that one of $R_{7-5}$ or $R_{7-6}$ must be —H when $R_6$ is not —N=, enantiomers, pharmaceutically acceptable salts, hydrates and solvates thereof.

Also disclosed are anti-AIDS piperazines (IV) selected from the group consisting of compounds of EXAMPLES 1, 3–5, 7, 12, 16, 26, 28, 37, 38, 42, 45, 64, 77, 78, 80, 107, 116, 135, 136 and 145–148 enantiomers, pharmaceutically acceptable salts, hydrates and solvates thereof.

Further disclosed is a method of treating an individual infected with the human immunodeficiency virus (HIV) which comprises administering an effective amount of an indole of formula (V)

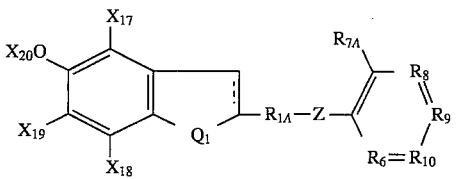
(V)

where $R_{1A}$ is —$CH_2$—,
—CO—,
—$SO_2$—,
—CH=CH—CO—,
—CO—$CH_2$—,
where Z is

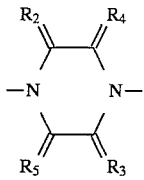
(Z-I)

where
(I) $R_2$ is =O or $R_{2-1}$:$R_{2-2}$ where one of $R_{2-1}$ and $R_{2-2}$ is —H and the other of $R_{2-1}$ and $R_{2-2}$ is —H or —$CH_3$,
$R_3$ is =O or $R_{3-1}$:$R_{3-2}$ where one of $R_{3-1}$ and $R_{3-2}$ is —H and other of $R_{3-1}$ and $R_{3-2}$ is —H or —$CH_3$, $R_4$ is $R_{4-1}$:$R_{4-2}$ and $R_5$ is $R_{5-1}$:$R_{5-2}$ where one of $R_{4-1}$ and $R_{4-2}$ is —H and the other of $R_{4-1}$ and $R_{4-2}$ is —H or —$CH_3$, where one of $R_{5-2}$ and $R_{5-2}$ is —H and the other of $R_{5-1}$ and $R_{5-2}$ is —H or —$CH_3$, (II) $R_4$ is $R_{4-3}$:$R_{4-4}$ and $R_5$ is $R_{5-3}$:$R_{5-4}$ where one of $R_{4-3}$ and $R_{4-4}$ and one of $R_{5-3}$ and $R_{5-4}$ are taken together to form —$CH_2$— and the other of $R_{4-3}$ and $R_{4-4}$, and $R_{5-3}$ and $R_{5-4}$ are —H, $R_2$ and $R_3$ are —H:—H, (III) $R_2$ is $R_{2-5}$:$R_{2-6}$ and $R_5$ is $R_{5-5}$:$R_{5-6}$ where one of $R_{2-5}$ and $R_{2-6}$ and one of $R_{5-5}$ and $R_{5-6}$ are taken together to form —$CH_2$—$CH_2$— and the other of $R_{2-5}$ and $R_{2-6}$, and $R_{5-5}$ and $R_{5-6}$ are —H, and $R_3$ and $R_4$ are —H:—H, (IV) $R_3$ is $R_{3-5}$:$R_{3-6}$ and $R_4$ is $R_{4-5}$:$R_{5-6}$ where one of $R_{3-5}$ and $R_{3-6}$ and one of $R_{4-5}$ and $R_{4-6}$ are taken together to form —$CH_2$—$CH_2$— and the other of $R_{3-5}$ and $R_{3-6}$, and $R_{4-5}$ and $R_{4-6}$ are —H, and $R_2$ and $R_5$ are —H:—H, $$—Y_1—(CH_2)_{n11}—Z_2—(CH_2)_{n26}—Y_2— \qquad (Z\text{-II})$$

where $n_{11}$ is 1 thru 5,
$n_{26}$ is 1 thru 5,
$Y_1$ is —O—, —S—,
—N($Y_{1-1}$)— where $Y_{1-1}$ is $C_1$–$C_4$ alkyl,
—C($Y_{1-2}$)($Y_{1-3}$) where $Y_{1-2}$ and $Y_{1-3}$ are the same or different and are —H or $C_1$–$C_4$ alkyl,
$Y_2$ is —O—, —S—,
—N($Y_{2-1}$)— where $Y_{2-1}$ is $C_1$–$C_4$ alkyl,
—C($Y_{2-2}$)($Y_{2-3}$) where $Y_{2-2}$ and $Y_{2-3}$ are the same or different and are —H or $C_1$–$C_4$ alkyl,
$Z_2$ is nothing (a bond), —O—, —S—,
—N($Z_{2-1}$)— where $Z_{2-1}$ is —H or $C_1$–$C_4$ alkyl,
—C≡C—,
—C($Z_{2-2}$)($Z_{2-3}$)— where $Z_{2-2}$ and $Z_{2-3}$ are the same or different and are —H or $C_1$–$C_4$ alkyl,
cis and trans —C($Z_{2-2}$)=C($Z_{2-3}$)— where $Z_{2-2}$ and $Z_{2-3}$ are the same or different and are —H or $C_1$–$C_4$ alkyl, with the provisos (1) that when $Y_1$ is —O—, —S— or —N($Y_{1-1}$)—, then $n_{11}$ is 1 only when $Z_2$ is nothing (a bond), —C≡C—, —C($Z_{2-2}$)($Z_{2-3}$)— or —C($Z_{2-2}$)=C($Z_{2-3}$)— and (2) that when $Y_2$ is —O—, —S— or—N($Y_{2-1}$)—, then $n_{26}$ is 1 only when $Z_2$ is nothing (a bond), —C≡C—, —C($Z_{2-2}$)($Z_{2-3}$)— or —C($Z_{2-2}$)=C($Z_{2-3}$)—, $$\begin{array}{c} \diagup\!\!\!\!(CH_2)_{n12}\!\!\diagdown \\ -N \qquad\qquad N- \\ \diagdown\!\!\!\!(CH_2)_{n13}\!\!\diagup \end{array} \qquad (Z\text{-III})$$

where $n_{12}$ is 1 or 2 and $n_{13}$ is 1 or 2, with the proviso that $n_{12}$ and $n_{13}$ are not both —H, $$\begin{array}{c} \diagup\!\!\!\!(CH_2)_{n12}\!\!\diagdown \\ -CH \qquad\qquad N- \\ \diagdown\!\!\!\!(CH_2)_{n13}\!\!\diagup \end{array} \qquad (Z\text{-IV})$$

where $n_{12}$ and $n_{13}$ are as defined above, where $n_{12}$ and $n_{13}$ are not both 1, $$\begin{array}{c} \diagup\!\!\!\!(CH_2)_{n13}\!\!\diagdown \\ -N \qquad\qquad CH—Y_3— \\ \diagdown\!\!\!\!(CH_2)_{n12}\!\!\diagup \end{array} \qquad (Z\text{-V})$$

where $Y_3$ is —N($Y_{3-1}$)— where $Y_{3-1}$ is $C_1$–$C_4$ alkyl and $n_{12}$ and $n_{13}$ are as defined above;
$R_6$ is —N=,
—CH=,

—N(O)=;

$R_{7A}$ is —S—$R_{7A-1}$ where $R_{7A-1}$ is $C_1$–$C_6$ alkyl,
—O—$R_{7A-2}$ where $R_{7A-2}$ is
$C_1$–$C_6$ alkyl,
—C($R_{7A-15}$)($R_{7A-17}$)—($R_{7A-17}$) where $R_{7A-15}$ and $R_{7A-16}$ are the same or different and are —H or $C_1$–$C_3$ alkyl and where $R_{7A-17}$ is $C_2$–$C_5$ alkenyl containing 1 or 2 double bonds or $C_2$–$C_5$ alkynyl containing 1 triple bond,
—CO—$R_7A_{-11}$ where $R_7A_{-11}$ is —H,
$C_2$–$C_6$ alkyl,
$C_2$–$C_6$ alkenyl containing 1 or 2 double bonds,
$C_2$–$C_6$ alkynyl containing 1 triple bond,
—$CH_2$—$\phi$,
—$\phi$ optionally substituted with 1 thru 3
—$CF_3$,
$C_1$–$C_4$ alkyl,
—OH,
$C_1$–$C_3$ alkylthio,
—O—CO—$R_{7A-12}$ where $R_{7A-12}$ is $C_1$–$C_6$ alkyl or —$\phi$,
—F, —Cl, —Br,
—CO—$CF_3$,
—$NO_2$,
—N($R_{7A-13}$)($R_{7A-14}$) where $R_7A_{-13}$ and $R_{7A-14}$ are the same or different and are —H, $C_1$–$C_3$ alkyl and where $R_{7A-13}$ and $R_{7A-14}$ are taken together with the attached nitrogen atom to form a heterocyclic ring selected from the group consisting of 1-pyrrolidinyl, 1-piperidinyl, 1-piperazinyl or N-morpholinyl,
—COO—$R_{7A-11}$ where $R_{7A-11}$ is as defined above,
—CO—N($R_{7A-3}$)($R_{7A-4}$) where $R_{7A-3}$ and $R_{7A-4}$ are the same or different and are —H or $C_1$–$C_6$ alkyl,
—N($R_{7A-5}$)($R_{7A-6}$) where $R_{7A-5}$ is
$C_1$–$C_6$ alkyl,
—C($R_{7A-15}$)($R_{7A-16}$)–($R_{7A-17}$) where $R_{7A-15}$, $R_{7A-16}$ and $R_{7A-17}$ are as defined above,
—$CH_2$—$CH_2$—OH,
—$CH_2$—$CH_2$—$CH_2$—OH,
—CH($CH_3$)$CH_2$—O—$CH_3$,
—$CH_2$—cyclopropyl,
—CH($CH_3$)$CH_2$—OH,
—$CH_2$—$CF_3$,
—$CH_2$—$CH_2$F,
—$CH_2$—$CH_2$—C≡N,
—C*H—($CH_2$)$_{n14}$—C*$H_2$ where $n_{14}$ is 1 thru 5 and the carbon atoms marked with an asterisk (*) are bonded to each other to resulting in the formation of a ring,
—($CH_2$)$n_1$—N($R_{7A-7}$)($R_{7A-8}$) where $n_1$ is 2 or 3 and where $R_{7A-7}$ and $R_{7A-8}$ are the same or different and are —H or $C_1$–$C_4$ alkyl, and where $R_{7A-7}$ and $R_{7A-8}$ are taken together with the attached nitrogen atom to form a heterocyclic ring selected from the group consisting of 1-pyrrolidinyl, 1-piperidinyl, 1-piperazinyl, N-morpholinyl, 1-aziridinyl,
and where $R_{7A-6}$ is —H,
$C_1$–$C_6$ alkyl,
—C($R_{7A-15}$)($R_{7A-16}$)—($R_{7A-17}$) where $R_{7A-15}$, $R_{7A-16}$ and $R_{7A-17}$ are as defined above,
—$CH_2$—$CH_2$—OH,
—$CH_2$—$CH_2$—$CH_2$—OH,
—$CH_2CF_3$,
—$CH_2$—$CH_2$F,
—$CH_2$—$CH_2$—C≡N,
or where $R_{7A-5}$ and $R_{7A-6}$ are taken together with the attached nitrogen atom to form a heterocyclic ring selected from the group consisting of 1-pyrrolidinyl, 1-piperidinyl, 1-piperazinyl, N-morpholinyl or 1-aziridinyl,
—($CH_2$)$_{n4}$—N($R_{7A-9}$)($R_{7A-10}$) where $n_4$ is 1 or 2 and where $R_{7A-9}$ and $R_{7A-10}$ are the same or different and are —H or $C_1$–$C_4$ alkyl, and where $R_{7A-9}$ and $R_7A_{-10}$ are taken together with the attached nitrogen atom to form a heterocyclic ring selected from the group consisting of 1-pyrrolidinyl, 1-piperidinyl, 1-piperazinyl or N-morpholinyl, $R_8$ is —N=, —$CR_{8-1}$= where $R_{8-1}$ is —H, —F, —Cl, —Br, —$CF_3$, —$NO_2$, —$COCF_3$,
$C_1$–$C_6$ alkyl,
$C_1$–$C_3$ alkylthio,
—OH,
—O—$R_{8-2}$ where $R_{8-2}$ is $C_1$–$C_6$ alkyl, —$\phi$, —CO—$R_{8-3}$ where $R_{8-3}$ is $C_1$–$C_6$ alkyl or —$\phi$,
—NH($R_{8-4}$) where $R_{8-4}$ is
$C_1$–$C_6$ alkyl,
—C($R_{8-7}$)($R_{8-8}$)—($R_{8-9}$) where $R_{8-7}$ and $R_{8-8}$ are the same or different and are —H or $C_1$–$C_3$ alkyl and where $R_{8-9}$ is $C_2$–$C_5$ alkenyl containing 1 or 2 double bonds or $C_2$–$C_5$ alkynyl containing 1 triple bond,
—$NR_{8-5}$—CO—$R_{8-6}$ where $R_{8-5}$ is —H or $C_1$–$C_6$ alkyl and $R_{8-6}$ is —H, $C_1$–$C_6$ alkyl or $C_1$–$C_3$ alkoxy;

$R_9$ is —N= or —$CR_{9-1}$= where $R_{9-1}$ is —H, —F, —Cl, —Br, —$NO_2$, —$COCF_3$,
$C_1$–$C_6$ alkyl,
$C_1$–$C_3$ alkylthio,
—OH,
—O—$R_{9-2}$ where $R_{9-2}$ is $C_1$–$C_6$ alkyl, —$\phi$, —CO—$R_{9-3}$ where $R_{9-3}$ is $C_1$–$C_6$ alkyl or —$\phi$, with the proviso that $R_{9-2}$ is not alkyl when $R_7$ is —$OR_{7-2}$,
—N($R_{9-4}$)($R_{9-5}$) where $R_{9-4}$ and $R_{9-5}$ are the same or different and are —H,
$C_1$–$C_6$ alkyl,
—C($R_{9-8}$)($R_{9-9}$)—($R_{9-10}$) where $R_{9-8}$ and $R_{9-9}$ are the same or different and are —H or $C_1$–$C_3$ alkyl and where $R_{9-10}$ is $C_2$–$C_5$ alkenyl containing 1 or 2 double bonds or $C_2$–$C_5$ alkynyl containing 1 triple bond,
$R_{9-4}$ and $R_{9-5}$ are taken together with the attached nitrogen atom to form a heterocyclic ring selected from the group consisting of 1-pyrrolidinyl, 1-piperidinyl, 1-piperazinyl or N-morpholinyl,
—$NR_{9-6}$—CO—$R_{9-7}$ where $R_{9-6}$ is —H or $C_1$–$C_6$ alkyl and $R_{9-7}$ is —H, $C_1$–$C_6$ alkyl or $C_1$–$C_3$ alkoxy;

$R_{10}$ is —N= or —$CR_{10-1}$ is —H, —F, —Cl, —Br, —$CF_3$, —$NO_2$, —$COCF_3$,
$C_1$–$C_6$ alkyl,
$C_1$–$C_3$ alkylthio,
—OH,
—O—$R_{10-2}$ where $R_{10-2}$ is $C_1$–$C_6$ alkyl, —$\phi$, —CO—$R_{10-3}$ where $R_{10-3}$ is $C_1$–$C_6$ alkyl or —$\phi$,
—N($R_{10-4}$)($R_{10-5}$) where $R_{10-4}$ and $R_{10-5}$ are the same or different and are —H,
$C_1$–$C_6$ alkyl,
—C($R_{10-8}$)($R_{10-9}$)—($R_{10-10}$) where $R_{10-8}$ and $R_{10-9}$ are the same or different and are —H or $C_1$–$C_3$ alkyl and where $R_{10-10}$ is $C_2$–$C_5$ alkenyl containing 1 or 2 double bonds or $C_2$–$C_5$ alkynyl containing 1 triple bond,
—$NR_{10-6}$—CO—$R_{10-7}$ where $R_{10-6}$ is —H or $C_1$–$C_6$ alkyl and $R_{10-7}$ is —H, $C_1$–$C_6$ alkyl or $C_1$–$C_3$ alkoxy,
with the proviso that not more than two of $R_6$, $R_8$, $R_9$ and $R_{10}$ are —N=;
where ---- is a single or double bond;

$Q_1$ is $-NX_{11}$ where $X_{11}$ is $-H$, $-SO_2-\phi$, $-SO_2-CH_3$, $-CO-X_{11-1}$ where $X_{11-1}$ is $C_1-C_4$ alkyl, $-CF_3$ or $-\phi$;

$X_{17}$ is $-H$ or $-CH_3$;

$X_{18}$ is $-H$ or $-CH_3$;

$X_{19}$ is $-H$ or $-CH_3$;

$X_{20}$ is $-H$, $C_1-C_4$ alkyl, $-CO-(C_1-C_4$ alkyl), $-CH_2-\phi$, $-CO-\phi$ or $-$prodrug where prodrug is
$-PO_2-O^-$cation$^+$,
$-CO-CH_2-CO-NH-CH_2-SO_2-O^-$cation$^+$,
$-CO-(CH_2)_{n21}-R_{51}$ where $n_{21}$ is 1–7 and $R_{51}$ is $-COO^{-cation}+$, $-NR_{51-1}R_{51-2}$ where $R_{51-1}$ and $R_{51-2}$ are the same or different and are $-H$ or $C_1-C_3$ alkyl, $-N^+R_{51-1}R_{51-2}R_{51-3}$halide where $R_{51-1}$, $R_{51-2}$ and $R_{51-3}$ are the same or different and are $-H$ or $C_1-C_3$ alkyl, and where halide is $-Cl$ or $-Br$,
$-CO-CH(AA)-NH_2$ where AA is $-H$, $-CH_3$, $-CH(CH_3)_2$, $-CH_2-CH(CH_3)_2$, $-CH_2-OH$, $-CH(OH)(CH_3)$, $-CH_2-\phi$, $-CH_2-$[p-hydroxyphenyl], $-CH_2-$[3-indolyl], $-CH_2-S-S-CH_2-CH(NH_2)-COOH$, $-CH_2-SH$, $-CH_2CH_2-S-CH_3$, $-CH_2-COOH$, $-CH_2-CO-NH_2$, $-CH_2-CH_2-COOH$, $-CH_2-CH_2-CO-NH_2$, $-CH_2-$]2-HISTIDYL], $-(CH_2)_3-NH-C(NH)-NH_2$, $-(CH_2)_4-NH_2$, $-CH_2-CH_2-CH(OH)-CH_2-NH_2$, $-(CH_2)_3-NH_2$, $-(CH_2)_3-NH-CO-NH_2-CH_2CH_2-OH$,
$-CO-CH=CH-CO-O^-$cation$^+$,
$-CO-N^*-CH=CH-N=CH^*$ where the atoms marked with an asterisk (*) are bonded to each other resulting in the formation of a ring,
$-CO-C^*=C[(CH_2)_{n22}-NH_2]-CH=CH-CH=CH^*$ where $n_{22}$ is 1 or 2 and where the atoms marked with an asterisk (*) are bonded to each other resulting in the formation of a ring,
4-$(NHR_{52})$-benzoyl,
$-CO-(CH_2)_{n21}-CO-O-[C_6H_{12}O_6$ sugars],
$-CO-O-CH(CH_2-O-CO-R_{53})_2$ where the $R_{53}$'s are the same or different and are $C_1-C_{18}$,
$-CO-(CH_2)_6-CO-N(CH_3)-CH_2-CH_2-SO_3^-$ cation$^+$,
$-CH_2-O-CO-(CH_2)_{n21}-NR_{51-1}R_{51-2}$ where $n_{21}$, $R_{51-1}$ and $R_{51-2}$ are as defined above,
$-CO-NH-C_6H_4-R_{55}$ where $R_{55}$ is $-H$ or $C_1-C_3$ alkyl, $-NO_2$, $-NR_{51-1}R_{51-2}$ where $R_{51-1}$ and $R_{51-2}$ are as defined above; with the proviso that $R_1$ is not $-CH_2-$ when $R_{17}$, $R_{18}$ and $R_{19}$ are all $-CH_3$; and enantiomers, pharmaceutically acceptable salts, hydrates and solvates thereof.

Additionally disclosed is a method of treating an individual infected with the human immunodeficiency virus (HIV) which comprises administering an effective amount of an anti-AIDS amine of formula (X)

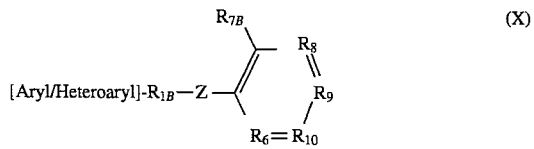

(X)

where
$R_{1B}$ is $-CH_2-$,
$-CO-$,
where
$R_6$ is
$-N=$,
$-CH=$, $R_{7B}$ is $-CO-R_{7B-11}$ where $R_7B_{-11}$ is $-H$,
$C_1-C_6$ alkyl,
$C_2-C_6$ alkenyl containing 1 or 2 double bonds,
$C_2-C_6$ alkynyl containing 1 triple bond,
$-CH_2-\phi$,
$-\phi$ optionally substituted with 1 thru 3
  $-CF_3$,
  $C_1-C_4$ alkyl,
  $-OH$,
  $C_1-C_3$ alkylthio,
  $-O-CO-R_{7B-12}$ where $R_{7B-12}$ is $C_1-C_6$ alkyl or $-\phi$,
  $-F$, $-Cl$, $-Br$,
  $-CO-CF_3$,
  $-NO_2$,
  $-N(R_7B_{-13})(R_{7B-14})$ where $R_{7B-13}$ and $R_{7B-14}$ are the same or different and are $-H$, $C_1-C_3$ alkyl and where $R_{7B-13}$ and $R_{7B-14}$ are taken together with the attached nitrogen atom to form a heterocyclic ring selected from the group consisting of 1-pyrrolidinyl, 1-piperidinyl, 1-piperazinyl or N-morpholinyl,
$-S-R_{7B-1}$ where $R_{7B-1}$ is $C_1-C_6$ alkyl,
$-O-R_{7B-2}$ where $R_{7B-2}$ is $C_1-C_6$ alkyl,
$-C(R_{7B-15})(R_{7B-16})-(R_{7B-17})$ where $R_{7B-15}$ and $R_{7B-16}$ are $-H$, or $C_1-C_3$ alkyl and $R_{7B-17}$ is $C_2-C_5$ alkenyl containing 1 or 2 double bonds or $C_2-C_5$ alkynyl containing 1 triple bond, $R_8$ is $-N=$, $-CH=$ $R_9$ is $-N=$, $-CH=$ $R_{10}$ is $-N=$, $-CH=$ with the proviso that not more than two of $R_6$, $R_8$, $R_9$ and $R_{10}$ are $-N=$; and where Z and [Aryl/Heteroaryl] are as defined above; enantiomers, pharmaceutically acceptable salts, hydrates and solvates thereof.

DETAILED DESCRIPTION OF THE INVENTION

The diaromatic substituted compounds (III) are generally and most often prepared by contacting an aromatic-connector (I) with a substituted linker (II), see CHART A.

The aromatic-connectors (I) are either known to those skilled in the art or can readily be prepared from known compounds by methods well known to those skilled in the art. The aromatic-connector (I) is represented by [Aryl/Heteroaryl]—$R_1$—$X_{13}$ where [Aryl/Heteroaryl] is an aromatic/heteroaromatic substituent (1)–(4), (6)–(11) and (15)–(21), $R_1$ is a connector and $X_{13}$ is a good leaving group, see CHART A. Those [Aryl/Heteroaryl] substituents which when coupled with a substituted linker (II) produce the novel diaromatic substituted compounds (III), the anti-AIDS piperazines (IV) and the indoles (V).

The anti-AIDS piperazines (IV) are particular piperazines previously generically disclosed in International Publication No. WO 88/08424. The indoles (V) are produced by coupling the indole fragment with the appropriate substituted linker (II). The anti-AIDS amines (X) are produced in a manner similar as for the production of the diaromatic substituted compounds (III).

For the diaromatic substituted compounds (III), the indoles (V) and anti-AIDS amines (X), it is preferred that the connector, $R_1$, is $-CO-$. It is preferred that Z be (Z-II) or (Z-III), it is more preferred that Z is (Z-III). It is preferred that $n_{12}$ and $n_{13}$ are both 1 (piperazine). When Z is (Z-IV) or (Z-V) and $n_{12}$ and $n_{13}$ are not the same, two enantiomeric compounds are produced. It is to be understood that the formula (III) for the diaromatic substituted compounds includes both enantiomers. When Z is (Z-I) it is preferred that $R_2$, $R_3$, $R_4$ and $R_5$ are all —H:—H. It is preferred that $R_6$ is either —N= or —CH=; it is more preferred that $R_6$ is —N=. It is preferred that $R_7$ is —N($R_{7-5}$)($R_{7-6}$) where one of $R_{7-5}$ and $R_{7-6}$ is —H and the other of $R_{7-5}$ and $R_{7-6}$ is $C_1$–$C_4$ alkyl; it is more preferred that $C_1$–$C_4$ alkyl is —CH$_2$–CH$_3$, —CH(CH$_3$)$_2$ or —C(CH$_3$)$_3$. It is preferred that $R_8$, $R_9$ and $R_{10}$ are —CH=. It is also preferred that both $R_6$ and $R_8$ are both —N=. It is preferred that [Aryl/Heteroaryl] is a substituent of formulas (2)–(4), (6)–(11) and (15)–(21); it is more preferred that [Aryl/Heteroaryl] is a substituent of formulas (4), (7)–(11), (15) and (21); it is more preferred that [Aryl/Heteroaryl] is a substituent of formulas (4), (7) and (8); it is most preferred that [Aryl/Heteroaryl] is (7). It is preferred that $Q_1$ is —NH—, that $X_6$ is —H, —F, —OCH$_3$, —N(CH$_3$)$_2$ and —CH$_2$—N(CH$_3$)$_2$. It is preferred that the diaromatic substituted compounds (III) is selected from the group of compounds of EXAMPLES 11, 17, 19–25, 27, 29, 31–36, 39, 44, 46–63, 65, 66–76, 81–83, 85–95, 97, 99–106, 108–115, 117–134, 137–144 and 149–154. It is more preferred that the diaromatic substituted compounds (III) be selected from the group of compounds of EXAMPLES 11, 17, 23, 25, 32, 44, 46, 47, 53, 68, 73, 81, 83, 85, 86, 90, 95, 99, 105, 106 and 132.

$X_{13}$ is a good leaving group. When $R_1$ is —(CH$_2$)$_n$— it is preferred that $X_{13}$ is —Cl, and when $R_1$ is —CO— it is preferred that $X_{13}$ is —Cl or —OH where the hydroxy portion is activated by an agent such as 1,1'-carbonyldiimidazole.

The substituted linkers (II) are either known to those skilled in the art (in particular see International Publication No. WO 87/01797, PREPARATION A-1 thru PREPARATION A-50) or can readily be prepared from known compounds by methods well known to those skilled in the art.

The coupling of aromatic-connectors (I) with the substituted linkers (II) to form the diaromatic substituted compounds (III) is a very well known reaction. When Z is the molecular fragment (Z-III) which is piperazine, the substituted linker (II) is a secondary amine and the reaction with the appropriate aromatic-connector (I) produces diaromatic substituted compounds (III) which depending on the nature of $R_1$ is a tertiary amine or an amide. The reaction to produce tertiary amines or amides from cyclic amines such as piperazine is very well known to those skilled in the art and requires no special mention. See International Publication Nos. WO 87/01797 and WO 88/08424.

An alternative method of preparing the diaromatic substituted compounds (III) is to modify a compound which has the basic formula [aryl/heteroaryl]-connector-piperazine-[aryl/heteroaryl]. For example, nitro substituted compounds are not within the scope of the diaromatic substituted compounds (III). PREPARATIONS 22 and 129 and EXAMPLE 52 disclose the reduction of a nitro compound (PREPARATIONS 10, 17 and 35) which has the aromatic-connector (I) portion already coupled with the substituted linker (II), but is not a diaromatic substituted compound (III) because the pyridine moiety is substituted with a nitro group which is outside the scope of the diaromatic substituted compounds (III). Reduction of the nitro group and reductive amination produces a monoalkyl or dialkylamino group of the diaromatic substituted compound (III).

Another method of producing a diaromatic substituted compound (III) in which the connector $R_1$ is —CH$_2$— is by reduction of the —CO— connector of the corresponding diaromatic substituted compound (III), see CHART B and EXAMPLES 7 and 20.

The anti-AIDS piperazines (IV) are the compounds prepared by the procedures of EXAMPLES 1, 3–5, 7, 12, 16, 26, 28, 37, 38, 42, 45, 64, 77, 78, 80, 84, 107, 116, 135, 136 and 145–148. Preferred are the compounds of EXAMPLES 16, 26, 38, 45 and 64. Most preferred is the compound of EXAMPLE 16. It is preferred that the compound of EXAMPLE 16 be in a salt form; the preferred salt is the mesylate.

The diaromatic substituted compounds (III), the anti-AIDS piperazines (IV), the indoles (V) and the anti-AIDS amines (X) are amines and as such form acid addition salts when reacted with acids of sufficient strength to produce the corresponding salts. The salts are preferred over the free amines since they produce compounds which are more water soluble and more crystalline. Pharmaceutically acceptable salts include salts of both inorganic and organic acids. The preferred pharmaceutically acceptable salts include salts of the following acids: methanesulfonic, hydrochloric, hydrobromic, sulfuric, phosphoric, nitric, benzoic, citric, tartaric, fumaric, maleic, p-toluenesulfonic, benzenesulfonic, CH$_3$—(CH$_2$)$_n$—COOH where n is 0 thru 4, HOOC—(CH$_2$)$_n$—COOH where n is as defined above.

While all four types of compounds (III), (IV), (V) and (X) are amines and therefore form acid addition salts, some of the variable substituents are acids and as such form base addition salts when reacted with bases of sufficient strength. The pharmaceutically acceptable salts include both inorganic and organic bases. The pharmaceutically salts are preferred over the free acids since they produce compounds which are more water soluble and more crystalline. The preferred pharmaceutically acceptable salts include salts of the following bases, for example, hydroxide, ammonia, tromethamine (THAM), 2-amino-2-(hydroxymethyl)-1,3-propanediol. Suitable cations include, for example, sodium, potassium, calcium and magnesium.

The diaromatic substituted compounds (III), the anti-AIDS piperazines (IV) and the indoles (V) are useful as inhibitors of viral reverse transcriptase, an enzyme necessary for human immunodeficiency virus replication and therefore would be useful in the treatment of such diseases as AIDS.

The term human retrovirus (HRV) indicates human immunodeficiency virus type I, or strains thereof apparent to one skilled in the art, which belong to the same viral families and which create similar physiological effects in humans as various human retroviruses.

Patients to be treated would include those individuals (1) infected with one or more than one strain of a human retrovirus as determined by the presence of either measurable viral antibody or antigen in the serum and (2) having either a symptomatic AIDS defining infection such as (a) disseminated histoplasmosis, (b) isopsoriasis, (c) bronchial and pulmonary candidiasis including pneumocystic pneumonia (d) non-Hodgkin's lymphoma or (e) Kaposi's sarcoma and being less than sixty years old; or having an absolute CD4 lymphocyte count of less than 200/m$^3$ in the peripheral blood. The diaromatic substituted compounds (III), the anti-AIDS piperazines (IV) and the indoles (V) can be given orally. Suitable dosage forms include tablets, capsules, suspensions, solutions and elixirs. An effective amount is from about 0.1 to about 500 mg/kg/day. A typical unit dose for a 70 kg human would be from about 10 mg to about 2000 mg, preferably about 100 mg to about 1000 mg taken one to six times per day.

The exact dosage and frequency of administration depends on the particular diaromatic substituted compounds (III), the anti-AIDS piperazines (IV) and the indoles (V) used, the particular condition being treated, the severity of the condition being treated, the age, weight, general physical condition of the particular patient, other medication the individual may be taking as is well known to those skilled in the art and can be more accurately determined by measuring the blood level or concentration of the diaromatic substituted compounds (III), the anti-AIDS piperazines (IV) and the indoles (V) in the patient's blood and/or the patient's response to the particular condition being treated.

Patients who are HIV positive but asymptomatic would typically be treated with lower oral doses (about 0.2 to about 100 mg/kg/day. ARC (AIDS-related complex) and AIDS patients would typically be treated with higher oral doses (about 1 to about 500 mg/kg/day).

The diaromatic substituted piperazines (III), the anti-AIDS piperazines (IV) and the indoles (V) of this invention can be used in conjunction with other antiviral agents such as AZT.

The utility of the diaromatic substituted piperazines (III), the anti-AIDS piperazines (IV) and the indoles (V) of this invention can be determined by their ability to inhibit viral reverse transcriptase, an enzyme essential for human immunodeficiency virus replication. This enzyme has characteristics which differentiate it from other known cellular polymerases and it is a unique enzyme which is not found in uninfected cells. Viral reverse transcriptase is found in extracts from bacterial clones prepared according to the procedure described in AIDS Virus Reverse Transcriptase defined by high level expression in *Escherichia coli*, EMBO J. 6:3133–3137 (1987). Inhibition of this enzyme is determined in a cell free assay which measures the level of radioactive precursors incorporated into DNA. Extracts prepared according to the procedure of Science, 1125–1129 (1981) are incubated in a mixture of inhibitor, 20 mM dithiothreitol, 60 mM sodium chloride, 0.05% NP-40, 10 mM magnesium chloride, 50 mM Tris pH 8.3, 10 µM [$^{35}$S]-labeled deoxynuleoside-5'-triphosphate, 10 µg/ml RNA template (poly rC or poly rG) and 5 µg/ml DNA primer (oligo dG or oligo dT) for 30 minutes at 37° C. Incorporation of radio-labeled percursor is determined by spotting aliquots of the reaction mixture on DE81 paper, washing the papers to remove unincorporated percursor, drying and determining counts. The results ($IC_{50}$ means the concentration, in µM of drug, required to inhibit the reverse transcriptase activity to the extent of 50%) of various assay(s) are combined and reported as % inhibition and $IC_{50}$ (calculated).

The utility of this invention is further demonstrated by the ability of the diaromatic substituted compounds (III), the anti-AIDS piperazines (IV) and the indoles (V) to inhibit HIV-induced syncytia formation in a tissue culture assay using MT-2 cells infected with HIV-1. This test is described in Quantitative Infectivity Assay for HIV-1 and -2., Nature 332: 469–470, 1988 as well as in AIDS RESEARCH AND HUMAN RETROVIRUSES, Vol. 4, No. 6, pages 449–455 (1988), Mary Ann Liebent, Inc., Publishers; in an article entitled "Nucleotide Dimers Suppress HIV Expression In VITRO". The results ($IC_{50}$ means the concentration, in µM of drug, required to inhibit syncytia formation to the extent of 50%) of various assay(s) are combined and reported as % inhibition and $IC_{50}$ (calculated). The known commercial compound, AZT, exhibited anti-HIV potency in this assay with 100 percent and 50 percent reduction in syncytia formation at concentrations of approximately 1 µM, respectively.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3-C(=Z_1)H$. Groups $R_i$ and $R_j$ would represent monovalent variable substituents if attached to the formula $CH_3-CH_2-C(R_i)(R_j)H$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom.

Chemical formulas or portions thereof drawn in a linear fashion represent atoms in a linear chain. The symbol "—" in general represents a bond between two atoms in the chain. Thus $CH_3-O-CH_2-CH(R_i)-CH_3$ represents a 2-substituted-1-methoxypropane compound. In a similar fashion, the symbol "=" represents a double bond, e.g., $CH_2=C(R_i)-O-CH_3$, and the symbol "≡" represents a triple bond, e.g., $HC≡C-CH(R_i)-CH_2-CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by $N*=C(CH_3)-CH=CCl-CH=C*H$ with the convention that the atoms marked with an asterisk (*) are bonded to each other resulting in the formation of a ring. Likewise, the cyclic molecular fragment, 4-(ethyl)-1-piperazinyl can be represented by $-N*-(CH_2)_2-N(C_2H_5)-CH_2-C*H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, $-C(X_1)(X_2)-$ the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha (α) configuration and is identified by a broken, dashed or dotted line attachment to the carbon atom, i.e., by the symbol " - - - " or " . . . ". The corresponding substituent attached "above" ($X_2$) the other ($X_1$) is identified as being in the beta (β) configuration and is indicated by an unbroken line attachment to the carbon atom.

When a variable substituent is bivalent, the valences may be taken together or separately or both in the definition of the variable. For example, a variable $R_i$ attached to a carbon atom as $-C(=R_i)-$ might be bivalent and be defined as oxo or keto (thus forming a carbonyl group (—CO—) or as two separately attached monovalent variable substituents $\alpha-R_{i-j}$ and $\beta-R_{i-k}$. When a bivalent variable, $R_i$, is defined to consist of two monovalent variable substituents, the convention used to define the bivalent variable is of the form "$\alpha-R_{i-j}:\beta-R_{i-k}$" or some variant thereof. In such a case both $\alpha-R_{i-j}$ and $\beta-R_{i-k}$ are attached to the carbon atom to give $-C(\alpha-R_{i-j})(\beta-R_{i-k})-$. For example, when the bivalent variable $R_6$, $-C(=R_6)-$ is defined to consist of two monovalent variable substituents, the two monovalent variable substituents are $\alpha-R_{6-1}:\beta-R_{6-2}$, $\alpha-R_{6-9}:\beta-R_{6-10}$, etc, giving $-C(\alpha-R_{6-1})(\beta-R_{6-2})-$, .... $-C(\alpha-R_{6-9})(\beta-R_{6-10})-$, etc. Likewise, for the bivalent variable $R_{11}$, $-C(=R_{11})-$, two monovalent variable substituents are $\alpha-R_{11-1}:\beta-R_{11-2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula $-C_1(R_i)H-C_2(R_j)H-$ ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form $-CH_2-CH_2-O-CO-$. . ." means a lactone in which the carbonyl is bonded to $C_2$. However, when designated ". . . $R_j$ and $R_i$ are taken together to form $-CO-O-CH_2-CH_2-$ the convention means a lactone in which the carbonyl is bonded to $C_1$.

The carbon atom content of variable substituents is indicated in one of two ways. The first method uses a prefix to the entire name of the variable such as "$C_1-C_4$", where both "1" and "4" are integers representing the minimum and maximum number of carbon atoms in the variable. The prefix is separated from the variable by a space. For example, "$C_1-C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2-C_4$ alkoxycarbonyl describes a group $CH_3-(CH_2)_n-O-CO-$ where n is zero, one or two. By the second method the carbon atom content of only each portion of the definition is indicated separately by enclosing the "$C_i-C_j$" designation in parentheses and placing it immediately (no intervening space) before the portion of the definition being defined. By this optional convention $(C_1-C_3)$alkoxycarbonyl has the same meaning as $C_2-C_4$ alkoxycarbonyl because the "$C_1-C_3$" refers only to the carbon atom content of the alkoxy group. Similarly while both $C_2-C_6$ alkoxyalkyl and $(C_1-C_3)$alkoxy$(C_1-C_3)$alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.

TLC refers to thin-layer chromatography.

THF refers to tetrahydrofuran.

Saline refers to an aqueous saturated sodium chloride solution.

NMR refers to nuclear (proton) magnetic resonance spectroscopy, chemical shifts are reported in ppm ($\delta$) downfield from tetramethylsilane.

IR refers to infrared spectroscopy.

CMR refers to C-13 magnetic resonance spectroscopy, chemical shifts are reported in ppm ($\delta$) downfield from TMS.

EDC refers to 1-ethyl-3-(3-dimethylaminopropyl)carbodiimide.

—$\phi$ refers to phenyl ($C_6H_5$).

MS refers to mass spectrometry expressed as m/e or mass/charge unit. $[M+H]^+$ refers to the positive ion of a parent plus a hydrogen atom. EI refers to electron impact. CI refers to chemical ionization. FAB refers to fast atom bombardment.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pyridinyl refers to the pyridyl radical as defined by IUPAC nomenclature. For example, 2-pyridyl (pyridine ring substituted in the 2-position).

The compounds of this invention are named (when possible) by the following method: first the [aryl/heteroaryl] moiety, next the aryl/heteroaryl portion of the substituted linker (II) and last the linker (Z) itself, however a few were named by other methods for simplicty and convenience. The names of the radicals within each group follow the IUPAC convention.

When solvent pairs are used, the ratios of solvents used are volume/volume (v/v).

HIV refers to HIV-1.

Treatment refers to inhibition of the HIV virus and will differ depending on the infected individual. For individuals who are HIV positive (infected) but who are asymptomatic, the diaromatic substituted compounds (III), the anti-AIDS piperazines (IV) and the indoles (V) will delay, or prevent, the onset of symptoms. For individuals who are HIV positive, symptomatic and are pre-AIDS or ARC patients, the diaromatic substituted compounds (III), the anti-AIDS piperazines (IV) and the indoles (V) will delay, or prevent, the onset of "full blown AIDS". For individuals who have "full blown AIDS", the diaromatic substituted compounds (III), the anti-AIDS piperazines (IV) and the indoles (V) will extend survival time of these individuals.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

4-Bromo-2,6-dimethylanisole

Bromine (31.15 g) is added dropwise to an ice-cold solution of 2,6-dimethylanisole (18.96 g) in chloroform (300 ml). After the addition is complete, the reaction is allowed to stir at ambient temperature overnight. The chloroform solution is washed with cold water (2×), once with an aqueous saturated solution of sodium bicarbonate, and then again with water. The chloroform extract is dried over sodium sulfate and concentrated under reduced pressure a liquid, which is distilled to give the title compound, bp. 55°/1.5 mm mercury.

PREPARATION 2

3,5-Dimethyl-4-methoxybenzoic acid ethyl ester

A solution of 4-bromo-2,6-dimethylanisole (PREPARATION 1, 12.98 g) in tetrahydrofuran (40 ml) is added drop by drop to a mixture of magnesium turnings (1.87 g) in tetrahydrofuran (5 ml). The Grignard reaction is initiated with iodine crystals. After the addition is complete, the mixture is refluxed for 2 hours. The Grignard reagent is cooled to about 10° and then a solution of ethyl chloroformate (7.5 ml) in tetrahydrofuran (40 ml) is added in a 2 minute period. The mixture is stirred for 45 minutes at ice-water temperature and then at 20°–25° for 2 hours. The reaction is quenched with a saturated solution of ammonium chloride and diluted with ether. The phases are separated, the organic phase is washed with water and then with saline, dried over sodium sulfate, and concentrated under reduced pressure to give the title compound.

PREPARATION 3

3,5-Dimethyl-4-methoxybenzoic acid (I)

A mixture of 3,5-dimethyl-4-methoxybenzoic acid ethyl ester (PREPARATION 2, 10.5 g) and aqueous sodium hydroxide (20%, 100 ml) is refluxed for 18 hours. The solution is cooled and acidified with hydrochloric acid (12N, pH 2). The acidified solution is extracted with chloroform (3×). The combined extracts are dried over sodium sulfate and concentrated under reduced pressure to give a solid which is recrystallized from ether/pet ether mixture to give the title compound, mp 189°–191°.

PREPARATION 4

3,5-Dimethyl-4-methoxybenzyl chloride (I)

Hydrogen chloride gas is bubbled into a solution of formaldehyde (37%), glacial acetic acid (100 ml), and 2,6-dimethylanisole (21.8 g). After a short period of time, an exothermic reaction occurs and the reaction temperature rises to about 40°. The reaction mixture is cooled to about 20° with an ice bath. Hydrogen chloride gas is continually bubbled through the reaction solution for 5.5 hours. A gas chromatogram indicates the starting material is consumed. The hydrogen chloride bubbling is discontinued and the solution is then heated on a steam bath for 15 minutes. After cooling to 20°–25°, the reaction is diluted with water and ether. The phases are separated and the aqueous phase is extracted a second time with ether. The combined ether extracts are washed with water (3×) and then with saline, dried over sodium sulfate, and concentrated under reduced pressure to a liquid, which is distillation under a house vacuum to give the title compound, bp. 145°–150°.

PREPARATION 5

3,5-Dimethyl-4-hydroxybenzyl chloride (I)

3,5-Dimethyl-4-methoxybenzyl chloride (I, PREPARATION 4, 1.8 g) is added to a solution of boron tribromide (1.5 m) in dichloromethane (70 ml) at 78°. The solution is allowed gradually to warm to 20°–25° overnight. The reaction is poured into an aqueous sodium bicarbonate solution, and the phases are separated. The dichloromethane phase is washed once with water and then with concentrated hydrochloric acid. The dried (sodium sulfate) organic phase is concentrated under reduced pressure to give the title compound.

PREPARATION 6

1-[1,1-Dimethylethoxycarbonyl]-4-[3-(propylamino)-2-pyridinyl]piperazine

Sodium cyanoborohydride (0.31 g) is added to a cold solution of 1-[1,1-dimethylethoxycarbonyl]-4-[3-amino-2-pyridinyl]piperazine (International Publication No. WO 88/08424, 2.8 g), propional (0.87 g), and methanol (15 ml). After the exotherm has subsided, the reaction is stirred at 20°–25° overnight. The reaction is acidified (pH 2) with aqueous hydrochloride and then diluted with dichloromethane. The pH is adjusted with aqueous ammonium hydroxide (pH 8), and the phases are separated. The organic phase is dried over sodium sulfate, and concentrated under reduced pressure to a crude product which is dissolved in diethyl ether and allowed to crystallize at −5°. The solid is identified as starting material. The mother liquor is concentrated in vacuo to give the title compound.

PREPARATION 7

1-[3-(Propylamino)-2-pyridinyl]piperazine (II)

Trifluoroacetic acid (4 ml) is added to a solution of crude 1-[1,1-dimethylethoxycarbonyl]-4-[3-propylamino)-2-pyridinyl]piperazine (PREPARATION 6, 1.2 g) in dichloromethane (15 ml) chilled to −78°. The coolant is removed and the reaction is allowed to warm to 20°–25° for 3 hours. The solvents are removed in vacuo and the residue is redissolved in dichloromethane and aqueous saturated potassium carbonate. The phases are separated. The organic phase is washed with water, dried over sodium sulfate, and concentrated to the title compound.

PREPARATION 8

1-[1,1-Dimethylethoxycarbonyl]-4-[3-(1-methylethylamino)-2-pyridinyl]piperazine

1-[1,1-Dimethylethoxycarbonyl]-4-[3-amino-2-pyridinyl]piperazine (International Publication 88/08424, 2.0 g) is dissolved in 35 ml of methanol and acetone (0.48 g) is added. The reaction is cooled to 0° and acetic acid (to pH 4.0) is added. The reaction is stirred 15 min at 0° and then sodium cyanoborohydride (0.50 g) is added. The reaction is allowed to warm slowly to 20°–25° and followed by TLC until completion. Additional acetic acid, sodium cyanoborohydride and acetone are sometimes necessary to force the reaction to completion. The reaction is diluted with chloroform (100 ml), washed with saturated aqueous sodium bicarbonate (50 ml), saline (75 ml), dried over anhydrous sodium sulfate and concentrated in vacuo. Purification by flash column chromatography (75 g silica gel, 4:1 hexane/ethyl acetate) affords the title compound, NMR (300 MHz, CDCl$_3$) 7.67, 6.91, 4.15, 3.57, 3.00, 1.48 and 1.23δ.

PREPARATION 9

1-[3-(1-Methylethylamino)-2-pyridinyl]piperazine (II)

1-[1,1-Dimethylethoxycarbonyl]-4-[3-(1-methylethylamino)-2-pyridinyl]piperazine (PREPARATION 8) is dissolved in methylene chloride (56 ml) and cooled to 0°. Then trifluoroacetic acid is added dropwise. The reaction is warmed to 20°–25° and additional trifluoroacetic acid is added (26.6 g). When the reaction is complete by TLC, it is poured into 200 ml of water and ice, basified to pH 12 with 2N aqueous sodium hydroxide, and extracted with 10% tetrahydrofuran/chloroform (2 l) followed by 10% methanol/chloroform (1 l). The organic layers are dried over anhydrous sodium sulfate, concentrated in vacuo, and used without further purification, NMR (300 MHz, CDCl$_3$) 7.65, 6.85, 6.76, 4.16, 3.50, 2.98 and 1.20δ.

PREPARATION 10

1-[Indolyl-2-carbonyl]-4-(3-nitro-2-pyridinyl)piperazine 1-(3-Nitro-2-pyridinyl)piperazine (2.58 g) is dissolved in methylene chloride (25 ml). Pyridine (1.031 g) is added and the reaction is cooled to 0°. Indole-2-carbonyl chloride (2.23 g) in methylene chloride (6 ml) is added dropwise. The reaction is stirred for 30 minutes at 0°, diluted with methylene chloride (50 ml), washed with saturated aqueous sodium bicarbonate (60 ml), saline (70 ml), dried over anhydrous sodium sulfate and concentrated under reduced pressure. The crude residue is recrystallized from methanol/toluene (200 ml, 10/90) to give the title compound, mp 205°–207°.

PREPARATION 11

1-(2-Nitrophenyl)piperazine

Piperazine (24.46 g) is dissolved in acetonitrile (200 ml) and anhydrous potassium carbonate (10.47 g) is added. Then 2-chloronitrobenzene (10.0 g) is added dropwise. After stirring 1 hr at 20°, the reaction mixture is diluted with methylene chloride, washed with water, and saturated aqueous potassium carbonate. After drying over anhydrous sodium sulfate, the reaction mixture is concentrated under reduced pressure to give the title compound, NMR (300 MHz, CDCl$_3$) 7.75, 7.49, 7.14, 7.04, 3.03 and 1.93δ.

PREPARATION 12

1-[1,1-Dimethylethoxycarbonyl]-4-(2-nitrophenyl)piperazine

Di-t-butyldicarbonate (5.24 g) is added to a 0° solution of 1-(2-nitrophenyl)piperazine (PREPARATION 11, 5.0 g) and triethylamine (3.7 ml) in methylene chloride (48 ml). The reaction is warmed to 20°–25° after 20 min and stired 3.5 hr. Then the reaction is diluted with methylene chloride, washed with saturated aqueous sodium bicarbonate, saline, dried over anhydrous sodium sulfate and concentrated under reduced pressure to give the title compound.

PREPARATION 13

1-[1,1-Dimethylethoxycarbonyl]-4-(2-aminophenyl)piperazine

1-[1,1-Dimethylethoxycarbonyl]-4-(2-nitrophenyl)piperazine (PREPARATION 12, 7.61 g) is dissolved in ethanol (150 ml). Palladium on carbon (10%, 0.75 g) is added and the reaction is hydrogenated at 45 psi for 6 hr. The mixture is filtered thru celite and concentrated under reduced pressure to give the title compound.

PREPARATION 14

1-[1,1-Dimethylethoxycarbonyl]-4-[2-(ethylamino)phenyl]piperazine

Sodium cyanoborohydride (1.6 g) is added to a 0° solution of 1-[1,1-dimethylethoxycarbonyl]-4-(2-aminophenyl)piperazine (PREPARATION 13, 6.52 g) and acetaldehyde (1.48 ml) dissolved in methanol (65 ml). After 3 hr the reaction mixture is partially concentrated under reduced pressure. Then it is diluted with chloroform, washed with saturated aqueous sodium bicarbonate, saline, dried over anhydrous sodium sulfate and concentrated under reduced pressure to give the title compound, R$_f$=0.62 (ethyl acetate/hexane, 1/1), NMR (300 MHz, CDCl$_3$) 7.04, 6.95, 6.66, 4.59, 3.70–3.50, 3.15, 2.82, 1.49 and 1.28δ.

PREPARATION 15

1-[2-(Ethylamino)phenyl]piperazine (II)

Following the general procedure of PREPARATION 7 and making non-critical variations but using 1-[1,1-dimethylethoxycarbonyl]-4-(2-ethylaminophenyl)piperazine (PREPARATION 14, 8.61 g), the title compounds is obtained, R$_f$=0.2 (methanol/triethylamine/chloroform, 1/1/98).

PREPARATION 16

5-Fluoroindole-2-carbonyl chloride (I)

5-Fluoroindole-2-carboxylic acid is dissolved in oxalylchloride and stirred 24 hr at 20°–25° in the dark. The reaction mixture is concentrated under reduced pressure to give the title compound.

PREPARATION 17

1-[5-Fluoroindolyl-2-carbonyl]-4-[(3-nitro)-2-pyridinyl]piperazine

Following the general procedure of PREPARATION 10 and making non-critical variations but starting with 5-fluoroindole-2-carbonyl chloride (PREPARATION 16), the title compound is obtained, NMR (300 MHz, CDCl$_3$) 9.41, 7.80, 7.35, 7.27, 7.05, 7.01, 6.88, 6.77, 4.08, 3.83 and 3.24δ.

PREPARATION 19

Ethyl 5-methoxy-4,5,7-trimethylindole-2-carboxylate

A solution of sodium nitrite (1.91 g) in water (4.4 ml) is added (below the surface) to a cold (−10°) thick slurry of 2,3,5-trimethyl-4-methoxyaniline [J. Amer. Chem. Soc., 70 2656 (1948)] in ethanol (10 ml), water (54 ml) and concentrated hydrochloric acid (9.3 ml). The mixture is stirred for 30 min as the temperature rises to −1°, then the solution of the diazonium salt is poured into a vigorously stirred mixture of ethyl methylacetoacetate (3.68 g) in ethanol (24 ml) containing potassium hydroxide (45%, 6 ml) and ice (40 g). The mixture is allowed to warm to 20°–25° with continued stirring for 1 hr, then is extracted with toluene. The toluene extracts are dried (potassium carbonate) and concentrated to give an oil. A solution of the oil in ethanol (20 ml) is stirred while hydrogen chloride rapidly with an exotherm to 60°. The mixture is cooled and saturated with hydrogen chloride at 45°, then is stored overnight at 5°. The precipitate is collected and washed several times with cold ethanol. The solid is partitioned between ethyl acetate and aqueous bicarbonate, the phases separated, the organic phases dried and concentrated. The concentrate is crystallized from acetone/hexane to give the title compound, mp 182°–183°.

PREPARATION 20

5-Methoxy-4,6,7-trimethylindole-2-carboxylic acid (I)

A solution of ethyl 5-methoxy-4,5,7 trimethylindole-2-carboxylate (PREPARATION 19, 1.04 g) in ethanol (30 ml) containing potassium hydroxide (45%, 2.5 ml) is heated under reflux for 1.5 hr. The mixture is acidified with acetic acid (2 ml) and concentrated under reduced pressure. The residue is mixed with water (200 ml) and filtered. The filter cake is washed with water and dried to give the title compound.

PREPARATION 21

1-[3-(1,1-Dimethylethylamino)-2-pyridinyl]piperazine

Isobutylene (10 ml) is condensed into a solution of 1-[1,1-dimethylethoxycarbonyl]-4-[3-amino-2-pyridinyl]piperazine (International Publication No. WO 88/08424, 200 mg) in methylene chloride (10 ml) at −70°. Phosphoric acid (85%, 50 μl) is added and the mixture stirred for 60 minutes. Boron trifluoride etherate (200 μl) is added dropwise and the resulting suspension is stirred 8 hours at reflux and overnight at 20°–25° allowing the isobutylene to evaporate. The suspension is diluted with water and ammonium hydroxide is added until basic to pH paper and then extracted with methylene chloride (3×). The combined extracts are dried over anhydrous potassium carbonate, filtered, and concentrated under reduced pressure to a liquid which is flash chromatographed (silica gel, 230–400 mesh), eluting with methanol/chloroform (3/20). The appropriate fractions are pooled and concentrated to give an oil. The NMR, CMR, IR, and MS (m/e) M+234 support the title compound.

PREPARATION 22

1-[Indolyl-2-carbonyl]-4-[3-amino-2-pyridinyl]piperazine

1-[Indolyl-2-carbonyl]-4-(3-nitro-2-pyridinyl)piperazine (PREPARATION 10, 3.67 g) is suspended in dioxane (80 ml) and aqueous titanium trichloride (20%, 48.3 ml) is added in one portion. The reaction is stirred for 30 minutes at 20°–25°, diluted with aqueous sodium hydroxide (2N, 100 ml), extracted with methylene chloride (3×100 ml), dried over anhydrous sodium sulfate and concentrated under reduced pressure. Purification by flash column chromatography (100 g silica gel) eluting with methanol/chloroform (3/97), pooling the appropriate fractions and concentrating them gives the title compound, mp 191°–192°.

PREPARATION 23

1-[1,1-Dimethylethoxycarbonyl]-4-[4-chloro-5-nitro-6-pyrimidyl]piperazine

A solution of 1-[1,1-dimethylethoxycarbonyl]piperazine (1.88 g) in dichloromethane (30 ml) is added drop by drop over 1.5 hr to a solution of 4,6-dichloro-5-nitropyrimidine (1.94 g) and triethylamine (1.32 g) in dichloromethane (170 ml) at −78°. After stirring an additional hr at −78°, the reaction is diluted with aqueous sodium bicarbonate (10%). The phases are separated, the organic phase is concentrated to a liquid which solidified on standing at 20°–25°. The solid is dissolved in chloroform and flash chromatographed on silica gel eluting with methanol/chloroform (1/99), pooling and concentrating the appropriate fractions gives the title compound, Anal. Calc for C$_{13}$H$_{18}$N$_5$ClO$_4$; MW=343.77: C,45.42; H,5.28; N,20.37; Cl,10.31. Found: C,45.52; H,5.40; N,20.34; Cl,10.36.

PREPARATION 24

2-Chloro-3-(1-methylethylamino)pyrazine

A solution of 2,3-dichloropyrazine (2.0 g) and isopropylamine (2.3 g) in toluene (8 ml) is refluxed for 40 hr. The mixture is cooled and filtered to remove isopropylamine hydrochloride. The filtrate is concentrated in vacuo to a residue which is diluted with an aqueous sodium hydroxide solution (10%) and dichloromethane. The phases are separated. The dichloromethane phase is washed with saline, dried over sodium sulfate, and concentrated to give the title compound, NMR (CDCl$_3$) 1.28, 4.21, 5.02, 7.54 and 7.94δ.

PREPARATION 25

1-[2-(1-Methylethylamino)-3-pyrazinyl]piperazine (II)

A solution of 2-chloro-3-(1-methylethylamino)pyrazine (PREPARATION 24, 1.6 g) and piperazine (4.3 g) in xylene (10 ml) is refluxed for 26 hr. The mixture is cooled to 0$_o$ and diluted with concentrated hydrochloric acid (8 ml). The xylene is decanted and ether is added and also decanted from the salts. The salts are diluted with excess aqueous sodium hydroxide (5%) and dichloromethane. The phases are separated. The aqueous phase is extracted three more times with dichloromethane. The combined organic extracts are dried over sodium sulfate and concentrated to give a liquid mixture which is flash chromatographed on silica gel eluting with methanol/chloroform (5/95). The appropriate fractions are pooled and concentrated to give the title compound, NMR (CDCl$_3$) 1.27, 1.83, 3.04, 4.12, 4.78, 7.49 and 7.72δ.

PREPARATION 26

2-Chloro-3-(1,1-dimethylethylamino)pyrazine

Following the general procedure of PREPARATION 24 and making non-critical variations but starting with 2,3-dichloropyrazine (2.0 g), the title compound is obtained, NMR (CDCl$_3$) 1.48, 5.24, 7.51 and 7.91δ.

PREPARATION 27

1-[3-(1,1-Dimethylethylamino)-2-pyrazinyl]piperazine (II)

Following the general procedure of PREPARATION 25 and making non-critical variations but starting with 2-chloro-3-(1,1-dimethylethylamino)pyrazine (PREPARATION 26, 0.95 g) and piperazine, the title compound is obtained, NMR (CDCl$_3$) 1.47, 1.70, 2.99, 5.02, 7.46 and 7.69δ.

PREPARATION 28

1-[1,1-Dimethylethoxycarbonyl]-4-[5-amino-6-pyrimidinyl]piperazine

A mixture of 1-[1,1-dimethylethoxycarbonyl]-4-[4-chloro-5-nitro-6-pyrimidyl]piperazine (PREPARATION 23, 0.56 g) and triethylamine (0.3 ml) and palladium on carbon (5%, 0.13 g) in ethanol (100 ml) is charged with hydrogen gas (30 psi). After the theoretical amount of hydrogen gas is consumed, the catalyst is removed under reduced pressure. The filtrate is concentrated under reduced pressure to a foam which is diluted with an aqueous saturated solution of potassium carbonate and dichloromethane. The phases are separated and the organic phase is dried over sodium sulfate and concentrated to give to give the title compound, NMR (CDCl$_3$) 1.49, 3.49, 3.29, 3.56, 7.98, and 8.39δ.

PREPARATION 29

1-[1,1-Dimethylethoxycarbonyl]-4-[5-(1-methylethylamino)-6-pyrimidinyl]piperazine A solution of sodium cyanoborohydride (0.13 g) in methanol (4 ml) is added to a mixture of 1-[1,1-dimethylethoxycarbonyl]-4-[5-amino-6-pyrimidinyl]piperazine (PREPARATION 28, 0.44 g), acetone (3 ml), and glacial acetic acid (0.4 ml) in methanol (7 ml) at 0°. The mixture is stirred at 20°–25° for 72 h. The reaction is diluted with an aqueous sodium hydroxide solution (10%) and dichloromethane. The phases are separated and the organic phase is washed with water and the concentrated to a colorless liquid which is flash chromatographed on silica gel eluting with methanol/chloroform (1/99). The appropriate fractions are pooled and concentrated to give the title compound, NMR (CDCl$_3$) 1.26, 1.49, 3.2, 3.44, 3.5–3.62, 7.89 and 8.33δ.

PREPARATION 30

1-[5-(1-Methylethylamino)-4-pyrimidinyl]piperazine (II)

Trifluoroacetic acid (5 ml) is added to a solution of 1-[1,1-dimethylethoxy-carbonyl]-4-[5-(1-methylethylamino)-4-pyrimidinyl]piperazine (PREPARATION 29, 0.37 g) in dichloromethane (20 ml) at −78°. The reaction is allowed to warm to 20°–25° overnight, and then diluted with excess aqueous sodium hydroxide solution (10%). The phases are separated. The aqueous phase is extracted twice again with dichloromethane. The combined organic extracts are washed with saline, dried over sodium sulfate, and concentrated under reduced pressure to give the title compound, NMR (CDCl$_3$) 1.25, 1.7, 3.01, 3.21, 3.45, 3.5, 7.86 and 8.34δ.

PREPARATION 31

3,5-Dichloro-4-(1-methylethylamino)pyridazine

A solution of 3,4,5-trichloropyridazine (9.2 g) and isopropylamine (16.5 g) in toluene (25 ml) is refluxed for 18 hr. Excess isopropylamine is removed by atmospheric distillation. The residual solution is cooled and diluted with dichloromethane and aqueous sodium hydroxide solution (5%). The phases are separated. The organic phase is washed with water and then with saline. The organic phase is dried over sodium sulfate and concentrated under reduced pressure to give a liquid which contaimes a mixture of isomeric products. The isomers are separated by flash chromatography on silica gel eluting with ether/hexane (30/70). The appropriate fractions are pooled and concentrated to give the desired isomer, NMR (CDCl$_3$) 1.33, 4.59, 4.87 and 8.60δ; CMR (CDCl$_3$) 24.2, 46.4, 117.1, 139.3, 145.5 and 151.3δ.

Further elution gives 3,4-dichloro-5-(1-methylethylamino)pyridazine which is recrystallized from ether hexane, NMR (CDCl$_3$) 1.35, 3.87, 4.80, and 8.55δ; CMR (CDCl$_3$) 22.6, 44.7, 116.5, 136.3, 142.5 and 153.4δ.

PREPARATION 32

1-[5-Chloro-4-(1-methylethyl)amino-3-pyridazinyl]piperazine

A mixture of 3,5-dichloro-4-(1-methylethyl)aminopyridazine (PREPARATION 31, 1.77 g) and piperazine (2.96 g) in xylene (18 ml) is refluxed for 40 hr. The mixture is cooled and then treated with concentrated hydrochloric acid (8 ml). After further cooling, a precipitate forms and the organic liquid is separated. The aqueous phase is diluted with an excess of a solution of aqueous sodium hydroxide (10%) and then is extracted with chloroform (3×). The combined organic extracts are washed with water, then saline, dried over sodium sulfate, and concentrated to an oil. The crude product is flash chromatographed on silica gel eluting with methanol. The appropriate fractions are pooled and concentrated to give the title compound, NMR (CDCl$_3$) 1.20, 3.04, 3.18, 4.46, 4.73 and 8.50δ; CMR (CDCl$_3$) 24.0, 44.3, 45.9, 50.2, 118.2, 135.8, 148.3 and 155.4δ.

PREPARATION 33

1-[4-(1-Methylethyl)amino-3-pyridazinyl]piperazine (II)

Following the general procedure of PREPARATION 28 and making non-critical variations but starting with 1-[5-chloro-4-(1-methylethyl)amino-3-pyridazinyl]piperazine (PREPARATION 32, 1.7 g) and triethylamine (0.81 g), the title compound is obtained, NMR (CDCl$_3$) 1.28, 2.06, 3.05, 3.11, 3.59, 4.75, 6.39, and 8.49δ; CMR (CDCl$_3$) 22.2, 43.2, 46.2, 50.6, 103.7, 138.7, 148.4 and 154.5δ.

PREPARATION 34

N,N'-Dimethyl-N-(3-nitro-2-pyridinyl)ethylenediamine

To a solution of N,N'-dimethylethylenediamine (3.2 ml) and potassium carbonate (830 mg) in acetonitrile (15 ml) stirred at 20°–25° under a nitrogen atmosphere is added a solution of 2-chloro-3-nitropyridine (500 mg) in acetonitrile (10 ml) over one hour. The mixture is concentrated under reduced pressure and partitioned between methylene chloride (75 ml) and water (25 ml). The phases are separated and the aqueous phase is extracted with methylene chloride (25 ml) and the total organics are dried with saline and sodium sulfate. Concentration under reduced pressure gives the title compound, NMR (CDCl$_3$) 8.29, 8.10, 6.69, 3.85, 2.90, 2.88 and 2.46δ.

PREPARATION 35

N,N'-Dimethyl-N-(indolyl-2-carbonyl)-N'-(3-nitro-2-pyridinyl)ethylenediamine 1,1'-carbonyldiimidazole (551 mg) is added to a solution of indole-2-carboxylic acid (516 mg) in dry tetrahydrofuran (8 ml). The mixture is stirred one hour at 20°–25° and N,N'-dimethyl-N-(3-nitro-2-pyridinyl)ethylenediamine (PREPARATION 34, 674 mg) is added as a solution in tetrahydrofuran (4 ml) via a canula, rinsing in with tetrahydrofuran (2 ml). The mixture is stirred 1 hr and concentrated to a gum, diluted with methylene chloride (100 ml), washed with water and saline and dried over sodium sulfate. Removal of solvent under reduced pressure gives a solid which is recrystallized from methylene chloride/ethyl ether to give the title compound, mp 172.5°–173°.

PREPARATION 36

2-(N-Methyl-N-(3-nitro-2-pyridinyl)amino)ethanol 2-(Methylamino)ethanol (3.04 ml) is added to a mixture of 2-chloro-3-nitropyridine (3.00 g) and of potassium carbonate (5.22 g) in acetonitrile (90 ml) at 0°. The mixture is stirred for 2.5 hr at 20°–25° and additional 2-(methylamino)ethanol (1.5 ml) is added. The mixture is stirred for 1.5 hr, concentrated to a gum and diluted with methylene chloride (85 ml) and water (20 ml). The layers are separated and the organic phase is washed with water and dried over magnesium sulfate. Removal of solvent under reduced pressure gives the title compound, NMR (CDCl$_3$) 8.27, 8.14, 6.76, 4.38, 3.88 and 2.87δ.

PREPARATION 37

2-(N-Methyl-N-(3-nitro-2-pyrid-2-yl)amino)ethylindole-2-carboxylate

Indole-2-carboxylic acid (468 mg), 1,3-dicyclohexylcarbodiimide (595 mg), and 4-dimethylaminopyridine (71 mg) are added to 2-(N-methyl-N-(3-nitro-2-pyridinyl)-amino)ethanol (PREPARATION 36, 571 mg) in dry methylene chloride (20 ml). The mixture is stirred at 20°–25° for 22 hr after which additional 1,3-dicyclohexylcarbodiimide (180 mg), 4-dimethylaminopyridine (71 mg) and methylene chloride (10 ml) are added. The mixture is stirred 4 hr, filtered and concentrated to dryness. The residue is taken up in ethyl acetate, filtered, washed with aqueous hydrochloric acid (10%), water, saline and dried over sodium sulfate. Removal of solvent under reduced pressure gives a solid which is chromatographed on 70–230 mesh silica gel (90 g) eluting with a gradient of 10–50% ethyl acetate in hexane. The appropriate fractions [TLC on silica gel, R$_f$=0.63, ethyl acetate/hexane (50/ 50)] are pooled and removal of solvent gives the title compound, mp 124.1°–125.1°.

PREPARATION 38

N-Methyl-N-(2-hydroxyethyl)indole-2-carboxamide 1,1'-carbonyldiimidazole (1.11 g) is added to a solution of indole-2-carboxylic acid (1.0 g) in tetrahydrofuran (15 ml). The mixture is stirred 1 hour at 20°–25° and 2-(methylamino)ethanol (5.0 ml) is added. The mixture is stirred 21 hours at 20°–25° and 24 hours at reflux. The mixture is concentrated under reduced pressure, diluted with methylene chloride and extracted with water and saturated sodium bicarbonate. The phases are separated and the organic phase is dried with saline and sodium sulfate and concentrated to give the crude product. Chromatography on silica gel with a methanol/chloroform gradient followed by recrystallization from chloroform/ether to give the title compound, mp 141°–142.5°.

PREPARATION 39

2-(2-N-Methyl-N-(indolyl-2-carbonyl)amino)ethoxy)-3-aminopyridine

Sodium hydride in oil (60%, 48 mg) is added to a solution of N-methyl-N-(2-hydroxyethyl)indole-2-carboxamide (PREPARATION 38, 250 mg) in dimethylformamide (10 ml). The mixture is stirred 10 minutes and 2-chloro-3-nitropyridine (164 mg) is added. The mixture is stirred 20 minutes at 20°–25°, diluted with water (20 ml) and concentrated under reduced pressure. The residue is dissolved in methylene chloride and extracted with water. The phases are separated and the organic layer is dried with saline and sodium sulfate. The solution in concentrated under reduced pressure and the residue is dissolved in methanol. Palladium black (200 mg) is added and the mixture is stirred 2 hours under an atmosphere of hydrogen gas. The mixture is filtered and concentrated. Chromatography on silica gel with a methanol/chloroform gradient gives the title compound, mp 156°–158°.

PREPARATION 40

2-(2-Hydroxyethoxy)-3-nitropyridine

Sodium hydride in oil (60%, 131 mg) is added to ethylene glycol (6.0 ml) and 2-chloro-3-nitropyridine (430 mg) is added. The mixture is stirred for 26 hours during which time additional sodium hydride in oil (60%, 100 mg) is added. Water is added, the pH is adjusted to 9 and the solution is extracted with methylene chloride (3×50 ml). The combined organic layers are dried with saline and sodium sulfate and concentrated. Chromatography on silica gel with a methanol/chloroform gradient affords the title compound, R$_f$=0.32 (TLC on silica gel, ethyl acetate/hexane [50/50]).

PREPARATION 41

2-(2-(Indolyl-2-carbonyl)ethoxy)-3-nitropyridine

Indole-2-carboxylic acid (109 mg), 1,3-dicyclohexylcarbodiimide (140 mg), and dimethylaminopyridine (17 mg) are added to a solution of 2-(2-hydroxyethoxy)-3-nitropyridine (PREPARATION 40, 125 mg) in methylene chloride (7 ml). The mixture is stirred 18 hours at 20°–25°, filtered and concentrated to dryness. The residue is taken up in ethyl acetate, filtered, washed with aqueous hydrochloric acid (10%), water, and saline dried over sodium sulfate and concentrated under reduced pressure. The residue is chromatographed on silica gel with ethyl acetate/hexane (15/85) to give the title compound, NMR (CDCl$_3$) 9.02, 8.35, 8.26, 7.68, 7.41, 7.32, 7.25, 7.15, 7.04, 4,86 and 4.75 $\delta$.

PREPARATION 42

3-Methylindole-2-carboxylic acid (I)

3-Methylindole (0.50 g) is dissolved in THF (7 ml) and cooled to −78°. Then n-butyl lithium (1.6M in hexane, 2.5 ml) is added dropwise. Meanwhile, dry carbon dioxide is bubbled through THF (14 ml) at −78° for 5 min. The mixture in the flask containing the indole is added via cannula and the reaction is allowed to slowly warm to 20°–25°. The mixture is concentrated under reduced pressure to dryness and reconstituted with THF (7 ml) and cooled to −78°. Then t-butyl lithium (1.6M pentane, 2.5 ml) is added dropwise to the flask containing the indole and the mixture is stirred for 1 hr. Meanwhile dry carbon dioxide is bubbled through THF (14 ml) at −78° and the above reaction is added via cannula to the cooled dry THF. After 1.5 hr at −78°, the reaction mixture is slowly warmed to 20°–25°, then poured into hydrochloric acid (1N) and extracted with methylene chloride, dried over anhydrous sodium sulfate and concentrated under reduced pressure to give the title compound, NMR (300 MHz, CDCl$_3$) 8.67, 7.57, 7.30–7.24, 7.05 and 2.56 $\delta$.

PREPARATION 43

1-[Indolyl-2-carbonyl]-4-[4-fluoro-2-nitrophenyl] piperazine 1-(Indolyl-2-carbonyl)piperazine (1.0 g) and 2,5-difluoronitrobenzene (0.68 g) are mixed together in 10 ml of acetonitrile and 0.72 g of potassium carbonate are added. The reaction is stirred 24 hr at 20°–25° and then heated to 50° for 8 hr. The reaction is poured into water, and extracted with chloroform (3×), dried over anhydrous sodium sulfate and concentrated under reduced pressure. Purification by flash column chromatography eluting with ethyl acetate/hexane (50/50) to THF/ethyl acetate (50/50) pooling and concentrating the appropriate fractions gives the title compound, NMR (300 MHz, CDCl$_3$) 7.65, 7.57, 7.46, 7.37–7.10, 6.82, 4.10 and 3.10 $\delta$.

PREPARATION 44

1-[Indolyl-2-carbonyl]-4-[2-amino-4-fluorophenyl] piperazine

1-[Indolyl-2-carbonyl]-4-[4-fluoro-2-nitrophenyl]piperazine (PREPARATION 43, 1.4 g) is dissolved in 90 ml of ethanol and 25 ml of THF. Then palladium on carbon (10%, 0.27 g) is added and the reaction is hydrogenated at 40 psi for 18 hr. The mixture is filtered through a plug of celite and concentrated under reduced pressure to give the title compound, NMR (300 MHz, CDCl$_3$) 7.65, 7.45, 7.27, 7.13, 6.88, 6.81, 6.48–6.37, 4.50–3.80 and 3.10–2.75 $\delta$.

PREPARATION 45

1-[Indolyl-2-carbonyl]-4-[5-fluoro-2-nitrophenyl] piperazine 1-(Indolyl-2-carbonyl)piperazine (0.70 g) and 2,4-difluoronitrobenzene (0.33 ml) are mixed together in 7 ml of acetonitrile and 0.42 g of potassium carbonate are added. The reaction is stirred 24 hr at 20°–25° and then heated to reflux for 12 hr. The reaction mixture is poured into water, and extracted with chloroform (3×), dried over anhydrous sodium sulfate and concentrated under reduced pressure to give the title compound, NMR (300 MHz, CDCl$_3$) 9.39, 7.96, 7.65, 7.43, 7.32–7.25, 7.14, 6.81–6.72, 4.13 and 3.18 $\delta$.

PREPARATION 46

1-[Indolyl-2-carbonyl]-4-[2-amino-5-fluorophenyl] piperazine

Following the general procedure of PREPARATION 44 and making non-critical variations but starting with 1-[indolyl-2-carbonyl]-4-[5-fluoro-2-nitrophenyl]piperazine (PREPARATION 45, 0.84 g), the title compound is obtained.

PREPARATION 47

1-[1,1-Dimethylethoxycarbonyl]-4-[3-(1-pyrrolidinyl)-2-pyridinyl]piperazine

1-[1,1-Dimethylethoxycarbonyl]-4-[3-amino-2-pyridinyl]piperazine (International Publication No. WO 88/08424, 0.50 g), 1,4-dibromobutane (0.21 ml) and potassium carbonate (0.30 g) are refluxed in 4 ml of acetonitrile for 1 week. After 1 week, additional dibromobutane (0.21 ml) is added and refluxing is continued for 3 days. The reaction mixture is poured into water, extracted with methylene chloride, dried over anhydrous sodium sulfate and concentrated under reduced pressure. The concentrate is purified by flash column chromatography eluting with ethyl acetate/hexane (10/90) to ethyl acetate/hexane (25/75). The appropriate fractions are pooled and concentrated to give the title compound, NMR (300 MHz, CDCl$_3$) 7.78, 6.98, 6.78, 3.52, 3.20–3.10, 1.87 and 1.44 $\delta$.

PREPARATION 48

1-[3-(1-Pyrrolidinyl)-2-pyridinyl]piperazine (II)

1-[1,1-Dimethylethoxycarbonyl]-4-[3-(1-pyrrolidinyl)-2-pyridinyl]piperazine (PREPARATION 47, 0.26 g) is dissolved in 1.3 ml of THF and cooled to 0°. Trifluoroacetic acid (1.3 ml) is added and the reaction is stirred at 0° for 20 min, and then warmed to 20°–25° for 20 min. Then the reaction is poured into 1N aqueous sodium hydroxide and extracted with (10/90, 2×50 ml), dried over anhydrous sodium sulfate and concentrated under reduced pressure to give the title compound, NMR (300 MHz, CDCl$_3$) 7.64, 6.81, 661, 3.05–2.94, 2.86–2.79 and 1.78–1.65 $\delta$.

PREPARATION 49

1-(3-Nitro-2-pyridinyl)-1,4-diazepine

Homopiperazine (15.58 g) is dissolved in 100 ml of acetonitrile. Potassium carbonate (8.7 g) is added and then the 2-chloro-3-nitropyridine (5.0 g) dissolved in 25 ml of acetonitrile is added dropwise. The reaction is stirred at 20°–25° 4 hr, then diluted with methylene chloride, washed with water (2 x), saline, dried over anhydrous sodium sulfate and concentrated under reduced pressure to give the title compound, NMR (300 MHz, $CDCl_3$) 8.30, 8.08, 6.66, 3.60, 3.41, 3.10, 2.89 and 1.93 δ.

PREPARATION 50

1-(1,1-Dimethylethoxycarbonyl)-4-(3-nitro-2-pyridinyl)-1,4-diazepine

Following the general procedure of PREPARATION 12 and making non-critical variations but starting with 1-(3-nitro-2-pyridinyl)-1,4-diazepine (PREPARATION 49, 7.06 g), the title compound is obtained, NMR (300 MHz, $CDCl_3$) 8.29, 8.05, 6.67, 3.76–3.29, 198, 1.34 and 1.29 δ.

PREPARATION 51

1-(1,1-Dimethylethoxycarbonyl)-4-(3-amino-2-pyridinyl)1,4-diazepine

Following the general procedure of PREPARATION 13 and making non-critical variations but starting with 1-(1,1-dimethylethoxycarbonyl)-4-(3-nitro-2-pyridinyl)-1,4diazepine (PREPARATION 50, 6.0 g), title compound is obtained, NMR (300 MHz, $CDCl_3$) 7.75, 693, 6.81, 3.86, 3.78, 3.66–3.57, 3.51, 3.36–3.2, 3.21, 1.95, 1.85, 1.48 and 1.47 δ.

PREPARATION 52

1-(1,1-Dimethylethoxycarbonyl)-4-(3-ethylamino-2pyridinyl)-1,4-diazepine

Following the general procedure of PREPARATION 6 and making non-critical variations but starting with 1-(1,1-dimethylethoxycarbonyl)-4-(3-amino-2-pyridinyl)-1,4diazepine (PREPARATION 51, 6.07 g), the title compound is obtained, NMR (300 MHz, $CDCl_3$) 7.65, 6.86, 6.76, 4.25, 4.11, 364–3.48, 3.30–3.21, 3.12–3.08, 1.92, 1.83, 1.47, and 1.45 δ.

PREPARATION 53

1-(3-Ethylamino-2-pyridinyl)-1,4-diazepine (II)

Following the general procedure of PREPARATION 9 and making non-critical variations but starting with 1-(1,1-dimethylethoxycarbonyl)-4-(3N-ethylamino-2-pyridinyl)-1,4-diazepine (PREPARATION 52, 5.12 g), the title compound is obtained, NMR (300 MHz, $CDCl_3$) 7.66, 6.85, 6.76, 4.17, 3.31–3.26, 3.14–3.01, 1.84 and 1.29 δ.

PREPARATION 54

1-(1,1-Dimethylethoxycarbonyl)-4-(3-(1-methylethyl)amino-2-pyridinyl)-1,4-diazepine Following the general procedure of PREPARATION 8 and making non-critical variations but starting with 1-(1,1-dimethylethoxycarbonyl)-4-(3-amino-2-pyridinyl)-1,4-diazepine (PREPARATION 51, 18.13 g), the title compound is obtained, NMR (300 MHz, $CDCl_3$) 7.62, 6.85, 6.76, 4.18, 3.63–3.48, 3.28–3.19, 3.07, 1.92, 1.83, 1.46, 1.45 and 1.23 δ.

PREPARATION 55

1-(3-(1-Methylethyl)amino-2-pyridinyl)-1,4-diazepine (II)

Following the general procedure of PREPARATION 9 and making non-critical variations but starting with 1-(1,1-dimethylethoxycarbonyl)-4-(3-(1-methylethyl)-2pyridinyl)-1,4-diazepine (PREPARATION 54, 15.08 g), the title compound is obtained, NMR (300 MHz, $CDCl_3$) 7.61, 6.82, 6.75, 4.17, 3.50, 3.28–3.22, 3.06–3.01, 2.67, 1.83 and 1.20 δ.

PREPARATION 56

Ethyl 5-(Benzyloxycarbonylamino)indole-2-carboxylate

Ethyl 5-aminoindole-2-carboxylate [J. Am. Chem. Soc. 80, 4621 (1958) JCS Perkin I 53 (1977), 0.50 g] is dissolved in 49 ml of methylene chloride and pyridine (0.20 g) is added. The reaction is cooled to 0° and benzylchloroformate (0.36 ml) is added dropwise over 10 min. The reaction is stirred for 1 hr, diluted with chloroform, washed with saturated aqueous sodium bicarbonate, water, saline, dried over anhydrous sodium sulfate and concentrated under reduced pressure. The concentrate is purified by flash column chromatography (150 g silica gel) eluting with hexane/ethyl acetate (3/1). The appropriate fractions are pooled and concentrated to give the title compound, NMR (300 MHz, $CDCl_3$) 8.90, 7.79, 7.41–7.33, 7.24, 7.16, 5.22, 4.40 and 1.41 δ.

PREPARATION 57

5-Benzyloxycarbonylaminoindole-2-carboxylic acid (I)

Ethyl 5-Benzyloxycarbonylaminoindole-2-carboxylate, (PREPARATION 56, 0.76 g) is dissolved in 1,4-dioxane (5.6 ml) and water (0.56 ml). Crushed potassium hydroxide (0.23 g) is added and the reaction is heated to 50° for 5 hr. The reaction is neutralized by adding 4.05 ml of 1N aqueous hydrochloric acid. The reaction is extracted with THF/chloroform (10/90, 3x), saline, dried over anhydrous sodium sulfate and concentrated under reduced pressure to give the title acid, NMR (300 MHz, d4-CD3OD) 7.64, 7.34–7.15, 6.98 and 5.09 δ.

PREPARATION 58

1-[5-Benzyloxycarbonylaminoindolyl-2-carbonyl]-4-(3-(1-methylethyl)amino-2-pyridinyl)piperazine 5-Benzyloxycarbonylaminoindole-2-carboxylic acid (PREPARATION 57, 0.65 g), and 1-(3-(1-methylethyl)amino-2-pyridinyl)piperazine (0.506 g) are dissolved in 4.2 ml of THF. EDC (0.48 g) is added and the reaction is stirred for 2 h. The reaction mixture is diluted with chloroform, washed with saturated aqueous sodium bicarbonate, saline, dried over anhydrous sodium sulfate and concentrated under reduced pressure. The concentrate is purified by flash column chromatography (35 g silica gel) eluting with methanol/chloroform (5/95). The appropriate fractions are pooled and concentrated to give the title compound, NMR (300 MHz, d4-CD3OD) 7.66, 7.47, 7.31–7.14, 6.89, 6.69, 5.09, 3.93, 3.54, 2.98 and 1.17δ.

PREPARATION 60

1-[5-(2'-Benzyloxyglycylamino)indolyl-2-carbonyl]-4-(3-(1-methanol/chloroform methylethyl)-amino-2-pyridinyl)piperazine 1-(5-Aminoindolyl-2-carbonyl]-4-(3-(1-methylethyl)amino-2-pyridinyl)piperazine (EXAMPLE 9, 2.5 g), N-carbobenzyloxyglycine (1.52 g) and EDC (1.52 g) are stirred together at 20°–25° in 13 ml of THF for 3 hr. The reaction mixture is diluted with chloroform, washed with saturated aqueous sodium bicarbonate, saline, dried over anhydrous sodium sulfate and concentrated under reduced pressure. The concentrate is purified by flash column chromatography eluting with methanol/chloroform (5/95). The appropriate fractions are pooled and concentrated to give the title compound, NMR (300 MHz, CD3OD) 7.75, 7.43, 7.26–7.20, 6.86, 6.69, 4.99, 3.90–3.80, 3.52, 2.96 and 1.11 δ.

PREPARATION 61

1-Methyl 4-methoxy-α-azidocinnamate p-Methoxybenzaldehyde (5.0 g) and methyl azidoacetate (16.9 g) are dissolved in 125 ml of methanol and cooled to −10° (ice-acetone bath). Then sodium methoxide (7.93 g, 25% in methanol) is added dropwise such that the temperature does not rise above −5°. After 2 hr the cooling bath is removed and the reaction is warmed to 20°–25° while being monitored by TLC. When no starting material remained, the reaction is diluted with ether and saturated ammonium chloride. After extracting with ether the organic layers are washed with ammonium chloride, saline, dried over anhydrous sodium sulfate and concentrated under reduced pressure. The concentrate is purified by flash column chromatography eluting with ethyl acetate/hexane (1/99) to ethyl acetate/hexane (10/90). The appropriate fractions are pooled and concentrated to give the title compound, NMR (300 MHz, CDCl$_3$) 7.80–7.76, 692–6.87, 3.88 and 3.79 δ.

PREPARATION 62

Methyl 6-Methoxyindole-2-carboxylate

Toluene (185 ml) is added to methyl 4-methoxy-α-azidocinnamate (PREPARATION 61, 7.73 g) and the reaction is brought to reflux and maintained at reflux for 3 hr. Then the reaction is concentrated under reduced pressure and triturated with hexane. The solids are filtered and dried under reduced pressure to give the title indole, HRMS Calcd. for $C_{11}H_{11}NO_3$: 205.0739, found: 205.0736; NMR (300 MHz, CDCl$_3$) 8.75, 7.47, 7.11, 6.76–6.73, 3.86, and 3.79 δ.

PREPARATION 63

6-Methoxyindole-2-carboxylic acid (I)

Methyl 6-methoxyindole-2-carboxylate (PREPARATION 62, 571 g) is dissolved in 70 ml of dioxane and 7 ml of water and 1.87 g of crushed potassium hydroxide are added. The reaction is heated to 50° and stirred 1.5 hr. The reaction mixture is acidified to pH 4–5 and extracted several times with methanol/chloroform (10/90). The organic layers are combined and dried over anhydrous magnesium sulfate and concentrated under reduced pressure to give the title acid, NMR (300 MHz, d4-CD$_3$OD) 7.47, 7.08, 6.90, 6.72 and 3.82 δ.

PREPARATION 64

Methyl 4-fluoro-α-azidocinnamate

Following the general procedure of PREPARATION 61 and making non-critical variations but starting with p-fluorobenzaldehyde (5.0 g), the title compound is obtained, NMR (300 MHz, CDCl$_3$) 7.82, 7.07, 6.87 and 3.91 δ.

PREPARATION 65

Methyl 6-fluoroindole-2-carboxylate

Following the general procedure of PREPARATION 62 and making non-critical variations but starting with methyl 4-fluoro-α-azidocinnamate (PREPARATION 64, 7.00 g), the title compound is obtained, NMR (300 MHz, CDCl$_3$) 8.95, 7.61, 7.20, 7.08, 6.93 and 3.95 δ.

PREPARATION 66

6-Fluoroindole-2-carboxylic acid (I)

Following the general procedure of PREPARATION 63 and making non-critical variations but starting with methyl 6-fluoroindole-2-carboxylate (PREPARATION 65, 1.77 g), the title compound is obtained, NMR (300 MHz, d4-CD$_3$OD) 7.60, 7.13, 7.10 and 6.85 δ.

PREPARATION 67

Methyl 2-methoxy-α-azidocinnamate

Following the general procedure of PREPARATION 61 and making non-critical variations but starting with 2-methoxybenzaldehyde (4.6 g), the title compound is obtained, NMR (300 MHz, CDCl$_3$) 8.18, 7.39, 7.32, 6.99, 6.87, 3.90 and 3.86 δ.

PREPARATION 68

Methyl 4-Methoxyindole-2-carboxylate

Following the general procedure of PREPARATION 62 and making non-critical variations but starting with methyl 2-methoxy-α-azidocinnamate (PREPARATION 67, 4.56 g), the title compound is obtained, NMR (300 MHz, CDCl$_3$) 9.02, 7.34, 7.26, 7.02, 6.50, 3.95 and 3.94 δ.

PREPARATION 69

4-Methoxyindole-2-carboxylic acid (I)

Following the general procedure of PREPARATION 63 and making non-critical variations but starting with methyl 4-methoxyindole-2-carboxylate (PREPARATION 68, 3.16 g), the title compound is obtained, NMR (300 MHz, d4-CD$_3$OD) 7.18, 7.16, 7.00, 6.49 and 3.92 δ.

PREPARATION 70

1-[1,1-Dimethylethoxycarbonyl]-4-[3-(1-methylpropyl) amino-2-pyridinyl]piperazine Following the general procedure of PREPARATION 8 and making non-critical variations but starting with 1-[1,1-dimethylethoxycarbonyl]-4-[(3-amino)-2-pyridinyl)piperazine (International Publication No. WO 88/08424, 1.0 g), 2-butanone (0.27 g) sodium cyanoborohydride (0.23 g), acetic acid (5.1 ml) and methanol, the title compound is obtained, NMR (300 MHz, CDCl$_3$) 7.68, 6.94, 6.86, 4.18, 3.56, 3.33, 3.05, 1.53, 1.47, 1.18 and 0.96 δ.

PREPARATION 71

1-[3-(1-Methylpropyl)amino)-2-pyridinyl]piperazine (II)

Following the general procedure of PREPARATION 9 and making non-critical variations but starting with 1-[1,1-dimethylethoxycarbonyl]-4-[3-(1-methylpropyl)amino-2-pyridinyl)piperazine (PREPARATION 70, 1.62 g), trifluoroacetic acid (5.52 g) and 10 ml of methylene chloride, the title compound is obtained, NMR (300 MHz, CDCl$_3$) 7.66, 6.87, 6.78, 4.17, 3.31, 3.06, 2.81, 1.64–1.48, 1.17 and 0.95 δ.

PREPARATION 72

1-[Benzyloxycarbonyl]-4-[3-(1-ethylpropylamino)-2-pyridinyl]piperazine

Following the general procedure of PREPARATION 8 and making non-critical variations but starting with 1-[benzyloxycarbonyl]-4-[(3-amino)-2-pyridinyl]piperazine (PREPARATION 100 10.5 g), 3-pentanone (0.15 g) sodium cyanoborohydride (0.11 g), acetic acid (52.3 ml) and methanol (3.2), the title compound is obtained, NMR (300 MHz, CDCl$_3$) 7.66, 7.38–7.33, 6.90, 6.79, 5.17, 4.21, 3.65, 3.15, 3.04, 1.66–1.46 and 0.93 δ.

PREPARATION 73

1-[3-(1-Ethylpropyl)amino-2-pyridinyl]piperazine (II)

Following the general procedure of PREPARATION 59 and making non-critical variations but starting with 1-[1-benzyloxycarbonyl]-4-[(3-(1-ethylpropylamino)-2-pyridinyl)piperazine (PREPARATION 72, 0.30 g), 10% palladium on carbon (30 mg) and ethyl acetate (10 ml), the title compound is obtained, NMR (300 MHz, CDCl$_3$) 7.65, 6.87, 6.78, 4.19, 3.40–3.10, 3.00–2.75, 1.64–1.49, and 0.93 δ.

PREPARATION 74

N,N'-Dimethyl-N-(5-methoxyindolyl-2-carbonyl)-N'-(3-nitro-2-pyridinyl)ethylenediamine Following the general procedure of PREPARATION 35 and making non-critical variations but starting with 5-methoxyindole-2-carboxylic acid the title compound is obtained, mp 165°–167°.

PREPARATION 75

N,N'-Dimethyl-N-(5-fluoroindolyl-2-carbonyl)-N'-(3-nitro-2-pyridinyl)ethylenediamine Following the general procedure of PREPARATION 35 and making non-critical variations but employing 5-fluoroindole-2-carboxylic acid, the title compound is obtained, mp 161°–162°.

PREPARATION 76

7-Azaindole-2-carboxylic acid (I)

Following the general procedure of PREPARATION 42 and making non-critical variations employing 7-azaindole, the title compound is obtained, NMR (300 MHz, d$_6$-DMSO) 12.64, 8.44, 8.25, 7.25 and 7.18 δ.

PREPARATION 77

Methyl 3,4-methylenedioxy-α-azidocinnamate

Following the general procedure of PREPARATION 61 and making non-critical variations but starting with piperonal (5.0 g), and methyl azido acetate (15.3 g), the title compound is obtained, NMR (300 MHz, CDCl$_3$) 7.56, 7.17, 6.84, 6.82, 6.00 and 3.90 δ.

PREPARATION 78

Methyl 5,6-methylenedioxyindole-2-carboxylate

Following the general procedure of PREPARATION 62 and making non-critical variations but starting with methyl 3,4-methylenedioxy-α-azidocinnamate (PREPARATION 77, 5.38 g), the title compound is obtained, NMR (300 MHz, CDCl$_3$) 8.90, 7.08, 6.99, 6.82, 5.97 and 3.91 δ.

PREPARATION 79

5,6-Methylenedioxyindole-2-carboxylic acid (I)

Following the general procedure of PREPARATION 63 and making non-critical variations but starting with methyl 5,6-methylenedioxyindole-2-carboxylate (PREPARATION 78, 4.77 g), potassium hydroxide (1.47 g), the title compound is obtained, C,H,N analysis calcd. for C$_{10}$H$_7$NO$_4$ C,58.54; H, 3.44; N, 6.83; found: C,58.27; H, 3.18; N, 6.95.

PREPARATION 80

Methyl 3-bromo-4-methoxy-α-azidocinnamate

Following the general procedure of PREPARATION 61 and making non-critical variations but starting with 3-bromo-4-methoxybenzaldehyde (5.0 g) and methyl azidoacetate (10.7 g), the title compound is obtained, NMR (300 MHz, CDCl$_3$) 8.10, 7.73, 6.89, 6.79, 3.94 and 3.90 δ.

PREPARATION 81

Methyl 5-bromo-6-methoxyindole carboxylate and methyl 7-bromo-6-methoxyindole carboxylate Following the general procedure of PREPARATION 62 and making non-critical variations but starting with methyl 3-bromo-4-methoxy-α-azidocinnamate (PREPARATION 80, 3.25 g), the title compounds are obtained (2.22 g of methyl 5-bromo-6-methyoxyindole carboxylate and 0.46 g of methyl 7-bromo-6-methoxyindole carboxylate). They are separated by careful chromatography (5% acetone/hexane to 20% acetone/hexane). Methyl 5-bromo-6-methoxyindole carboxylate, NMR (300 MHz, CDCl$_3$) 8.87, 7.86, 7.09, 6.88 and 3.93 δ. Methyl 7-bromo-6-methoxyindole carboxylate, NMR (300 MHz, CDCl$_3$) 8.83, 7.58, 7.24, 6.89, 3.98 and 3.95 δ.

PREPARATION 82

5-Bromo-6-methoxyindole-2-carboxylic acid (I)

Following the general procedure of PREPARATION 63 and making non-critical variations but starting with methyl 5-bromo-6-methoxyindole carboxylate (PREPARATION 81, 3.31 g) and potassium hydroxide (0.98 g), the title compound is obtained, NMR (300 MHz, $CD_3OD$) 7.79, 7.03, 7.01 and 3.89 δ.

PREPARATION 83

7-Bromo-6-methoxyindole-2-carboxylic acid (I)

Following the general procedure of PREPARATION 63 and making non-critical variations but starting with methyl 7-bromo-6-methoxyindole carboxylate (PREPARATION 81, 0.36 g) and potassium hydroxide (0.11 g), the title compound is obtained, NMR (300 MHz, $CD_3OD$) 7.58, 7.20, 6.96 and 3.93 δ.

PREPARATION 84

Methyl 2-methyl-α-azidocinnamate

Following the general procedure of PREPARATION 61 and making non-critical variations but starting with o-tolualdehyde (5.0 g), methyl azidoacetate (19.2 g), the title compound is obtained, NMR (300 MHz, $CDCl_3$) 7.96, 7.26–7.18, 7.13, 3.92 and 2.36 δ.

PREPARATION 85

Methyl 4-methylindole-2-carboxylate

Following the general procedure of PREPARATION 62 and making non-critical variations but starting with methyl 2-methyl-α-azidocinnamate (PREPARATION 84, 6.77 g), the title compound is obtained, NMR (300 MHz, $CDCl_3$) 8.93, 7.27–7.20, 6.94, 3.95 and 2.57 δ.

PREPARATION 86

4-Methylindole-2-carboxylic acid (I)

Following the general procedure of PREPARATION 63 and making non-critical variations but starting with methyl 4-methylindole-2-carboxylate (PREPARATION 85, 4.94 g), potassium hydroxide (1.75 g), the title compound is obtained, NMR (300 MHz, $CD_3OD$) 7.24, 7.19, 7.12, 6.85 and 2.51 δ.

PREPARATION 87

Methyl 4-N,N-dimethylamino-α-azidocinnamate

Following the general procedure of PREPARATION 61 and making non-critical variations but starting with 4-dimethylaminobenzaldehyde (5.0 g), methyl azido acetate (15.4 g), the title compound is obtained, NMR (300 MHz, $CDCl_3$) 7.74, 6.69, 3.88 and 3.03 δ.

PREPARATION 88

Methyl 6-(N,N-dimethylamino)indole-2-carboxylate

Following the general procedure of PREPARATION 62 and making non-critical variations but starting with methyl 6-(N,N-dimethyl)amino-α-azidocinnamate (PREPARATION 87, 1.46 g), the title compound is obtained, NMR (300 MHz, $CDCl_3$) 8.70, 7.53, 7.12, 6.82, 6.69, 3.91, and 3.01 δ.

PREPARATION 89

6-(N,N-Dimethylamino)indole-2-carboxylic acid (I)

Following the general procedure of PREPARATION 63 and making non-critical variations but starting with methyl 6-(N,N-dimethylamino)indole-2-carboxylate (PREPARATION 88, 0.80 g), potassium hydroxide (0.25 g), the title compound is obtained, NMR (300 MHz, $CD_3OD$) 7.62, 7.13, 7.11, 7.01, and 3.11 δ.

PREPARATION 90

Methyl 3-fluoro-4-methoxy-α-azidocinnamate

Following the general procedure of PREPARATION 61 and making non-critical variations but starting with 3-fluoro-4-methoxybenzaldehyde (5.0 g), and methylazido acetate (14.91 g), the title compound is obtained, NMR (300 MHz, $CDCl_3$) 7.75, 7.45, 6.95, 6.81, 3.93, and 3.90 δ.

PREPARATION 91

Methyl 5-fluoro-6-methoxyindole-2-carboxylate

Following the general procedure of PREPARATION 62 and making non-critical variations but starting with methyl 3-fluoro-4-methoxy-α-azidocinnamate (PREPARATION 90, 1.31 g), the title compound is obtained, NMR (300 MHz, $CDCl_3$) 8.88, 7.32, 7.12, 6.90, and 3.93 δ.

PREPARATION 92

5-Fluoro-6-methoxyindole-2-carboxylic acid (I)

Following the general procedure of PREPARATION 63 and making non-critical variations but starting with methyl 3-fluoro-4-methoxyindole-2-carboxylate (PREPARATION 91, 1.05 g), potassium hydroxide (0.32 g), the title compound is obtained (0.98 g, mp 239°–240°), NMR (300 MHz, $CD_3OD$) 7.27, 7.06, 7.03, and 3.89 δ.

PREPARATION 93

Methyl 4-nitro-α-azidocinnamate

Following the general procedure of PREPARATION 61 and making non-critical variations but starting with p-nitrobenzaldehyde (10 g) and methyl azidoacetate (30.4 g), the title compound is obtained, NMR 8.34, 8.07, 7.02, and 4.07 δ.

PREPARATION 94

Methyl 6-nitroindole-2-carboxylate

Following the general procedure of PREPARATION 62 and making non-critical variations but starting with methyl 4-nitro-α-azidocinnamate (PREPARATION 93, 6.75 g), the title compound is obtained, NMR (300 MHz, $CD_3OD$) 8.30, 7.87, 7.12, 7.18, and 3.86 δ.

PREPARATION 95

6-Nitroindole-2-carboxylic acid (I)

Following the general procedure of PREPARATION 63 and making non-critical variations but starting with methyl 6-nitroindole-2-carboxylate (PREPARATION 94), the title compound is obtained.

PREPARATION 96

Methyl-4-diethoxymethyl-α-azidocinnamate

Following the general procedure of PREPARATION 61 and making non-critical variations but starting with terephthaldehyde mono-(diethyl acetal), the title compound is obtained.

PREPARATION 97

Methyl 6-formylindole-2-carboxylate

Following the general procedure of PREPARATION 62 and making non-critical variations but starting with methyl-4-diethoxymethyl-α-azidocinnamate (PREPARATION 96), the title compound is obtained.

PREPARATION 98

6-Formylindole-2-carboxylic acid (I)

Following the general procedure of PREPARATION 63 and making non-critical variations but starting with methyl 6-formylindole-2-carboxylate (PREPARATION 97), the title compound is obtained, NMR (300 MHz, CD$_3$OD) 9.91, 7.39, 7.69, 7.53 and 7.11 δ.

PREPARATION 99

1-[Benzyloxycarbonyl]-4-[3-nitro-2-pyridinyl]piperazine 1-(3-Nitro-2-pyridinyl)piperazine is dissolved in 175 ml of methylene chloride and cooled to 0°. Then pyridine is added followed by benzylchloroformate (16.5 ml). The reaction is stirred 1.5 hr, then poured into saturated aqueous sodium bicarbonate and extracted with chloroform, dried over anhydrous sodium sulfate and concentrated in vacuo to afford the title compound, NMR (300 MHz, CDCl$_3$) 8.34, 8.15, 7.38–7.32, 6.81, 5.17, 3.65 and 3.45 δ.

PREPARATION 100

1-[Benzyloxycarbonyl]-4-[3-amino-2-pyridinyl]piperazine

1-[Benzyloxycarbonyl]-4-[3-nitro-2-pyridinyl]piperazine (PREPARATION 99), is dissolved in dioxane (923 ml) and cooled to 0°. Then aqueous titanium trichloride (20%, 555.3 ml) is added cautiously. After stirring 30 min the reaction is diluted with aqueous sodium hydroxide solution (2N, 1.5 l) and filtered through celite. The filter cake is washed with methanol/chloroform (10/90). The combined organic layers are washed with water, saline, dried and concentrated in vacuo to afford the desired product, NMR (300 MHz, CDCl$_3$) 7.80, 7.38–7.32, 6.99, 6.88, 5.17, 3.67 and 3.12 δ.

PREPARATION 101

1-[Benzyloxycarbonyl]-4-[3-(2,2,2-trifluoroacetamido)-2-pyridinyl]piperazine

1-[Benzyloxycarbonyl]-4-[3-amino-2-pyridinyl]piperazine (PREPARATION 100), is dissolved in 50 ml of methylene chloride and triethylamine is added. The reaction is cooled to 0° and trifluoroacetic anhydride is added dropwise. After 30 min, the reaction is poured into saturated aqueous sodium bicarbonate solution and extracted with chloroform, washed with saline, dried over anhydrous sodium sulfate and concentrated in vacuo, NMR (300 MHz, CDCl$_3$) 8.92, 8.54, 8.22, 7.39–7.32, 7.16, 5.17, 3.70 and 3.03 δ.

PREPARATION 102

1-[3-(2,2,2-Trifluoroacetamido)-2-pyridinyl]piperazine

1-[Benzyloxycarbonyl]-4-[3-(2,2,2-trifluoroacetamido)-2-pyridinyl]piperazine (PREPARATION 101), is dissolved in 70 ml of ethanol and 0.25 g of 10% palladium on carbon is added. The reaction is hydrogenated at 40 psi for 20 hr. Then it is filtered through a pad of celite and concentrated in vacuo to afford the title compound which is used without further purification, NMR (300 MHz, CDCl$_3$) 8.51, 8.21, 7.19, and 3.45–3.47 δ.

PREPARATION 103

1-[3-(2,2,2-trifluoroethylamino)-2-pyridinyl]piperazine (II)

1-[3-(2,2,2-Trifluoroacetamido)-2-pyridinyl]piperazine (PREPARATION 102), is dissolved in 5 ml of tetrahydrofuran and cooled to 0°. Then 4.84 ml of lithium aluminum hydride solution is added dropwise. After 10 min of stirring at 0°, the reaction is warmed to 20°–25° and stirred 45 min. The reaction is quenched at 0° with the dropwise addition of 0.4 ml of water, 0.6 ml of 10% aqueous sodium hydroxide, and 1 ml of water. The slurry is filtered through celite, washed with 20% methanol/chloroform and concentrated in vacuo to afford the title amine which is used without further purification, NMR (300 MHZ, CDCl$_3$) 7.82, 6.97–6.92, 4.86, 3.75, and 3.06–3.01 δ.

PREPARATION 104

1-Benzyloxycarbonyl-4-[3-(2-fluoroacetamido)-2-pyridinyl]piperazine

Following the general procedure of PREPARATION 101 and making non-critical variations but starting with fluoroacetyl chloride (0.94 g), 1-benzyloxycarbonyl-4-[3-amino-2-pyridinyl]piperazine (PREPARATION 100, 3.0 g), the title compound is obtained, NMR (300 MHZ, CDCl$_3$) 8.83, 8.65, 8.14, 7.38–7.32, 7.12, 5.17, 4.96, 3.70 and 3.07 δ.

PREPARATION 105

1-[3-(2-Fluoroacetamido)-2-pyridinyl]piperazine

Following the general procedure of PREPARATION 102 and making non-critical variations but starting with 1-benzyloxycarbonyl-4-[3-(2'-fluoroacetamido)-2-pyridinyl]piperazine (2.42 g), 10% palladium on carbon (0.25 g), the title compound is obtained, NMR (300 MHZ, CDCl$_3$) 8.15, 7.97, 7.00, 4.88, 4.73 and 3.13δ.

PREPARATION 106

1-[3-(2-Fluoroethylamino)-2-pyridinyl]piperazine (II)

Following the general procedure of PREPARATION 103 and making non-critical variations but starting with 1-[3-(2-fluoroacetamido)-2-pyridinyl]piperazine (PREPARATION 105, 1.4 g), lithium aluminum hydride (11.76 ml, 1M in tetrahydrofuran), the title compound is obtained.

PREPARATION 107

1-[3-(1-Methylethylamino)-2-pyrazinyl]-1,4-diazepine (II)

Following the general procedure of PREPARATION 24 and making non-critical variations but starting with homopiperazine (2.46 g) and 2-chloro-3-(1-methylethyl)aminopyrazine (PREPARATION 23), the title compound is obtained, NMR (300 MHz, CDCl$_3$) 7.56, 7.34, 4.75, 4.04, 3.28–3.18, 3.00–2.94, 1.79, and 1.15$\delta$.

PREPARATION 108

3,5-Dichloro-4-(1,1-dimethylethylamino)pyridazine

Following the general procedure of PREPARATION 31 and making non-critical variations but starting with t-butylamine (66.5 ml), and 3,4,5-trichloropyridazine, the title compound is obtained, NMR (300 MHz, CDCl$_3$) 8.50, 5.09, and 1.55$\delta$.

PREPARATION 109

1-[5-Chloro-4-(1,1-dimethylethylamino)-3-pyridazinyl]piperazine

Following the general procedure of PREPARATION 32 and making non-critical variations but starting with 3,5-dichloro-4-(1,1-dimethylethylamino)pyridazine (PREPARATION 108), the title compound is obtained, NMR (300 MHz, CDCl$_3$) 8.55, 5.04, 3.25, 3.07, and 1.44$\delta$.

PREPARATION 110

1-[4-(1,1-Dimethylethylamino)-2-pyridazinyl]piperazine (II)

Following the general procedure of PREPARATION 28 and making non-critical variations but starting with 1-[5-chloro-4-(1,1-dimethylethylamino)-3-pyridazinyl]piperazine (PREPARATION 109), and triethylamine (4.6 ml), the title compound is obtained, NMR (300 MHz, CDCl$_3$) 8.53, 6.79, 5.57, 3.55, and 1.47$\delta$.

PREPARATION 111

Methyl 2-azido-3-(2-naphthyl)propionate

Following the general procedure of PREPARATION 61 and making non-critical variations but starting with 2-naphthaldehyde (5.0 g), the title compound is obtained, NMR (300 MHz, CDCl$_3$) 8.28, 7.94, 7.90–7.79, 7.51, 7.07, and 3.93$\delta$.

PREPARATION 112

Methyl benz[g]indole-2-carboxylate

Following the general procedure of PREPARATION 62 and making non-critical variations but starting with methyl 2-azido-3-(2-naphthyl)propionate (PREPARATION 111, 4.28 g), the title compound is obtained, NMR (300 MHz, CDCl$_3$) 9.36, 8.20, 7.92, 7.67, 7.61–7.46, 7.33 and 4.00$\delta$.

PREPARATION 113

Benz[g]indole-2-carboxylic acid (I)

Following the general procedure of PREPARATION 63 and making non-critical variations but starting with methyl benz[g]indole-2-carboxylate (PREPARATION 112, 3.78 g), the title compound is obtained, NMR (300 MHz, CD$_3$OD) 8.35, 7.78, 7.54, 7.44, 7.40–7.34 and 7.17$\delta$.

PREPARATION 114

Methyl 2-azido-3-(1-naphthyl)propionate

Following the general procedure of PREPARATION 61 and making non-critical variations but starting with 1-naphthaldehyde (4.0 g), the title compound is obtained.

PREPARATION 115

Methyl benz[e]indole-2-carboxylate

Following the general procedure of PREPARATION 62 and making non-critical variations but starting with methyl 2-azido-3-(1-naphthyl)propionate (PREPARATION 114, 6.54 g), the title compound is obtained, NMR (300 MHz, CDCl$_3$) 9.25, 8.23, 7.89, 7.02, 7.75, 7.62–7.51, 7.51–7.40, and 3.98$\delta$.

PREPARATION 116

Benz[e]indole-2-carboxylic acid (I)

Following the general procedure of PREPARATION 63 and making non-critical variations but starting with methyl benz[e]indole-2-carboxylate (PREPARATION 115, 1.28 g), the title compound is obtained, NMR (300 MHz, CD$_3$OD) 8.23, 7.85, 7.70, 7.64, 7.52, and 7.39$\delta$.

PREPARATION 117

1-[1,1-Dimethylethoxycarbonyl]-4-[3-(2-propenylamino)-2-pyridinyl]piperazine

A mixture of 1-[1,1-dimethylethoxycarbonyl]-4-[3-amino-2-pyridinyl]piperazine (International Publication 88/08424, 2.78 g), 2-bromopropene (1.87 g), anhydrous potassium carbonate (3.3 g) and acetonitrile (100 ml) is refluxed for 36 hr. The mixture is cooled and then diluted with dichloromethane and aqueous potassium carbonate solution. The phases are separated and the organic phase is washed with saline and than concentrated in vacuo. Purification by flash column chromatography (2% methanol/chloroform) provided of the title compound. Capillary GC analysis (HP1 column, initial temperature at 100° for 1 min, then programmed to rise 20° per minute to 250°) gave a peak at 6.06 (96%) minutes.

PREPARATION 118

1-[3-(2-Propenylamino)-2-pyridinyl]piperazine (II)

Following the procedure of PREPARATION 7 and making non-critical variations but starting with 1-[1,1-dimethylethoxycarbonyl]-4-[3-(2-propenyl)-2-pyridinyl]piperazine (PREPARATION 117, 0.7 g), the title compound is obtained. TLC analysis (silica gel, eluent: 15% methanol/chloroform, visualization with UV light and iodine vapor) showed one spot, Rf=0.1.

PREPARATION 119

Methyl 6-hydroxymethylindole-2-carboxylate

Sodium borohydride is added to a solution of methyl 4-formylmethyl-α-azidoinnamate in methanol at 0°. After 30 min, the reaction is warmed to 20°–25° and stirred for a further 30 min. Then it is cooled to 0° and quenched via the addition of water. The product is extracted with chloroform, dried over anhydrous sodium sulfate and concentrated in vacuo to provide the title compound.

PREPARATION 120

Methyl-4-hydroxymethyl-α-azidocinnamate

Following the general procedure of PREPARATION 62 and making non-critical variations but starting with methyl 4-hydroxymethyl-α-azidocinnamate (PREPARATION 119), the title compound is obtained.

PREPARATION 121

6-Hydroxymethylindole-2-carboxylic acid (I)

Following the general procedure of PREPARATION 63 and making non-critical variations but starting with methyl 6-hydroxymethylindole-2-carboxylate (PREPARATION 120), the title compound is obtained.

PREPARATION 122

1-[6-Methanesulfonyloxymethylindolyl-2-carbonyl]-4-[3-(1-methylethylamino)-2-pyridinyl] piperazine (III)

1-[6-Hydroxymethylindolyl-2-carbonyl]-4-[3-(1-methylethylamino)-2-pyridinyl]piperazine (EXAMPLE 126) is dissolved in methylene chloride and cooled to 0°. Then pyridine followed by methanesulfonyl chloride are added. The reaction is stirred for 30 min, then poured into aqueous sodium bicarbonate solution and extracted with chloroform. The organic layers are dried over anhydrous sodium sulfate and concentrated in vacuo to afford the title compound.

PREPARATION 123

5,6-Dihydro-1H-3H-pyrrolo-[3,2,1,i,j]-[3,1] benzoxazine-1,3-dione-quinoline-4,6-dione (I)

Indoline-7-carboxylic acid (G. M. Coppola, S. Palermo, J. Heterocyclic Chem. 1986, 23, 971) is dissolved in 0.5N hydrochloric acid and phosgene is bubbled through for 2 hr at 0°. The reaction is filtered and recrystallized form acetonitrile/toluene to afford the title compound, mp 234°–235°. [lit. m.p. 236°–239° dec.]

PREPARATION 124

1-(1,1-Dimethylethoxy)carbonyl-4-methylaminopiperidine

Methylamine hydrochloride (2.36 g) is dissolved in methanol (50 ml) and potassium hydroxide pellets (0.60 g) and N-(1,1-di-methylethoxycarbonyl)-4-piperidone are added. Sodium cyanoborohydride (0.69 g) in methanol (5 ml) is added and the mixture is stirred 2 hrs. Potassium hydroxide pellets (1.96 g) are added to the mixture which is stirred 1 hr and acidified to pH 2 with 6M hydrochloric acid and concentrated. The mixture is diluted with water (50 ml) and extracted with ether (3×80 ml) which is discarded. The aqueous layer is basified to pH 11 with potassium hydroxide pellets, saturated with sodium chloride and extracted with ether (6×80 ml). The combined organic extracts are dried with magnesium sulfate and concentrated to afford an oil which is chromatographed on silica gel with a methanol/chloroform gradient (5–30%). Fractions are pooled on the basis of TLC ($R_f$=0.13, 20% methanol/chloroform) to give the title product, NMR (CDCl$_3$) 4.04, 2.79, 2.54, 2.46, 2.33, 1.88, 1.46, and 1.26δ.

PREPARATION 125

1-(1,1-Dimethylethoxy)carbonyl)-4-(N-methyl-N-(3-nitro-2-pyridinyl)amino)piperidine Anhydrous potassium carbonate (2.71 g) and 2-chloro-3-nitropyridine (0.93 g) are added to a solution of 1-((1,1-dimethylethoxy)carbonyl)-4-methylaminopiperidine (PREPARATION 124) (1.40 g) in acetonitrile (50 ml). The mixture is stirred 21 hours at 20°–25° and additional 2-chloro-3-nitropyridine (100 mg) and acetonitrile (5 ml) are added. The mixture is stirred 2.8 days, concentrated and dissolved in methylene chloride (175 ml) and water (50 ml). The phases are separated and the organic phase is extracted with water (2×50 ml) and saline (40 ml) and dried over sodium sulfate. Concentration under reduced pressure affords an oil which is chromatographed on silica gel (120 g) eluting with 10% ethyl acetate/hexane. Fractions with $R_f$=0.29 by TLC (silica gel, 25% ethylacetate/haxane) are pooled and concentrated to give the title compound, NMR (CDCl$_3$) 8.29, 8.11, 6.68, 4.62, 4.26, 2.85, 2.67 and 1.48δ.

PREPARATION 126

4-(N-methyl-N-(3-nitro-2-pyridinyl)amino)piperidine

Trifluoroacetic acid (13.0 ml) is added to a solution of 1-((,11-dimethylethoxy)carbonyl)-4-(N-methyl-N-(3-nitro-2-pyridinyl)amino)piperidine (PREPARATION 125) in methylene chloride (100 ml) with cooling to −78°. The mixture is warmed to 20°–25°, stirred 17 hrs, cooled to 0° and basified to pH 12 with 5% sodium hydroxide. The phases are separated and the aqueous phase is extracted with methylene chloride (2×50 ml). The combined organic phases are dried over sodium sulfate and concentrated to give the title compound, mp 115.5°–117°.

PREPARATION 127

1-(indolyl-2-carbonyl)-4-(N-methyl-N-(3-nitro-2-pyridinyl)amino)piperidine (II)

Following the general procedure of PREPARATION 35 and making non-critical variations but starting with 4-(N-methyl-N-(3-nitro-2-pyridinyl)amino)piperidine (PREPARATION 126) the title compound is obtained, mp 228°–229.5°.

PREPARATION 128

5-Azaindole-2-carboxylic acid

Following the general procedure of PREPARATION 42 and making non-critical variations employing 5-azaindole, the title compound is obtained.

PREPARATION 129

1-[5-Fluoroindolyl-2-carbonyl]-4-[3-amino-2-pyridinyl]piperazine

Following the general procedure of PREPARATION 22 and making non-critical variations but starting with 1-[5-fluoroindolyl-2-carbonyl]-4-[3-nitro-2-pyridinyl]piperazine (PREPARATION 17), the title compound is obtained.

Example 1

1-[4-Methoxy-3,5-dimethylbenzoyl]-4-[3-(ethylamino)-2-pyridinyl]piperazine (IV)

3,5-Dimethyl-4-methoxybenzoic acid (I, PREPARATION 3, 0.36 g) is added to a solution of 1,1'-carbonyldiimidazole (0.33 g) in tetrahydrofuran (4 ml) at 20°–25°. After one hour of stirring, 4-[3-(ethylamino)-2-pyridinyl]piperazine (II, International Publication No WO 87/01706 based on International Patent application No PCT/US86/01797, PREPARATION A-47, 0.42 g) in tetrahydrofuran (6 ml) is added and the solution is stirred for 18 hours. The mixture is diluted with dichloromethane and a saturated aqueous sodium bicarbonate solution. The phases are separated, the organic phase is washed with water, then with saline and the phases are separated. The organic phase is dried over sodium sulfate and concentrated under reduced pressure to give an oil. The oil is flash chromatographed on silica gel (230–400 mesh), the product eluted with chloroform, the appropriate fractions are pooled and concentrated to give the title compound.

The title compound is treated with ethereal hydrochloric acid, and the resulting oil is solidified by dissolving in acetone (6 ml) and adding drop by drop to ether (500 ml). The solid precipitate is collected and dried in a vacuum oven at 70° to give the hydrochloride salt of the title compound, analysis calcd for $C_{21}H_{28}N_4O_2 \cdot 6HCl \cdot 4H_2O$ (C, 64.45; H, 7.40; N, 14.31; Cl, 5.44) found C, 64.62; H, 7.45; N, 14.49; Cl, 5.33.

Example 3

1-[4-Methoxy-3,5-dimethylbenzyl]-4-[3-(ethylamino)-2-pyridinyl]piperazine (IV)

Following the general procedure of EXAMPLE 1 and making non-critical variations but starting with 3,5-dimethyl-4-methoxybenzyl chloride (I, PREPARATION 4, 3.70 g), the title compound is obtained.

Following the general procedure of EXAMPLE 1 and making non-critical variations the title compound is converted to its hydrochloride salt which is recrystallized from a methanol/ether mixture, mp. 214°–216°.

Example 4

1-[4-Hydroxy-3,5-dimethylbenzyl]-4-[3-(ethylamino)-2-pyridinyl]piperazine (IV)

Following the general procedure of EXAMPLE 1 and making non-critical variations but starting with 3,5-dimethyl-4-hydroxybenzyl chloride (I, PREPARATION 5, 1.6 g), the title compound is obtained.

Following the general procedure of EXAMPLE 1 and making non-critical variations the title compound is converted to its hydrochloride salt which is recrystallized from methanol/ether, mp. 203°–206°.

Example 5

1-[4-Methoxy-3,5-dimethylbenzyl]-4-[3-(propylamino)-2-pyridinyl]-piperazine (IV)

Following the general procedure of EXAMPLE 1 and making non-critical variations but starting with 3,5-dimethyl-4-methoxybenzyl chloride (I, PREPARATION 4, 0.41 g) and 1-[3-(propylamino)-2-pyridinyl]piperazine (II, PREPARATION 7, 0.42 g), the title compound is obtained.

Following the general procedure of EXAMPLE 1 and making non-critical variations, the hydrochloride salt of the title compound is obtained, which is recrystallized from acetone/ether, mp 223°–225°.

Example 7

1-[4-Methoxybenzyl]-4-[3-(ethylamino)-2-pyridinyl]piperazine (IV)

A solution of 1-[4-Methoxyphenyl-1-carbonyl]-4-[3-(ethylamino)-2-pyridinyl]piperazine (III, PREPARATION 18, 1.5 g) in tetrahydrofuran (20 ml) is added dropwise to a suspension of lithium aluminum hydride (0.35 g) in tetrahydrofuran (15 ml) at 20°–25°. The mixture is stirred for 20 hours. The reaction is quenched by sequential addition of water (0.35 ml), aqueous sodium hydroxide (15%, 0.35 ml) and water (1.05 ml). The mixture is filtered, and the filtrate is concentrated under reduced pressure to an oil. The oil is flash chromatographed on silica gel, eluting with chloroform. The appropriate fractions are pooled and concentrated to give the title compound.

The hydrochloride salt of the title compound is prepared by dissolving the title compound in ether and treating it with ethereal hydrogen chloride. The salt is recrystallized from acetone/ether, mp. 189°–190°; MS (high resolution) calculated for $C_{19}H_{26}N_4O_1$ (326.2106), found 326.2106.

Example 10

1-[Indolyl-2-carbonyl]-4-[2-ethoxyphenyl]piperazine (X)

1,1'-carbonyldiimidazole (1.30 g) is added to a 20°–25° solution of indole-2-carboxylic acid (I, 1.17 g) in tetrahydrofuran (14 ml). After one hour of stirring, the reaction is cooled to 0° and a solution of 1-(2-ethoxyphenyl)piperazine (II, 1.50 g) in tetrahydrofuran (7 ml) is added via cannula. After 30 minutes at 0°, the reaction is warmed to 20°–25° and stirred 18 hours. Ddichloromethane (100 ml) is added and the mixture is washed with saturated aqueous sodium bicarbonate, dried over anyhydrous sodium sulfate and concentrated under reduced pressure. The residue is purified by flash column chromatography (2 cm×20 cm) eluting with 100% chloroform. The appropriate fractions are pooled and concentrated to give the title compound.

The title compound is dissolved in methanol and treated with ethereal hydrochloric acid. The precipitated salt is recrystallized from ether/methanol to give the hydrochloride salt of the title compound, mp. 205°–208°.

Example 11

1-[Indolyl-2-carbonyl]-4-[3-(ethylamino)-2-pyridinyl]piperazine (III)

1,1'-Carbonyldiimidazole (0.825 g) is added to a 20°–25° solution of indole-2-carboxylic acid (I, 0.78 g) in tetrahydrofuran (10 ml). After one hour of stirring, 1-(3-ethylamino-2-pyridinyl)piperazine (II, 1.0 g) in tetrahydrofuran (5 ml) is added via cannula at 0°. After 15 minutes at 0°, the reaction is warmed to 20°–25° and stirred 20 hours. It is then diluted with ether (75 ml), washed with saline (75 ml), and dried over anhydrous sodium sulfate. After concentration under reduced pressure, the residue is purified by flash column chromatography (2 cm×20 cm) eluting with methanol/chloroform (2/98). The appropriate fractions are pooled and concentrated. The solid is further purified by recrystallization (ethyl acetate/hexane) to give the title compound, mp. 138°–139°.

The title compound is dissolved in methanol and treated with ethereal hydrochloric acid. The precipitated salt is recrystallized from ether/methanol to give the hydrochloride salt of the title compound, mp 218°–219°.

Example 12

1-[5-Methoxyindolyl-2-carbonyl]-4-[2-ethoxyphenyl]piperazine (IV)

1,1'-Carbonyldiimidazole (1.30 g) is added to a 20°–25° solution of 5-methoxyindole-2-carboxylic acid (I, 1.39) in tetrahydrofuran (14 ml). The reaction is stirred one hour, then cooled to 0° and 1-(2-ethoxyphenyl)piperazine (II, 1.50 g) dissolved in tetrahydrofuran (7 ml) is added via cannula. The reaction is warmed to 20°–25° and stirred 48 hours. The reaction is diluted with ether (100 ml), poured into saturated aqueous sodium bicarbonate (100 ml). The organic layers are separated and washed with saline (100 ml), dried over anhydrous sodium sulfate and concentrated under reduced pressure. The residue is recrystallized from toluene to give the title compound, mp. 105°–107°.

Example 16

1-[5-Methoxyindolyl-2-carbonyl]-4-[3-(ethylamino)-2-pyridinyl]piperazine (IV)

1,1'-Carbonyldiimidazole (0.55 g) is added to a 20°–25° solution of 5-methoxyindole-2-carboxylic acid (I, 0.59 g) in tetrahydrofuran (7.0 ml). After stirring 1 hour, the reaction is transferred via cannula into a solution of 1-(3-N-ethylamino-2-pyridinyl)piperazine (II, 0.70 g) in tetrahydrofuran (7 ml) at −12° (ice/acetone bath). The reaction is stirred at −10° for 30 minutes, then slowly warmed to 20°–25° and stirred a further 18 hours. After diluting with ether (60 ml), the mixture is washed with saturated aqueous sodium bicarbonate (70 ml), saline (70 ml) and dried over anhydrous sodium sulfate. The mixture is concentrated under reduced pressure to a residue which is purified by flash chromatography (2 cm×20 cm) eluting with methanol/chloroform (2/98) to give the title compound, mp 153°–154°.

Example 16A

1-[5-Methoxyindolyl-2-carbonyl]-4-[3-(ethylamino)-2-pyridinyl]-piperazine, hydrochloride (IV)

1-(Ethyl)-3-(dimethylaminopropyl)carbodiimide (1.25 g) is added to a solution of 1-(3-ethyl-2-pyridinyl)piperazine (1.12 g) in THF (15 ml). The reaction is stirred at 20°–25° for 3 hr, then it is dissolved in chloroform (50 ml) and extracted with saturated aqueous sodium bicarbonate, saline, dried over anhydrous sodium sulfate and concentrated under reduced pressure. Purification by flash column chromatography (200 g silica) eluting with ethyl acetate/hexane (50/50), the appropriate fractions are pooled and concentrated to give the title compound. The product is dissolved in methanol (150 ml) with heating, cooled to 20°–25° and chlorotrimethylsilane (4.70 mmol) is added. The mixture is concentrated to half-volume, ether is added until cloudy and the flask is stored at 0° overnight. Filtration gives the hydrochloride salt, mp 194°–195°. CMR (300 MHz, CDCl$_3$) 165.2, 155.9, 146.1, 144.8, 133.4, 130.5, 128.9, 125.6, 122.6, 116.7, 113.9, 106.5, 103.3, 56.3, 39.1 and 14.2 δ.

The mesylate salt is formed by dissolving the free base in methanol and methanesulfonic acid (1 eq) is added. The solution is diluted with diethyl ether until the salt crystallizes out of solution. The crystals are collected and dried to afford the mesyl salt of the title compound, mp 215°–216°, CMR (300 MHz, CD$_3$OD) 165.22, 156.03, 146.23, 141.75, 133.35, 130.6, 129.0, 125.7, 123.5, 122.5, 166.6, 113.9, 106.5, 103.2, 56.2, 45.7, 39.7, 39.0 and 14.1 δ.

Example 17

1-[Indolyl-2-carbonyl]-4-[3-(1-methylethylamino)-2-pyridinyl]piperazine (III)

Following the general procedure of EXAMPLE 1 and making non-critical variations but starting with indole-2-carboxylic acid (I) and 1-[3-(1-methylethylamino)-2-pyridinyl]piperazine (II, PREPARATION 9, 0.19 g), the title compound is obtained, mp 151°–152°.

Example 19

1-[Indolyl-2-carbonyl]-4-[3-(N,N-diethylamino)-2-pyridinyl]-piperazine (III)

1-[Indolyl-2-carbonyl]-4-(3-amino-2-pyridinyl)piperazine (III, PREPARATION 22, 0.10 g) is dissolved in methanol (2.5 ml) and cooled to 0°. Acetaldehyde (0.041 g) and acetic acid (5 drops) are added. After 15 minutes of stirring sodium cyanoborohydride (0.04 g) is added. The reaction is slowly warmed to 20°–25° and acetaldehyde is added at 1 hour intervals (5×0.041 g). Stirring is continued 18 hours at 20°–25°. Then the reaction is diluted with dichloromethane (20 ml), washed with saturated aqueous sodium bicarbonate (20 ml) and saline (20 ml). The organic layer is dried over anhydrous sodium sulfate and concentrated under reduced pressure. Purification by flash column chromatography (methylene chloride), pooling the appropriate fractions and concentrating them give the title compound, mp 173°–174°; MS (m/e) 378, 377, 348, 205, 204, 178, 176, 162 and 144.

Example 20

1-[Indolyl-2-methyl]-4-[3-(ethylamino)-2-pyridinyl]piperazine (III)

Lithium aluminum hydride (0.011 g) is added to ether (1 ml) at 0°. 1-(2-Indolylcarbonyl)-4-[3-(ethylamino-2-pyridinyl)piperazine (III, EXAMPLE 11, 0.10 g) is added portionwise. After the addition is complete the reaction is stirred at 20°–25° for 18 hours. The reaction is quenched at 0° by the dropwise addition of water (0.2 ml), aqueous sodium hydroxide (15%, 0.1 ml), and water (9.5 ml). The resulting slurry is filtered through a pad of celite and sodium sulfate and concentrated under reduced pressure. The concentrate is purified by flash column chromatography (8 g silica gel), eluting with ethyl acetate/hexane (1/1). The appropriate fractions are pooled and concentrated to give the title compound, NMR (300 MHz, CDCl$_3$) 8.68, 7.71, 7.56, 7.35, 7.15, 7.08, 6.90, 6[.80, 6.38, 4.16, 3.10, 2.65 and 1.29 δ.

Example 21

1-[5-Fluoroindolyl-2-carbonyl]-4-[3-(propylamino)-2-pyridinyl]piperazine (III)

1,1'-carbonyldiimidazole (0.48) is added to a 20°–25° solution of 5-fluoroindole-2-carboxylic acid (I, 0.53 g) in THF (6 ml). After 1 hour of stirring the above reaction is added dropwise via cannula to a solution of [3-(propylamino)-2-pyridinyl]piperazine (II, PREPARATION 7, 0.72 g) in THF (6 ml) at −10° (ice/acetone bath). The reaction is stirred for 30 minutes at −10°, slowly warming to 20°–25°, and stirred 4 hours. The reaction is diluted with dichloromethane (50 ml), washed with saturated aqueous sodium bicarbonate (40 ml), saline (40 ml), dried over anhydrous sodium sulfate and concentrated under reduced pressure. The concentrate is purified by flash column chromatography (40 g silica gel) eluting with ethyl acetate/hexane (1/1). The appropriate fractions are pooled and concentrated to give the title compound, mp 196°–198°; IR (mineral oil) 3200, 2920–3000, 1630 and 1424 cm$^{-1}$; NMR (300 MHz, CDCl$_3$) 9.82, 7.72, 7.35, 7.27, 7.03, 6.95, 6.86, 6.78, 4.32, 4.09, 3.21, 3.08, 1.71 and 1.05 δ; CMR (300 MHz, CDCl$_3$) 162.3, 159.5, 149.7, 137.4, 135.1, 132.3, 130.7, 127.5, 127.4, 120.4, 116.3, 113.4, 112.9, 112.7, 112.5, 106.1, 105.8, 105.1, 105.0, 49.0, 45.2, 22.5 and 11.6 δ; MS (m/e) 382, 381, 190, 176, 164, 162, 134 and 120.

Example 22

1-[5-Chloroindolyl-2-carbonyl]-4-[3-(ethylamino)-2-pyridinyl]piprazine (III)

1,1'-carbonyldiimidazole (0.42 g) is added to a 20°–25° solution of 5-chloroindole-2-carboxylic acid (I, 0.5 g) in THF (5 ml). After 1 hour of stirring at 20°–25°, the above reaction is added dropwise over 10 minutes via cannula to a −10° (ice/acetone bath) solution of [3-(ethylamino)-2-pyridinyl]piperazine (II, 0.58 g) in THF (5 ml). After 30 minutes of stirring at −10°, the reaction is warmed to 20°–25° and stirring is continued for 5 hours. The reaction is diluted with dichloromethane (50 ml), washed with saturated aqueous sodium bicarbonate (40 ml), water (40 ml) and saline (40 ml). The organic layers are dried over anhydrous sodium sulfate and concentrated under reduced pressure. The concentrate is purified by flash column chromatography (50 g silica gel), eluting with ethyl acetate/hexane (1/1). The appropriate fractions are pooled and concentrated to give the title compound, mp 208°–209°; IR (mineral oil) 3200, 2920–3000, 1632, and 1425 cm$^{-1}$; NMR (300 MHz, CDCl$_3$) 9.77, 7.72, 7.60, 7.36, 7.22, 6.97, 6.86, 6.75, 4.23, 4.09, 3.23–3.15, and 1.33 δ; MS (m/e) 383, 178, 176, 162, 150, 148, 137, 134, and 120.

Example 23

1-[5-Fluoroindolyl-2-carbonyl]4-[3-(ethylamino)-2-pyridinyl]-piperazine (III)

1,1'-carbonyldiimidazole (0.55 g) is added to a 20°–25° solution of 5-fluoroindole-2-carboxylic acid (I, 0.55 g) in THF (7 ml). After 1 hour the above reaction is added dropwise via cannula over 10 minutes to a −12° (ice/acetone bath) solution of [3-(ethylamine)-2-pyridinyl)]piperazine (0.70 g) in THF (7 ml). The reaction is stirred 30 minutes at −12° and then slowly allowed to warm to 20°–25°. After 18 hours of stirring, the reaction is diluted with ether (50 ml), washed with saturated aqueous sodium bicarbonate (50 ml), saline (50 ml), dried over anhydrous sodium sulfate and concentrated under reduced pressure. The concentrate is purified by flash column chromatography (4 cm column), eluting with methanol/chloroform (5/95). The appropriate fractions are pooled and concentrated to give the title compound, mp 187°–188°.

Example 24

1-[5-Ethylindolyl-2-carbonyl]-4-[3-(ethylamino)-2-pyridinyl]piperazine (III)

1,1'-carbonyldiimidazole (0.43 g) is added to a 20°–25° solution of 5-ethylindole-2-carboxylic acid (I, 0.5 g) in THF (5 ml). After 1 hour the above reaction is added via cannula over 10 minutes to a −10° solution of [3-ethylamino-2-pyridinyl]piperazine (II, 0.56 g) in THF (5 ml). The reaction is slowly allowed to warm to 20°–25° and stirred 5 hours. The reaction is diluted with dichloromethane (30 ml), washed with saturated aqueous sodium bicarbonate (40 ml), water (40 ml) and saline (40 ml). The organic layer is dried over anhydrous sodium sulfate and concentrated under reduced pressure. The concentrate is purified by flash column chromatography (50 g silica gel), eluting with ethyl acetate/hexane (1/2). The appropriate fractions are pooled and concentrated to give the title compound, mp 174°–176°; IR (mineral oil) 3371, 2920–3000, 1609, and 1536 cm$^{-1}$; NMR (300 MHz, CDCl$_3$) 9.23, 7.72, 7.45, 7.35, 7.15, 6.96, 6.86, 6.76, 4.23, 4.08, 3.22–3.19, 2.74, 1.33, and 1.28 δ; MS (m/e) 378, 377, 176, 172, 163, 162, 150, 148, and 137.

Example 25

1-[5-Fluoroindolyl-2-carbonyl]-4-[3-(1-methylethylamino)-2-pyridinyl] piperazine (III)

1,1'-carbonyldiimidazole (0.147 g) is added to a 20°–25° solution of 5-fluoroindole-2-carboxylic acid (I, 0.163 g) in THF (2.5 ml). After 1 hour of stirring at 20°–25°, the reaction is cooled to 0° and [3-(1-methylethylamino)-2-pyridinyl]piperazine (II, PREPARATION 9, 0.20 g) dissolved in THF (0.75 ml) is added. The reaction is allowed to warm to 20°–25° and stirred for 18 hours. Then the reaction is diluted with methylene chloride (15 ml) and washed with saturated aqueous sodium bicarbonate (15 ml), water (15 ml) and saline (15 ml). The organic layer is dried over anhydrous sodium sulfate and concentrated under reduced pressure to afford the desired product. The product is purified by flash column chromatography (8 g silica gel), eluting with hexane/ethyl acetate (2/1). The appropriate fractions are pooled and concentrated to give the title compound, mp 201°–203°.

Example 26

1-[5-Methoxyindolyl-2-carbonyl]-4-[3-(1-methylethylamino)-2-pyridinyl]piperazine (IV)

1,1'-carbonyldiimidazole (0.147 g) is added to a room temperature solution of 5-methoxyindole-2-carboxylic acid (I, 0.174 g) in THF (3.6 ml). After stirring for 1 hour at 20°–25°, the reaction is cooled to 0° and [3-(1-methylethylamino)-2-pyridinyl]piperazine (II, PREPARATION 9, 0.20) dissolved in THF (0.75 ml) is added. The reaction is allowed to warm to 20°–25° and stirred 18 hours. Then the reaction is diluted with methylene chloride (15 ml) and washed with saturated aqueous sodium bicarbonate (15 ml), water (15 ml) and saline (15 ml). The organic layer is dried over anhydrous sodium sulfate and concentrated under reduced pressure to a concentrate. The concentrate is purified by flash column chromatography (8 g silica gel), eluting with hexane/ethyl acetate (2/1). The appropriate fractions are pooled and concentrated to give the title compound, mp 167°–168°.

Example 27

1[Benzofuroyl-2-carbonyl]-4-[3-(ethylamino)
-2-pyridinyl]piperazine (III)

Following the general procedure of EXAMPLE 16 and making non-critical variations but using benzofuran-2-carboxylic acid (I, 0.5 g), the title compound is obtained, MS (high resolution) calculated for $C_{20}H_{22}N_4O_2$ (350.1743), found 350,1747.

Example 28

1-[5-Methoxyindolyl-2-carbonyl]-4-[2-
(ethylamino)phenyl]piperazine (IV)

Following the general procedure of EXAMPLE 16 and making non-critical variations but using 1-(2-ethylaminophenyl)piperazine (II, PREPARATION 15, 0.881 g), the title compound is obtained, mp 190°; HRMS=378.2061 (Calcd. for $C_{22}H_{26}N_4O_2$ is 378.2056).

Example 29

1-[Indolyl-2-carbonyl]-4-[2-(ethylamino)
phenyl]piperazine (III)

Following the general procedure of EXAMPLE 16 and making non-critical variations but using indole-2-carboxylic acid (I, 0.75 g) and 1-(2-ethylaminophenyl)piperazine (II, PREPARATION 15, 1.06 g), the title compound is obtained, mp 184°–185°; HRMS=348.1948 (Calcd for $C_{21}H_{24}N_4O$ is 348.1950).

Example 31

1-[Indolyl-2-carbonyl]-4-[3-
(cyclopropylmethylamino)-2-pyridinyl] piperazine
(III)

1-[Indolyl-2-carbonyl]-4-(3-amino-2-pyridinyl)piperazine (PREPARATION 22, 0.12 g) is dissolved in methanol (2 ml) and cyclopropylcarboxaldehyde (0.028 ml) is added. The reaction mixture is cooled to 0° and 5 drops of acetic acid are added. After 15 min, sodium cyanoborohydride (0.026 g) is added and the reaction mixture is allowed to warm to 20°–25°. After 3 hr, the reaction is diluted with methylene chloride, washed with saturated aqueous sodium bicarbonate, dried over sodium sulfate and concentrated under reduced pressure. The concentrate is purified by flash chromatography eluting with ethyl acetate/hexane (25/75). The appropriate fractions are pooled and concentrated to give the title compound, mp 157°–158°.

Example 32

1-[5-Fluoroindolyl-2-methyl]-4-[3-
(1-methylethylamino)-2-pyridinyl]piperazine (III)

Following the general procedure of EXAMPLE 20 and making non-critical variations but starting with 1-[(5-fluoroindolyl)carbonyl]-4-[3-(1-methylethylamino)-2-pyridinyl]piperazine (III, EXAMPLE 25), the title compound is obtained.

Example 33

1-[Indolyl-2-carbonyl]-4-[3-2,2,2-
trifluoroethylamino)-2-pyridinyl]piperazine (III)

Following the general procedure of EXAMPLE 16A and making non-critical variations but starting with 5-fluoroindole-2-carboxylic acid and 1-[3-(2,2,2-trifluoroethylamino)-2-pyridinyl]piperazine (PREPARATION 103), the title compound is obtained.

Example 34

1-[5-Fluoroindolyl-2-carbonyl]-4-[3-(2,2,2-
trifluoroethylamino)-2-pyridinyl]piperazine (III)

Following the general procedure of EXAMPLE 16A and making non-critical variations but starting with 5-fluoroindole-2-carboxylic acid and 1-[3,-(2,2,2-trifluoroethylamino)-2-pyridinyl]piperazine (PREPARATION 103), the title compound is obtained, NMR (300 MHz, $CDCl_3$) 9.35, 7.87, 7.45, 7.27, 7.19–6.97, 6.77, 5.05, 4.11, 3.83, and 3.30 δ.

Example 35

1-[5-Benzyloxyindolyl-2-carbonyl]-4-[3-(ethylamino)-
2-pyridinyl]piperazine (III)

Following the general procedure of EXAMPLE 16 and making non-critical variations but starting with 5-benzyloxyindole-2-carboxylic acid (1.0 g), 1-(3-ethylamino-2-pyridinyl)piperazine (International Publication WO 87/01706, 0.81 g), 1,1'-carbonyldiimidazole (0.61 g) and THF (7 ml), the title compound is obtained, mp 192°–193°.

Example 36

1-[5-Benzyloxyindolyl-2-carbonyl]-4-[3-
(1-methylethyl)amino-2-pyridinyl]piperazine (III)

5-Benzyloxyindole-2-carboxylic acid (131 mg) and 1,1'-carbonyldiimidazole (96 mg) are dissolved in dry THF (2 ml) and stirred for 2 hr at 20°–25°. The resulting solution is added via canula to a −10° cooled solution of 1-[3-1-methylethyl)amino-2-pyridinyl]piperazine (PREPARATION 9, 121 mg) in dry THF (2 ml). The reaction mixture is then allowed to reach 20°–25° overnight. The reaction mixture is then diluted with ethyl acetate, washed with saturated sodium bicarbonate and water, dried over magnesium sulfate, and concentrated to give an oil. Purification of this oil on a silica gel flash column eluting with hexane/ethyl acetate (1/1), the appropriate fractions are pooled and concentrated to give the title compound. Recrystallization from ethyl acetate/methylene chloride gives the purified title compound, mp 147°–148°.

Example 37

1-[5-Hydroxyindolyl-2-carbonyl]-4-[3-(ethylamino)-2-pyridinyl]piperazine (IV)

1-[5-Benzyloxycarbonylindolyl-2-carbonyl]-4-[3-(ethylamino)-2-pyridinyl]piperazine (EXAMPLE 35, 0.25 g) is dissolved in methanol (30 ml) and then palladium on carbon (10%, 0.10 mg) and ammonium formate (0.05 g) are added. The reaction is stirred at 20°–25° for 4 hr and then filtered through celite and concentrated. Then the reaction is dissolved in methanol/chloroform (10/90) and washed with water (2 ×), dried anhydrous sodium sulfate and concentrated under reduced pressure. The product is purified by recrystallization from ethyl acetate/hexane to give the title compound, mp 216°–217°.

Example 38

1-[5-Hydroxyindolyl-2-carbonyl]-4-[3-(1-methylethylamino)-2-pyridinyl]piperazine (IV)

Following the general procedure of EXAMPLE 37 and making non-critical variations but starting with 1-[5-benzyloxyindolyl-2-carbonyl]-3-(1-methylethylamino)-2-pyridinyl]piperazine (EXAMPLE 36), the title compound is obtained, mp 254°–257°.

Example 39

1-[Indolyl-2-methyl]-4-[3-(1-methylethylamino)-2-pyridinyl]piperazine (III)

Following the general procedure of EXAMPLE 20 and making non-critical variations but starting with 1-[indolyl-2-carbonyl]-4-[3-(1-methylethylamino)-2-pyridinyl]piperazine (III, EXAMPLE 17), the title compound is obtained.

Example 42

1-[5-Methoxy-4,6,7-trimethylindolyl-2-carbonyl]-4-[3-(ethylamino)-2-pyridinyl]piperazine (IV)

Following the general procedure of EXAMPLES 1 and 16 and making non-critical variations but starting with 5-methoxy-4,6,7-trimethylindole-2-carboxylic acid (I, PREPARATION 20), the title compound is obtained, mp 166°–168°.

Example 44

1-[Indolyl-2-carbonyl]-4-[3-(1,1-dimethylethylamino)-2-pyridinyl]piperazine (III)

1-Ethyl-3-(3-dimethylaminopropyl)carbodiimide hydrochloride (45 mg) is added to a 20°–25° solution of indole-2-carboxylic acid (35 mg) and 1-[3-(1,1-dimethylethylamino)-2-pyridinyl]piperazine (PREPARATION 21, 50 mg) in tetrahydrofuran (3 ml). After stirring 1 hr, the solution is diluted with water and extracted with methylene chloride (3×). The combined extracts are washed with saline, dried over anhydrous sodium sulfate, filtered, and concentrated under reduced pressure. The resulting solid is flash chromatographed (silica gel, 230–400 mesh), eluting with methanol/methylene chloride (1/25); the appropriate fractions are pooled and concentrated to give the title compound, as an oil. The PMR, CMR, IR, and mass (M+377) spectra support the desired compound.

The title compound is dissolved in methanol and treated with ethereal hydrochloric acid. The precipitated salt is collected by filtration and dried in vacuo to give the hydrochloride salt of the title compound, mp 175°–190°.

Example 45

1-[5-Methoxyindolyl-2-carbonyl]-4-[3-(1,1-dimethylethylamino)-2-pyridinyl]piperazine hydrochloride salt (IV)

Following the general procedure of EXAMPLE 44 and making non-critical variations but starting with 5-methoxyindole-2-carboxylic acid (204 mg), 1-(ethyl)-3-(dimethylaminopropyl)carbodiimide (224 mg), the title compound is obtained, mp 119°–121°; MS (m/e) 407.

Example 46

1-[5-Fluoroindolyl-2-carbonyl]-4-[3-(1,1-dimethylethylamino)-2-pyridinyl]piperazine hydrochloride salt (III)

Following the general procedure of EXAMPLE 44 and making non-critical variations but starting with 5-fluoroindole-2-carboxylic acid (88 mg), the title compound is obtained, mp 168°–178°; MS (m/e) 395.

Example 47

1-(5-Fluoroindolyl-2-carbonyl)-4-[3-(1-methylethylamino)-2-pyrazinyl]piperazine (III)

Following the general procedure of EXAMPLE 16 and making non critical variations but starting with indole-2-carboxylic acid (0.215 g), 1,1'-carbonyldiimidazole (0.20 g) and 1-[2-(1-methylethylamino-3-pyrazinyl]piperazine (PREPARATION 25, 0.32 g) in THF (5 ml). The product is chromatographed eluting with methanol/chloroform (1/99). The appropriate fractions are pooled and concentrated to give the title compound.

The title compound is treated with ethereal hydrochloric acid, the hydrochloride salt is recrystallized from methanol/ether to give salt of the title compound, mp 251°–252°.

Example 48

1-(5-Fluoroindolyl-2-carbonyl)-4-[5-(1-methylethylamino)-4-pyrimidinyl]piperazine (III)

Following the general procedure of EXAMPLE 16 and making non-critical variations but starting with 5-fluoroindole-2-carboxylic acid (0.179 g) and 1-[5-(1-methylethylamino)-4-pyrimidinyl]piperazine (PREPARATION 30, 0.24 g), the title compound is obtained.

The free amine is treated with ethereal hydrochloric acid. The hydrochloride salt is recrystallized from ethanol/ether to give the salt of the title compound, mp 288°–289°.

Example 49

1-(Indolyl-2-carbonyl)-4-[4-(1-methylethylamino)-3-pyridazinyl]piperazine, methane sulfonate (III)

Following the general procedure of EXAMPLE 16 and making non-critical variations but starting with indole-2-carboxylic acid (0.48 g) and 1-[4-(1-methylethylamino)-3-pyridazinyl]piperazine (PREPARATION 33), the title compound is obtained.

Example 50

1-(5-Fluoroindolyl-2-carbonyl)-4-[4-(1-methylethyl) amino)-3-pyridazinyl]piperazine, methane sulfonate (III)

Following the general procedure of EXAMPLE 16 and making non-critical variations but starting with 5-fluoroindole-2-carboxylic acid (0.53 g) and 1-[4-(1-methylethylamino)-3-pyridazinyl]piperazine (PREPARATION 33, 3.0 mmol), a solid is obtained which is recrystallized from ethyl acetate to give the title compound.

The free base is treated with and ethanolic solution of methanesulfonic acid (0.21 g) and recrystallized from ethanol to give the salt of the title compound, mp 215°–217°.

Example 51

1-[5-Fluoroindolyl-2-carbonyl]-4-[3-(1,1-dimethylethylamino)-2-pyrazinyl]piperazine Following the general procedure of EXAMPLE 16 and making non-critical variations but starting with 5-fluoroindole-2-carboxylic acid (0.44 g) and 3-(1,1-dimethylethylamino)-2-pyrazinylpiperazine (2.50 mmol), a solid is obtained which is recrystallized from ethyl acetate to give the title compound.

The free base (0.5 g) is treated with and ethanolic solution of methanesulfonic acid (0.13 g) and recrystallized from ethanol/ethyl acetate/hexane to give the salt of the title compound, mp softens at 130–155, then melts at 175°.

Example 52

N,N'-Dimethyl-N-(indolyl-2-carbonyl)-N'-(3-(1-methylethylamino) pyrid-2-yl)ethylenediamine (III)

Palladium black (100 mg) is added to a solution of N,N'-dimethyl-N-(indolyl-2-carbonyl-N'-(3-nitro-2-pyridinyl)ethylendiamine (PREPARATION 35, 150 mg) in methanol (20 ml) and acetone (10 ml). The mixture is stirred one hour under a hydrogen atmosphere (balloon), filtered and concentrated. The residue is dissolved in methanol (4 ml) and acetone (1 ml) and treated with sodium cyanoborohydride (31 mg) and enough acetic acid to give pH 5 on moistened indicator paper. The mixture is stirred 5.25 hr at 20°–25°, concentrated to dryness and partitioned between methylene chloride (30 ml) and saturated potassium carbonate (10 ml). The phases are separated, the organic phase is extracted with the base (10 ml) and dried over sodium sulfate. Removal of solvent under reduced pressure gives the crude product. The crude product is chromatographed on a bed of silica gel (40 ml) eluting with ethyl acetate/hexane (50/50), pooling and concentrating the appropriate fractions on the basis of TLC (ethyl acetate/silica gel) gives the title compound; NMR (CDCl$_3$) 9.97, 7.71, 7.63, 7.44, 7.26, 7.12, 6.90, 6.85, 6.78, 4.25, 3.82, 2.74, and 1.13$\delta$.

Example 53

N,N'-Dimethyl-N-(indolyl-2-carbonyl)-N'-[3-(1-methylethyl-amino)-2-pyridyl]-1,3-propanediamine (III)

Following the general procedure of PREPARATIONS 34 and 35, and EXAMPLE 52, making non-critical variations but starting with N,N'-dimethyl-1,3-propanediamine, and recrystallizing from chloroform/ethyl ether gives the title compound, mp 123.5°–124.5°, decomp.

Example 54

N,N'-Dimethyl-N-(indolyl-2-carbonyl)-N'-[3-(1-methylethyl-amino)-2-pyridinyl]-1,6-hexanediamine (III)

Following the general procedure of PREPARATIONS 34 and 35, and EXAMPLE 52, making non-critical variations but starting with N,N'-dimethyl-1,6-hexanediamine, and recrystallizing from chloroform/ethyl ether gives the title compound, mp 110°–111°.

Example 55

2-[(N-Methyl-N-(3-(1-methylethylamino)-2-pyridinyl)amino]ethylindol-2-carboxylate Palladium black (110 mg) is added to 2-(N-methyl-N-(3-nitro-2-pyridinyl)amino)-ethyl indol-2-carboxylate (PREPARATION 37, 195 mg) in methanol (75 ml). The mixture is stirred under a hydrogen atmosphere (balloon) for 30 min at 20°–25°, filtered and concentrated to give a solid. The solid is dissolved in ethanol (12 ml) and treated with acetone (0.64 ml) and sodium cyanoborohydride (27 mg). Acetic acid is added to adjust to pH 5 as measured on moistened pH test paper. The mixture is stirred for 3.8 days during which time additional sodium cyanoborohydride (39 mg) is added in portions, adjusting the pH on each addition. The mixture is adjusted to pH 3 with aqueous hydrochloric acid (10), neutralized with aqueous sodium hydroxide (5%) and concentrated under reduced pressure to 5 ml. The residue is diluted with chloroform, washed with water, saturated aqueous potassium carbonate, saline and dried over magnesium sulfate. Removal of solvent under reduced pressure gives an oil which is chromatographed on silica gel (10 g, 230–400 mesh) eluting with a gradient of 10–50% ethyl acetate/hexane. The appropriate fractions are pooled and concentrated to give the title compound, mp 130°–131°.

Example 56

1-(Indolyl-2-carbonyl)-4-(3-cyclopentylamino-2-pyridinyl)piperazine (III)

Following the general procedures of PREPARATIONS 6 and 7 and EXAMPLE 11 and making noncritical variations but using cyclopentanone as the carbonyl component of the reductive amination reaction, the title compound is obtained, mp 165.0°–165.5°.

Example 57

1-(Indolyl-2-carbonyl)-4-(3-cyclopropylamino-
2-pyrazinyl)piperazine (III)

Cyclopropylamine (2.4 ml) is added to a solution of 2,3-dichloropyrazine (1.05 g) in dry tetrahydrofuran (5 ml). The mixture is stirred 20 hr at 20°–25°, 24 hr at 50° and 24 hr at 65°. The mixture is diluted with ethyl acetate (50 ml), washed with saturated sodium bicarbonate solution (10 ml), dried with saline and over sodium sulfate and concentrated to an oil, a 10:1 mixture of 2-chloro-3-cyclopropylaminopyrazine and the starting dichloropyrazine. Piperazine (301 mg) is added to the oil (120 mg) and tetrahydrofuran (1 ml). The mixture is heated 65 hr at 80°, diluted with ether (30 ml) and washed with water (10 ml) containing aqueous sodium hydroxide solution (5%, 2 ml). The aqueous phase is separated and extracted with ether (10 ml). The aqueous phase is saturated with sodium chloride and extracted with ether (3×10 ml). The ether extracts are dried over sodium sulfate, concentrated and reconcentrated from chloroform to give 1-(3-chloropyrazin-2-yl)piperazine. A solution of indol-2-carboxylic acid (18 mg) and 1,1'-carbonyldiimidazole (19 mg) in dry tetrahydrofuran (1 ml) is stirred for one hour at 20°–25° and a solution of the above piperazine (25 mg) in tetrahydrofuran (1 ml) is added. After 2 hr, the mixture is diluted with methylene chloride (30 ml), washed with water and dried with saline and sodium sulfate. Removal of solvent gives a solid which is chromatographed on a 20 ml bed of silica gel packed with methylene chloride and eluted with 50 ml of 1%, 100 ml of 2% and 100 ml of 3% methanol/methylene chloride, the appropriate fractions are pooled and concentrated to give the title compound, which solidifies on trituration with ether, mp 164°–167°, decomp.

Example 58

2-(2-(N-Methyl-N-(indolyl-2-carbonyl)amino)ethoxy)-
3-(1-methylethylamino)pyridine (III)

Acetone (0.3 ml) and sodium cyanoborohydride (35 mg) are added to a solution of 2-(2-N-methyl-N-(indolyl-2-carbonyl)amino)ethoxy)-3-aminopyridine (PREPARATION 39) in ethanol (10 ml) containing dimethylformamide. Acetic acid is added to adjust the pH to 4 as measured by placing an aliquot on moistened pH indicator paper. Additional sodium cyanoborohydride (20 and 25 mg) and acetic acid are added at intervals. After stirring 3 days at 20°–25° the pH is adjusted to 2, the solution is neutralized with aqueous sodium hydroxide and concentrated under reduced pressure. The residue is taken up with chloroform and extracted with water, saturated potassium carbonate and water. The organic phase is dried with saline and magnesium sulfate and concentrated under reduced pressure. The material is chromatographed on silica gel with 1% methanol/chloroform, pooling appropriate fractions and then purified by preparative layer chromatography on silica gel with ethyl acetate/hexane (1/1) collecting the band with $R_f$=0.25–0.38 to give the title compound, NMR (CDCl$_3$) 10.06, 7.65, 7.44, 7.25, 7.11, 6.87, 6.77, 6.67, 4.67, 4.0, 3.48, 3.26, 1.05 δ.

Example 59

2-(2-(Indolyl-2-carboxy)ethoxy)-3-
(1-methylethylamino)pyridine (III)

Following the general procedure of EXAMPLE 52 and making non-critical variations but starting with 2-(2-(indolyl-2-carboxy)ethoxy)-3-nitropyridine (PREPARATION 49) the title compound is obtained, mp 104°–105.5°

Example 60

1-[5-(Ethoxycarbonylmethoxy)indolyl-2-carbonyl]-
4-[3-(1-methylethylamino)-2-pyridinyl]piperazine
(III)

1-[5-Hydroxyindolyl-2-carbonyl]-4-[3-(1-methylethylamino)-2-pyridinyl]piperazine (EXAMPLE 38, 95 mg) is added in one portion to a suspension of sodium iodide (6.75 mg) and anhydrous potassium carbonate (38 mg) in dry dimethylformamide (4.5 ml dried over molecular sieves). After stirring for 20 min ethyl bromoacetate is added dropwise. The reaction mixture is then allowed to stir for about 72 hr at 20°–25°. The reaction mixture is diluted with ethyl acetate, washed with saturated sodium bicarbonate, and saline, dried over magnesium sulfate, and concentrated to give an oil. The oil is purified on a silica gel flash column eluting with hexane/ethyl acetate (1/1), the appropriate fractions are pooled and concentrated to give an oil. This oil is crystallized from ether/hexane to give the title compound, mp 125.5°–127.5°.

Example 61

1-[5-(Carbomethoxyindolyl)-2-carbonyl]-4-[3-
(1-methylethyl-amino)-2-pyridinyl]piperazine
sodium salt (III)

1-[5-(Ethoxycarbonylmethoxy)indolyl-2-carbonyl]-4-[3-(1-methylethylamino)-2-pyridinyl]piperazine (III, EXAMPLE 60, 102 mg) is hydrolyzed with sodium hydroxide (2N, 0.11 ml) in ethanol (1 ml). After stirring at 20°–25° for 1 hr, the reaction mixture is diluted with high purity water, frozen, and lyophilized to afford the title compound, mp 273°–276°.

Example 62

1-(Benzimidazolyl-2-carbonyl)-4-[3-
1-methylethylamino)-2-pyridinyl]piperazine (III)

Benzimidazole-2-carboxylic acid (84 mg) and 1,1'-carbonyldiimidazole (84 mg) are dissolved in dry THF (1 ml) and stirred at 20°–25° for 130 min. The resulting solution is added via canula to a −10° cooled solution of 1[3-(ethylamino)-2-pyridinyl]piperazine (International Publication No PCT/US86/01797, PREPARATION A-47, 122 mg) in dry THF (1 ml). The reaction mixture is then allowed to reach 20°–25° overnight. The reaction mixture is then diluted with ethyl acetate, washed with saturated sodium bicarbonate, saline, and water, dried over magnesium sulfate, and concentrated to give an oil. The oil is purified on a silica gel flash column eluting with hexane/ethyl acetate, the appropriate fractions are pooled and concentrated to give a solid. The solid is recrystallized from hexane/methylene chloride the title compound, mp 161°–163°.

Example 63

1-(5-Fluoroindolyl-2-carbonyl)-4-[3-
methylamino-2-pyridinyl]piperazine (III)

5-Fluoroindole-2-carboxylic acid (98 mg) and 1,1'-carbonyldiimidazole (95 mg) are dissolved in dry THF (1 ml) and stirred for 2 hr at 20°–25°. The resulting solution is added via canula to a −10° cooled solution of 4-[3-(methylamino)-2-pyridinyl]piperazine (117 mg) in dry THF (1 ml). The reaction mixture is then allowed to reach 20°–25° overnight. The reaction mixture is then diluted with ethyl acetate, washed with saturated sodium bicarbonate and saline, dried over magnesium sulfate, and concentrated to give a solid, which is purified on a silica gel flash column eluting with hexane/ethyl acetate (1/1). The appropriate fractions are pooled and concentrated to give a solid. Recrystallization of the solid from ethyl acetate/ether gives the title compound, mp 194°–195°.

Example 64

1-(5-Methoxyindolyl-2-carbonyl)-4-[3-(methylamino)-2-pyridinyl]piperazine (IV)

Following the general procedure of EXAMPLE 63 and making non-critical variations but starting with 5-methoxyindole-2-carboxylic acid, the title compound is obtained, mp 199°–201°.

Example 65

1-(Indolyl-2-carbonyl)-4-[3-(methylamino)-2-pyridinyl]piperazine (III)

Following the general procedure of EXAMPLE 63 and making non-critical variations but starting with indole-2-carboxylic acid, the title compound is obtained, mp 153°–154°.

Example 66

1-[Naphthyl-2-carbonyl]-4-[3-(ethylamino)-2-pyridinyl]-piperazine (III)

Following the general procedure of EXAMPLE 62 and making non-critical variations but starting with 2-napthoic acid the title compound is obtained, mp 146°–148°.

Example 67

1-[5-(Benzyloxycarbonylmethoxy)indolyl-2-carbonyl]-4-[3-(1-methylethylamino)-2-pyridinyl]piperazine (III)

1-[5-Hydroxyindolyl-2-carbonyl]-4-[3-(1-methylethylamino)-2-pyridinyl]piperazine (EXAMPLE 38, 198 mg) is added to a heterogeneous solution containing anhydrous potassium carbonate (98 mg), sodium iodide (18 mg) and dimethylformamide (1 ml). After stirring for 15 min benzyl bromoacetate (0.087 ml) is added dropwise. The reaction mixture is allowed to stir for three days and then it is diluted with ethyl acetate, washed with saturated sodium bicarbonate and water, dried over magnesium sulfate, and concentrated to give an oil. The oil is purified through a silica gel flash column eluting with hexane/ethyl acetate (1/1), the appropriate fractions are pooled and concentrated to give a colorless oil. This oil solidifies on standing to give the title compound, mp 134°–137°.

Example 68

1-[5-(Carboxymethoxy)indolyl-2-carbonyl]-4-[3-(1-methylethylamino)-2-pyridinyl]piperazine (III)

Palladium on carbon (10%, 44 mg) is added to a solution of 1-[5-(Benzyloxycarbonylmethoxy)indolyl-2-carbonyl]-4-[3-(1-methylethylamino)-2-pyridinyl]piperazine (EXAMPLE 67, 128 mg) in absolute ethanol (10 ml) and this mixture is subjected to 40 psi of hydrogen gas. After shaking for 2 hr, the reaction mixture is filtered and the solid material washed with absolute ethanol. The filtrate is concentrated and filtered through Celite to give the title compound; NMR (CDCl$_3$/TMS) 1.22, 3.12, 3.52, 3.96, 4.62, 6.62, 6.78–7.05, 7.14, 7.69 and 10.28 δ.

Example 69

1-[Pyrrolyl-2-carbonyl]-4-[3-(1-methylethylamino)-2-pyridinyl]piperazine (III)

Following the general procedure of EXAMPLE 16A and making non-critical variations but starting with pyrrole-2-carboxylic acid (0.30 g), 1-(3-(1-methylethylamino-2-pyridinyl)piperazine (PREPARATION 9, 0.59 g) and 1-(ethyl)-3-(dimethylaminopropyl)carbodiimide (0.62 g), the title compound is obtained; NMR (300 MHz, CDCl$_3$) 7.68, 6.95–6.90, 6.83, 6.56, 6.25, 4.16, 3.98, 3.56, 3.12 and 1.25 δ.

Example 70

1-[Pyrrolyl-2-carbonyl]-4-(3-ethylamino-2-pyridinyl)piperazine (III)

Following the general procedure of EXAMPLE 16 and making non-critical variations but starting with pyrrole-2-carboxylic acid (0.50 g), 1-(3-ethyl-2-pyridinyl)piperazine (0.97 g), CDI (0.77 g) and THF (9 ml), the title compound is obtained, mp 61°–62°; NMR (300 MHz, CDCl$_3$) 9.46, 7.70, 6.96–6.90, 6.84, 6.56, 6.25, 4.20, 3.98, 3.14 and 1.31 δ.

Example 71

1-[6-Methoxy-7-methylindolyl-2-carbonyl]-4-(3-ethylamino-2-pyridinyl)piperazine (III)

Following the general procedure of EXAMPLE 16 and making non-critical variations but starting with 6-methoxy-7-methylindole-2-carboxylic acid (0.23 g), 1-(3-ethyl-2-pyridinyl)piperazine (0.24 g), 1,1'-carbonyldiimidazole (0.19 g) and THF (3 ml), the title compound is obtained, mp 162°–163°.

Example 72

1-[5,6-Dimethoxyindolyl-2-carbonyl]-4-[3-(1-methylethylamino)-2-pyridinyl]piperazine (III)

Following the general procedure of PREPARATION 16A and making non-critical variations but starting with 5,6-dimethoxyindole-2-carboxylic acid (0.42 g), 1-(3-(1-methylethylamino-2-pyridinyl)piperazine (0.42 g) and 1-(ethyl)-3-(dimethylaminopropyl)carbodiimide (0.64 g), the title compound is obtained, mp 242°–243°.

Example 73

1-[3-methylindolyl-2-carbonyl]-4-[3-(1-methylethylamino)-2-pyridinyl]piperazine (III)

Following the general procedure of EXAMPLE 16A and making non-critical variations but starting with 3-methylindole-2-carboxylic acid (PREPARATION 42, 0.58 g), 1-(3-(1-methylethylamino-2-pyridinyl)piperazine (0.73 g) and 1-(ethyl)-3-(dimethylaminopropyl)carbodiimide (0.76 g), the title compound is obtained, mp 191°–192°.

Example 74

1-[Indolyl-2-carbonyl]-4-[2-(1-methylethylamino)-4-fluorophenyl]piperazine (III)

1-[Indolyl-2-carbonyl]-4-[2-amino-4-fluorophenyl]piperazine (PREPARATION 44, 0.74 g) is dissolved in methanol (4.5 ml) and glacial acetic acid (3.13 ml) and acetone (0.24 ml) are added. After 10 min of stirring, sodium cyanoborohydride (0.21 g) is added and the reaction is stirred 24 hr. Then mixture is poured into aqueous sodium hydroxide (10%, 75 ml) and extracted with chloroform (3×100 ml), dried over anhydrous sodium sulfate and filtered through a plug (20 g) of silica gel. The silica is washed with methanol/chloroform (5/95, 100 ml). The organic phases are combined and concentrated under reduced pressure to give the title compound, mp 154°–155°.

Example 75

1-[Indolyl-2-carbonyl]-4-[2-(1-methylethylamino)-5-fluorophenyl]piperazine (III)

Following the general procedure of EXAMPLE 74 and making non-critical variations but starting with 1-[indolyl-2-carbonyl]-4-[2-amino-5-fluorophenyl]piperazine (PREPARATION 46, 0.42 g), the title compound is obtained, mp 193°–194°.

Example 76

1-[Indolyl-2-carbonyl]-4-[3-(1-pyrrolidinyl)-2-pyridinyl]piperazine (III)

Following the general procedure of EXAMPLE 16A and making non-critical variations but starting with indole-2-carboxylic acid (0.12 g), 1-[3-(1-pyrrolidinyl)-2pyridinyl] piperazine (PREPARATION 48, 0.17 g) and 1-(ethyl)-3-(dimethylaminopropyl)carbodiimide (0.17 g), the title compound is obtained, mp 181°–182°.

Example 77

1-[3,5-Dimethyl-4-methoxybenzoyl]-4-[3-(ethylamino)-2-phenyl]-piperazine (IV)

Following the general procedure of EXAMPLE 16A and making non-critical variations but starting with 3,5-dimethyl-4-methoxybenzoic acid (0.075 g), 1-[3-(ethylamino)-2-phenyl]piperazine (0.094 g) and 1-(ethyl)-3-(dimethylaminopropyl)carbodiimide (0.10 g), the title compound is obtained, mp 75°–77°.

Example 78

1-[3,5-Dimethyl-4-methoxybenzoyl]-4-[3-(1-methylethylamino)-2-pyridinyl]piperazine (IV)

Following the general procedure of EXAMPLE 16A and making non-critical variations but starting with 3,5-dimethyl-4-methoxybenzoic acid (0.075 g), 1-[3-(1-methylethylamino)-2-pyridinyl]piperazine (0.101 g) and 1-(ethyl)-3-(dimethylaminopropyl)carbodiimide (0.096 g), the title compound is obtained, mp 89°–93°.

Example 80

1-[5-Methoxyindolyl-2-methyl]-4-3-(ethylamino)-2-pyridinyl]piperazine (IV)

1-[5-Methoxyindolyl-2-carbonyl]-4-[3-(1-methylethylamino-2-pyridinyl]-piperazine (0.20 g) is dissolved in toluene (0.5 ml) and cooled to −10°. Then diisobutylaluminum hydride (1M in toluene, 2.0 ml) is added dropwise via syringe. The reaction is slowly warmed to 20°–25° and stirred for 18 hr. Then 2 more equivalents of diisobutylaluminum hydride are added and the reaction is warmed to 50°. After 3 hr, the reaction is cooled to 20°–25° and quenched by the dropwise addition of 9.3 ml of methanol followed by water (0.75 ml). The mixture is stirred for 30 min and the precipitate is filtered off and the mother liquors are concentrated under reduced pressure. The product is recrystallized from ethyl acetate to provide the title compound, mp 203°–204°.

Example 81

1-[Indolyl-2-carbonyl]-4-(3-ethylamino-2-pyridinyl)-1,4-diazepine (III)

Following the general procedure of EXAMPLE 16 and making non-critical variations but starting with 1-(3-ethylamino-2-pyridinyl)-1,4-diazepine (0.96 g), the title compound is obtained, mp 162°–164°.

Example 82

1-(5-Fluoroindolyl-2-carbonyl)-4-(3-ethylamino-2-pyridinyl)-1,4-diazepine (III)

Following the general procedure of EXAMPLE 16 and making non-critical variations but starting with 1-(3-ethylamino-2-pyridinyl)-1,4-diazepine (0.96 g), the title compound is obtained, mp 168°–169°.

Example 83

1-(Indolyl-2-carbonyl)-4-[3-(1-methylethylamino)-2-pyridinyl]-1,4-diazepine (III)

Following the general procedure of EXAMPLE 16 and making non-critical variations but starting with 1-[1-methylethylamino)-2-pyridinyl]-1,4-diazepine (0.5 g), the title compound is obtained, mp 171°–173°.

Example 84

1-(5-Fluoroindolyl-2-carbonyl)-4-(3-(1-methylethylamino-2-pyridinyl)-1,4-diazepine (III)

Following the general procedure of EXAMPLE y16 and making non-critical variations but starting with 1-(3-(1-methylethylamino-2-pyridinyl)-1,4-diazepine (0.50 g), the title compound is obtained, mp 135°–136°.

Example 85

1-[(5N-(N',N'-Dimethylaminomethylene)aminoindolyl)carbonyl]-4-(3(1-methylethylamino)-2-pyridinyl)piperazine, methane sulfonate (III)

Dimethylformamide dimethyl acetal (0.067 g) and 1-[2-(5-aminoindolyl)-carbonyl]-4-(3-(1-methylethylamino)-2-pyridinyl)piperazine (EXAMPLE 101, 0.14 g) are dissolved in dimethylformamide (0.7 ml). The reaction is stirred at 20°–25° for 3 hr, then diluted with methanol/chloroform (5/95), washed with water (3 x), saline, dried over anhydrous sodium sulfate and concentrated under reduced pressure. Purification by flash column chromatography (30 g silica gel) eluting with methanol/chloroform (5/95), pooling and concentration of the appropriate fractions gives a solid. Recrystallization of the solid from ethyl acetate/hexane gives the title compound, mp 139°–142°.

The free base is dissolved in methanol and 1 eq. of methanesulfonic acid is added. Ether is added until cloudy and the vessel set aside until crystallization is complete. Filtration provided the mesyl salt of the title compound, mp 203°–206°.

Example 86

1-[5-(2'-Aminoacetamido)indolyl-2-carbonyl]-4-(3-(1-methylethylamino)-2-pyridinyl)piperazine hydrochloride (III)

1-[5-(2'-benzyloxyglycylamino)indolyl-2-carbonyl]-4-(3-(1-methylethylamino)-2-pyridinyl)piperazine (PREPARATION 60, 2.58 g) is dissolved in ethanol/THF (2/1, 150 ml) and palladium on carbon (10%, 0.3 g) is added. The reaction is hydrogenated at 40 psi for 10 hr, then filtered through a pad of celite and concentrated under reduced pressure to give the free base of the title compound.

The amine is dissolved in methanol and cooled to 20°–25°, then 1 eq. of trimethylsilyl chloride is added and ether is added until cloudy. The solids formed are recrystallized from methanol/ether to give the title compound, mp 189°–191°.

Example 87

1-[6-Methoxyindolyl-2-carbonyl]-4-[3-(1-methylethylamino)-2-pyridinyl]-piperazine (III)

Following the general procedure of EXAMPLE 16 and making non-critical variations but starting with 6-methoxyindole-2-carboxylic acid (PREPARATION 63, 0.35 g), 1-[3-(1-methylethylamino)-2-pyridinyl]piperazine (0.40 g), 1,1'-carbonyldiimidazole (0.31 g) and THF (6.6 ml), the title compound is obtained, mp 191°–193°.

Example 88

1-[4-Methoxyindolyl-2-carbonyl]-4-[3-(1-methylethylamino)-2-pyridinyl]piperazine (III)

Following the general procedure of EXAMPLE 16 and making non-critical variations but starting with 4-methoxyindole-2-carboxylic acid (PREPARATION 69, 0.35 g), 1-[3-(1-methylethylamino)-2-pyridinyl]piperazine (0.44 g), 1,1'-carbonyldiimidazole (0.30 g) and THF (3.6 ml), the title compound is obtained, mp 196°–197°.

Example 89

1-[5-Methylindolyl-2-carbonyl]-4-[3-(1-methylethylamino)-2-pyridinyl]piperazine (III)

Following the general procedure of EXAMPLE 16 and making non-critical variations but starting with 5-methylindole-2-carboxylic acid (0.23 g), 1-[3-(1-methylethylamino)-2-pyridinyl]piperazine (0.29 g) and 1,1'-carbonyldiimidazole (0.21 g) the title compound is obtained, mp 199°–201°.

Example 90

1-[5,6-Methylenedioxyindolyl-2-carbonyl]-4-[3-(1-methylethylamino)-2-pyridinyl]piperazine (III)

Following the general procedure of EXAMPLE 16A and making non-critical variations but starting with 5,6-methylenedioxyindole-2-carboxylic acid (PREPARATION 79, 0.30 g), 1-[3-(1-methylethylamino)-2-pyridinyl]piperazine (0.32 g) and 1-(ethyl)-3-(dimethylaminopropyl)carbodiimide (0.34 g), the title compound is obtained, mp 220°–221°.

Example 91

1-[5-Fluoro-6-methoxyindolyl-2-carbonyl]-4-[3-(1-methylethylamino)-2-pyridinyl]piperazine (III)

Following the general procedure of EXAMPLE 16A and making non-critical variations but starting with 5-fluoro-6-methoxyindole-2-carboxylic acid (PREPARATION 92, 0.30 g), 1-[3-(1-methylethylamino)-2-pyridinyl]piperazine (0.32 g) and 1-(ethyl)-3-(dimethylaminopropyl)carbodiimide (0.33 g), the title compound is obtained, mp 193°–194°.

Example 92

1-[7-Bromo-6-methoxyindolyl-2-carbonyl]-4-[3-(1-methylethyl-amino)-2-pyridinyl]piperazine (III)

Following the general procedure of EXAMPLE 16A and making non-critical variations but starting with 7-bromo-6-methoxyindole-2-carboxylic acid (PREPARATION 83, 0.30 g), 1-[3-(1-methylethylamino)-2-pyridinyl]piperazine (0.25 g) and 1-(ethyl)-3-(dimethylaminopropyl)carbodiimide (0.326 g), the title compound is obtained, mp 179°–180°.

Example 93

1-[5-Bromoindolyl-2-carbonyl]-4-[3-(1-methylethylamino)-2-pyridinyl]piperazine (III)

Following the general procedure of EXAMPLE 16A and making non-critical variations but starting with 5-bromoindole-2-carboxylic acid (0.51 g), 1-[3-(1-methylethylamino)-2-pyridinyl]piperazine (0.47 g) and 1-(ethyl)-3-(dimethylaminopropyl)carbodiimide (0.49 g), the title compound is obtained, mp 229°–230°.

Example 94

1-[5-Bromo-6-methoxyindolyl-2-carbonyl]-4-[3-(1-methylethylamino)-2-pyridinyl]piperazine (III)

Following the general procedure of EXAMPLE 16A and making non-critical variations but starting with 5-bromo-6-methoxyindole-2-carboxylic acid (PREPARATION 82, 0.40 g), 1-[3-(1-methylethylamino)-2-pyridinyl]piperazine (0.33 g) and 1-(ethyl)-3-(dimethylaminopropyl)carbodiimide (0.34 g), the title compound is obtained, mp 202°–204°.

Example 95

1-[6-(N,N-Dimethylamino)indolyl-
2-carbonyl]-4-[3-(1-methylethylamino)-
2-pyridinyl]piperazine (III)

Following the general procedure of EXAMPLE 16A and making non-critical variations but starting with 6-(N,N-dimethylamino)indole-2-carboxylic acid (PREPARATION 89, 0.40 g), 1-[3-(1-methylethylamino)-2-pyridinyl]piperazine (0.43 g) and 1-(ethyl)-3-(dimethylaminopropyl)carbodiimide (0.45 g), the title compound is obtained, mp 153°–154°.

Example 97

1-[4-Methylindolyl-2-carbonyl]-
4-[3-(1-methylethylamino)-2pyridinyl]-piperazine
(III)

Following the general procedure of EXAMPLE 16A and making non-critical variations but starting with 4-methylindole-2-carboxylic acid (PREPARATION 86, 0.40 g), 1-[3-(1-methylethylamino)-2-pyridinyl]piperazine (0.50 g) and 1-(ethyl)-3-(dimethylaminopropyl)carbodiimide (0.52 g), the title compound is obtained, mp 165°–167°.

Example 99

1-[Indolyl-2-carbonyl]-4-[3-(1-methylpropyl)
amino)-2-pyridinyl]-piperazine (III)

Following the general procedure of EXAMPLE 16A and making non-critical variations but starting with indole-2-carboxylic acid (0.21 g), 1-[3-(1-methylpropyl)amino)-2-pyridinyl]piperazine (0.30 g), 1-(ethyl)-3-(dimethylaminopropyl)carbodiimide (0.29 g) and THF (3 ml), the title compound is obtained, mp 165°–166°.

Example 100

1-[Indolyl-2-carbonyl]-4-[3-(1-ethylpropyl)
amino)-2-pyridinyl]piperazine (III)

Following the general procedure of EXAMPLE 16A and making non-critical variations but starting with indole-2-carboxylic acid (0.095 g), 1-[3-(1-ethylpropyl)amino)-2-pyridinyl]piperazine (PREPARATION 73, 0.15 g), 1-(ethyl)-3-(dimethylaminopropyl)carbodiimide (0.14 g) and THF (1.2 ml), the title compound is obtained, mp 190°–192°.

Example 101

1-[5-Aminoindolyl-2-carbonyl]-4-[3-
(1-methylethylamino)-2-pyridinyl]-piperazine (III)

1-[5-Nitroindolyl-2-carbonyl]-4-[3-(1-methylethylamino)-2-pyridinyl]piperazine (EXAMPLE 103, 1.0 g) is dissolved in ethanol (60 ml) and THF (60 ml) and palladium on carbon (10%, 0.15 g) is added. The reaction is hydrogenated at 40 psi for 14 hr, then filtered through celite and concentrated under reduced pressure. Purification by flash chromatography, eluting with ethyl acetate/hexane (50/50→ 75/25), pooling and concentrating the appropriate fractions gives the title compound, mp 212°–214°.

Example 102

1-[5-Fluoroindolyl-2-carbonyl]-4-[3-(2',2'-
dimethylpropylamino)-2-pyridinyl]piperazine (III)

Following the general procedure of PREPARATION 8 and making non-critical variations but starting with 1-[5-fluoroindolyl-2-carbonyl]-4-[-4-[-3-amino-2-pyridinyl]piperazine (PREPARATION 78, 0.15 g), sodium cyanoborohydride (29.4 mg), trimethylacetaldehyde (38.1 mg), acetic acid and methanol (0.9 ml), the title compound is obtained, mp 205°–206°.

Example 103

1-[5-Nitroindolyl-2-carbonyl]-4-
[3-(1-methylethylamino)-2-pyridinyl]piperazine (III)

Following the general procedure of EXAMPLE 16A and making non-critical variations but starting with 5-nitroindole-2-carboxylic acid (0.86 g), 1-[3-(N-isopropyl)amino-2-pyridinyl]piperazine (0.43 g), 1-(ethyl)-3-(dimethylaminopropyl)carbodiimide (0.45 g) and THF (4 ml), the title compound is obtained, mp 153°–154°.

Example 104

1-[5-Acetamidoindolyl-2-carbonyl]-4-[3-
(1-methylethylamino)-2-pyridinyl]piperazine (III)

1-[5-Aminoindolyl-2-carbonyl]-4-[3-(1-methylethylamino)-2-pyridinyl]piperazine (EXAMPLE 101, 0.075 g) is dissolved in methylene chloride (0.4 ml) and pyridine (0.016 g) is added and then the reaction is cooled to 0°. Acetyl chloride (0.016 g) is added and stirred for 2.5 hr. The reaction mixture is diluted with chloroform and washed with saturated aqueous sodium bicarbonate, saline, dried over anhydrous sodium sulfate and concentrated under reduced pressure. Purification by flash column chromatography, eluting with ethyl acetate, pooling and concentrating the appropriate fractions gives the title compound, mp 136°–138°.

Example 105

1-[5-Methanesulfonamidoindolyl-2-carbonyl]-
4-[3-(1-methylethylamino)-2-pyridinyl]piperazine
(III)

1-[(5-Aminoindolyl-2-carbonyl]-4-[3-(1-methylethylamino)-2-pyridinyl]piperazine (EXAMPLE 101, 0.075 mg) is dissolved in methylene chloride (0.4 ml) and pyridine (0.016 g) is added and the reaction is cooled to 0°. Then methanesulfonyl chloride (0.023 g) is added. After 2.5 hr of stirring, the reaction is diluted with chloroform and washed with saturated aqueous sodium bicarbonate, saline, dried over anhydrous sodium sulfate and concentrated under reduced pressure. The concentrate is dissolved in the minimum amount of chloroform and passed through a small plug of silica gel and then it is recrystallized with ethyl acetate/hexane to provide the title compound, mp 226°–228°.

Example 106

1-[5-Fluoroindolyl-2-carbonyl]-4-[3-(2-methoxy-
1-methylethylamino)-2-pyridinyl]piperazine (III)

Following the general procedure of PREPARATION 8 and making non-critical variations but starting with 1-[5-fluoroindolyl-2carbonyl]-4-[3-amino-2-pyridinyl]piperazine (PREPARATION 129, 0.15 g,) methoxyacetone (0.04 g), sodium cyanoborohydride (0.029 g), acetic acid (0.53 g) and methanol (0.8 ml), the title compound is obtained, mp 163°–164°.

Example 107

N,N'-Dimethyl-N-(5-methoxyindolyl-2-carbonyl)-N'-[3-(1-methylethylamino)-2-pyridyl]ethylenediamine (IV)

Following the general procedure of EXAMPLE 52 making non-critical variations and employing N,N'-dimethyl-N-(5-methoxyindolyl-2-carbonyl)-N'-(3-nitro-2-pyridinyl) ethylenediamine (PREPARATION 74) the title compound is obtained, mp 116.5°–117°.

Example 108

N,N'-Dimethyl-N-(5-fluoroindolyl-2-carbonyl)-N'-(3-(1-methylethylamino)-2-pyridyl) ethylenediamine (III)

Following the general procedure of EXAMPLE 52 making non-critical variations and employing N,N'-dimethyl-N-(5-fluoroindolyl-2-carbonyl)-N'-(3-nitro-2-pyridinyl)ethylenediamine (PREPARATION 75) the title compound is obtained, mp 121°–122.5°.

Example 109

1-(7-Azaindolyl-2-carbonyl)-4-methylethylamino)-2-pyridinyl)piperazine (III)

Following the general procedure of EXAMPLE 1 and making non-critical variations but starting with 7-azaindole-2-carboxylic acid (PREPARATION 76) and 1-(3-(1-methylethylamino-2-pyridinyl)piperazine (II, PREPARATION 9) the title compound is obtained, mp 174°–175°.

Example 110

1-(5-Azaindolyl-2-carbonyl)-4-(3-(1-methylethylamino)-2-pyridinyl)piperazine (III)

Following the general procedure of EXAMPLE 1 and making non-critical variations but starting with 5-azaindole-2-carboxylic acid (PREPARATION 77) and 1-(3-(1-methylethylamino-2-pyridinyl)piperazine (II, PREPARATION 9) the title compound is obtained.

Example 111

N,N'-Dimethyl-N-(indolyl-2-carbonyl)-N'-(3-(ethylamino-2-pyridinyl)-1,3-propanediamine (III)

Following the general procedure of PREPARATIONS 34 and 35 and EXAMPLE 52 making noncritical variations but starting with N,N'-dimethyl-1,3-propanediamine and employing acetaldehyde in the final reductive alkylation step the title compound is obtained, mp 128.2°–130.2°.

Example 112

N,N'-Dimethyl-N-(indolyl-2-carbonyl)-N'-(3-(ethylamino-2-pyridyl)-1,6-hexanediamine (III)

Following the general procedure of PREPARATIONS 34 and 35 and EXAMPLE 52 making noncritical variations but starting with N,N'-dimethyl-1,6-hexanediamine and employing acetaldehyde in the final reductive alkylation step the title compound is obtained, mp 146° decomp.

Example 113

1-[6-Formylindoyl-2-carbonyl[-4-[3-methylethylamino)-2-pyridinyl]piperazine (III)

Following the general procedure of EXAMPLE 16A and making non-critical variations but starting with 6-formylindole-2-carboxylic acid (PREPARATION 98), and 1-(3-(1-methylethylamino)-2-pyridinyl)piperazine (PREPARATION 9), the title compound is obtained.

Example 114

1-[6-Nitroindoyl-2-carbonyl]-4-[3-(1-methylethylamino)-2-pyridinyl]piperazine (III)

Following the general procedure of EXAMPLE 16A and making non-critical variations but starting with 6-nitroindole-2-carboxylic acid (PREPARATION 95), the title compound is obtained.

Example 115

1-[5-Azido-2-indolycarbonyl]-4-[3-(1-methylethylamino)-2-pyridinyl]piperazine (III)

1-[5-amino-2-indolylcarbonyl[-4-[3-(methylethylamino)-2-pyridinyl]piperazine (0.34 g) is dissolved in 30 ml of 80% acetic acid/water and cooled to −10°. Then sodium nitrite (0.0656 g) dissolved in 1.25 ml of water is precooled to 0° and then added dropwise to the aminoindole. After 30 min, sodium azide (0.062 g) dissolved in 1.25 ml of water is precooled to 0° and added dropwise. the reaction is stirred at 2 hr at −10°. Then 30 ml of water is added and the product is extracted with ether (3×30 ml), saturated sodium carbonate (0°), water, saline, and then dried over anhydrous sodium sulfate. Purification by flash column chromatography (100 g silica gel, 25% ethyl actetate/chloroform) afforded 0.16 g of the product which is further purified by crystallization from ethyl acetate/tetrahydrofuran/hexane to provide the title compound, NMR (300 MHz, $CD_3OD$) 7.39, 7.28, 7.16, 6.85–6.70, 6.66, 3.86, 3.48, 2.93, and 1.08 δ.

Example 116

1-[4-Methoxy-3,4-dimethylbenzyl]-4-(3-(2-propenylamino)-2-pyridinyl]piperazine, hydrochloride (IV)

A mixture of 3,5-dimethyl-4-methoxybenzyl chloride (0.13 g)1-[3-(2-propenylamino)-2-pyridinyl]piperazine (PREPARATION 118, 0.14 g), anhydrous potassium carbonate (0.18 g) and acetonitrile (6 ml) is refluxed under nitrogen for 18 hr. The mixture is cooled and then diluted with dichloromethane and aqueous saturated potassium carbonate solution. The phases are separated. The organic phase is dried over anhydrous sodium sulfate and concentrated to an oil. The oil is flash chromatographed (1% methanol/

Example 117

1-[Indolyl-2-carbonyl]-4-[3(2-fluoroethylamino)-2-pyridinyl]piperazine (III)

Following the general procedure of EXAMPLE 16A and making non-critical variations but starting with 1-[3-(2'-fluoroethylamino)-2-pyridinyl]piperazine (PREPARATION 106, 0.49 g), EDC (0.49 g), indole-2-carboxylic acid (0.32 g), the title compound is obtained, 180°–181°.

Example 118

1-[Indolyl-2-carbonyl]-4-[3-(1-methylethyl)amino-2-pyrazinyl]-1,4-diazepine (III)

Following the general procedure of EXAMPLE 16A and making non-critical variations but starting with indole-2-carboxylic acid (0.19 g) and 1-[3-(1-methylethylamino)-2-pyrazinyl]-1,4-diazepine (PREPARATION 107), the title compound is obtained, m.p. 106°–107°.

Example 119

1-[5-Benzyloxyindolyl-2-carbonyl]-4-[4-(1,1-dimethylethylamino)-2-pyridazinyl]piperazine (III) (III)

Following the general procedure of EXAMPLE 16A and making non-critical variations but starting with 5-benzyloxyindole-2-carboxylic acid, and 1-[4-(1,1-dimethylethylamino)-2-pyridazinyl]piperazine (PREPARATION 110), the title compound is obtained, dec. 132°–133°.

Example 120

1-[5-Hydroxyindolyl-2-carbonyl]-4-[4-(1,1-dimethylethylamino)-2-pyridazinyl]piperazine (III)

1-[5-Benzyloxyindolyl-2-carbonyl]-4-[4(1,1-dimethylethylamino)-2-pyridazinyl]piperazine (EXAMPLE 119) is dissolved in 20 ml of methanol and 6 mg of 10% palladium on carbon is added followed by 0.25 g of ammonium formate. After stirring 2 hr at 20°–25° the reaction is briefly heated with a heat gun to 40°–45° and then allowed to stir at 20°–25° a futher 1 hr. Then it is filtered through celite, the filter pad is washed with methanol, tetrahydrofuran and the organics are combined and concentrated in vacuo to afford 1.33 g. The product is dissolved in 10% methanol/chloroform and washed with water, saline, dried over anhdrous sodium sulfate and concentrated in vacuo to afford the title compound, dec. 274°.

Example 121

1-[Benz[g]indolyl-2-carbonyl]-4-[3-(1-methylethylamino)-2-pyridinyl]piperazine (III)

Following the general procedure of EXAMPLE 16A and making non-critical variations but starting with benz[g]indole-2-carboxylic acid (PREPARATION 112, 0.3 g) and 1-[3-(1-methylethylamino)-2-pyridinyl]piperazine (PREPARATION 9, 0.34 g), the title compound is obtained, m.p. 190°.

Example 122

1-[Benz[e]indolyl-2-carbonyl]-4-[3-(1-methylethylamino)-2-pyridinyl]piperazine (III)

Following the general procedure of EXAMPLE 16A and making non-critical variations but starting with benz[e]indole-2-carboxylic acid (PREPARATION 116, 0.5 g) and 1-[3-(1-methylethylamino)-2-pyridinyl]piperazine (PREPARATION 8, 0.52 g), the title compound is obtained, m.p. 228°–231°.

Example 123

N,N'-Dimethyl-N-(indolyl-2-carbonyl)-N'-(3-ethylamino-2-pyridyl)ethylenediamine (III)

Following the general procedure of PREPARATIONS 34 and 35 and EXAMPLE 52 making non-critical variations but employing acetaldehyde in the final reductive alkylation step the title compound is obtained, mp 140.0°–140.5°.

Example 124

N,N'-Dimethyl-N-(indolyl-2-carbonyl)-N'-[3-(1-methylethyl-amino)-2-pyridyl]-1,4-butanediamine (III)

Following the general procedure of PREPARATIONS 34 and 35 and EXAMPLE 52 and making non-critical variations but employing N,N'-dimethyl-1,4-butanediamine, the title compound is obtained, mp 115.8°–116.5°.

Example 125

1-[6-Hydroxymethylindolyl-2-carbonyl]-4-[3-(1-methylethyl-amino)-2-pyridinyl]piperazine (III)

Following the general procedure of EXAMPLE 16A and making non-critical variations but starting with 6-hydroxymethylindole-2-carboxylic acid (PREPARATION 121), and 1-[3-(1-methylethylamino)-2-pyridinyl]piperazine (PREPARATION 9), the title compound is obtained.

Example 126

1-[6-Hydroxymethylindolyl-2-carbonyl]-4-[3-(ethylamino)-2-pyridinyl]piperazine (III)

Following the general procedure of EXAMPLE 16A and making non-critical variations but starting with 6-hydroxymethylindole-2-carboxylic acid (PREPARATION 121), the title compound is obtained.

Example 127

1-[6-(N,N-Dimethylamino)methylindolyl-2-carbonyl]-4-[3-(1-methylethylamino)-2-pyridinyl]piperazine (III)

1-[6-Methanesulfonylmethylindolyl-2-carbonyl]-4-[3-(1-methylethylamino)-2-pyridinyl]piperazine (PREPARATION 122) is dissolved in acetonitrile and anhydrous potassium carbonate and dimethylamine were added. The reaction is heated to reflux and additional dimethylamine is added as necessary. After completion of the reaction, it is poured into anhydrous sodium bicarbonate and extracted with chloroform. The organic layers are dried over anhy drous sodium sulfate and concentrated in vacuo to provide the title compound.

Example 128

1-[Indolyl-7-carbonyl]-4-[3-(1-methylethylamino)-2-pyridinyl]-piperazine (III)

Following the general procedure of EXAMPLE 16 and making non-critical variations but starting with indole-7-carboxylic acid, the title compound is formed (mp 154°–155°).

Example 129

1-[2,3-Didehydroindolyl-7-carbonyl]-4-[3-(1-methylethylamino)-2-pyridinyl]piperazine (III)

4-[3-(1-methylethylamino)-2-pyridinyl]piperazine (PREPARATION 9) is dissolved in dimethylformamide and 5,6-dihydro-pyrrolo-[3,2,1,i,j,]-[3,1]benzoxazine-1,3-dione (J. Heterocyclic Chemistry 23, 971 (1986) is added. The reaction is allowed to stir 6 hr. Then it is diluted with water and the solids are collected by filtration and recrystallized from acetonitrile to provide the title compound, mp 171°–172°.

Example 130

1-[2,3-Didehydroindolyl-7-carbonyl]-4-[3-(ethylamino)-2-pyridinyl]piperazine (III)

4-[3-(Ethylamino)-2-pyridinyl]piperazine is dissolved in dimethylformamide and 5,6-dihydro-pyrrolo-[3,2,1,i,j]-[3,1]benzoxazine-1,3-dione (*J. Heterocyclic Chemistry*, 23,971 (1986) is added. The reaction is allowed to stir 2.5 hr. Then it is diluted with water and the solids are collected by filtration and recrystallized from acetonitrile to provide the title compound, mp 148°–149°.

Example 131

1-(Indolyl-2-carbonyl)-4-(N-methyl-N-(3-(1-methylethylamino)-2-pyridinyl)amino)piperidine (III)

Following the general procedure of EXAMPLE 52 and making non-critical variations but starting with 1-(indolyl-2-carbonyl)-4-(N-methyl-N-(3-nitro-2-pyridinyl)amino)piperidine (PREPARATION 127) the title compound is obtained, NMR (CDCl$_3$) 9.92, 7.72, 7.62, 7.43, 7.25, 7.11, 6.84, 6.77, 4.68, 4.50, 3.56, 3.48, 3.14, 2.65, 1.94, 1.67 and 1.22 δ.

Example 132

1-[6-Fluoroindolyl-2-carbonyl]-4-[3-(1-methylethylamino)-2-pyridinylpiperazine (III)

Following the general procedure of EXAMPLE 16 and making non-critical variations but using 6-fluoroindole-2-carboxylic acid (PREPARATION 66, 0.32 g) and 1-[3-(1-methylethylamino)-2-pyridinyl]piperazine (0.40 g), the title compound is obtained, mp 177°–178°.

Example 133

1-[5,6-Dimethoxyindolyl-2-carbonyl]-4-[3-ethylamino)-2-pyridinyl]piperazine (III)

Following the general procedure of EXAMPLE 16 and making non-critical variations but using 5,6-dimethoxyindole-2-carboxylic acid (0.50 g) and 1-[3-ethylamino)-2-pyridinyl]piperazine (0.51 g), the title compound is obtained, HMRS=409.2113 (theory for $C_{22}H_{27}N_5O_3$ is 409.2114.

Examples 134–152 See CHART F

Following the general procedure of EXAMPLE 16 or 16A and making non-critical variations but using the [aryl/heteroaryl]-carboxylic acid of Column A and the pyridyl linker of Column B, the corresponding compounds of Column C are obtained.

Example 153

1-[-5-(N',N'-Dimethylaminomethylene)aminoindolyl-2-carbonyl]-4-[3-(1,1-dimethylethylamino)-2-pyridinyl]piperazine (III)

Following the general procedure of EXAMPLES 101 and 85 and making non-critical variations but using 1-[5-nitroindolyl-2-carbonyl]-4-[3-(1,1-dimethylethylamino)-2-pyridinyl]piperazine (EXAMPLE 151, the title compound is obtained.

Example 154

1-[(6-Dimethylaminomethyl)indolyl-2-carbonyl]-4-[3-(1,1-dimethylethylamino)-2-pyridinyl]piperazine (III)

Following the general procedure of EXAMPLE 127 and PREPARATION 122 and making non-critical variations but starting with 1-[6-hydroxymethylindolyl]-2-carbonyl]-4-[3-(1,1-dimethylethylamino)-2-pyridinyl]piperazine, the title compound is obtained.

CHART A

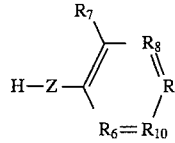

(I)

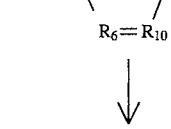

(II)

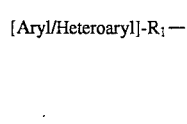

(III)

CHART B
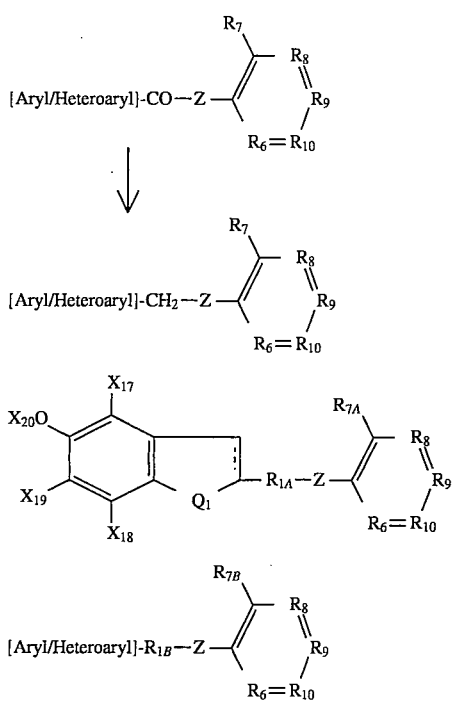
CHART C
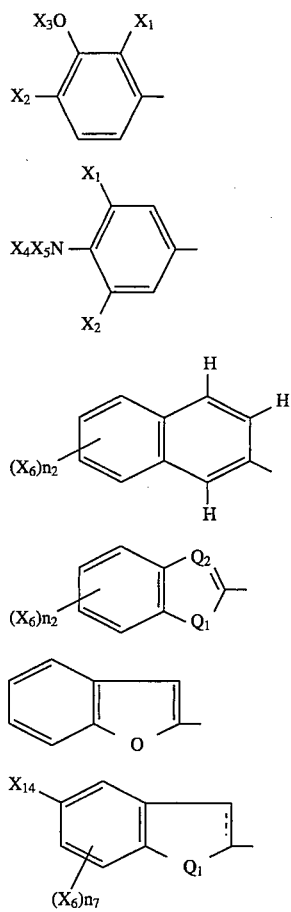
-continued
CHART C
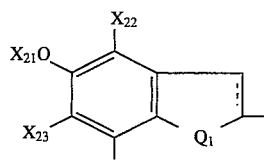           (8)
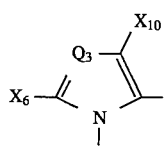           (9)
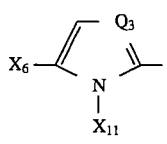           (10)
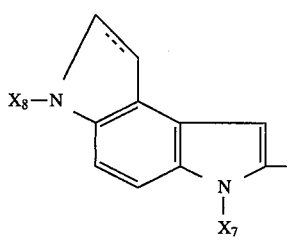           (11)
CHART D
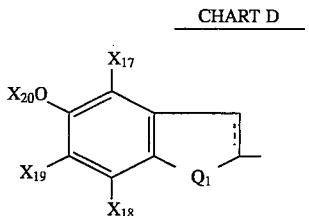           (14)
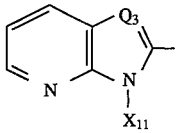           (15)
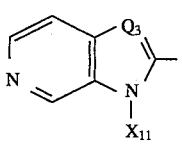          (16)
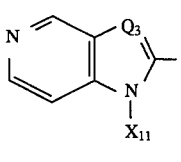          (17)
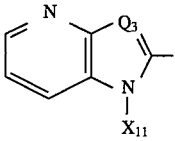          (18)

CHART D -continued

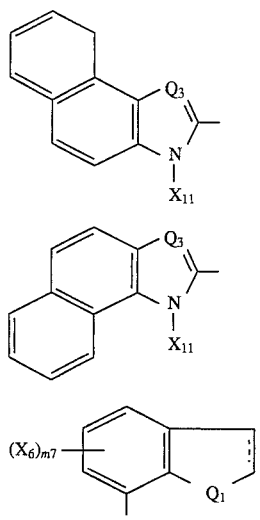

(19)

(20)

(21)

CHART E

 (Z-I)

CHART E -continued

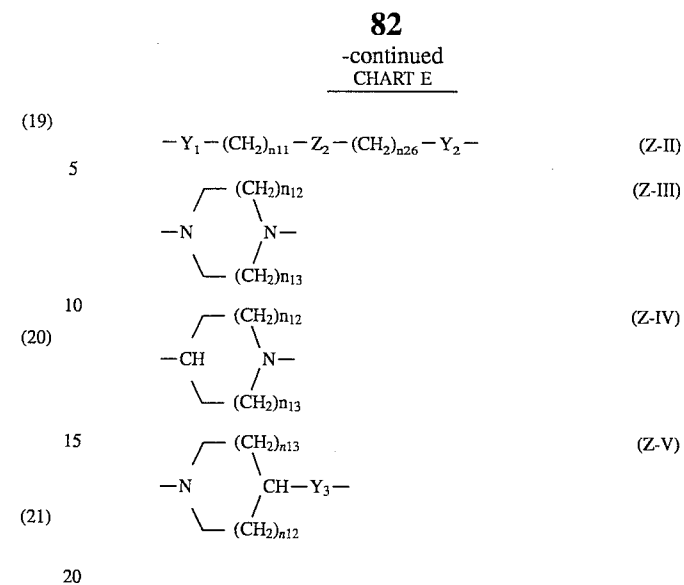

$-Y_1-(CH_2)_{n11}-Z_2-(CH_2)_{n26}-Y_2-$  (Z-II)

(Z-III)

(Z-IV)

(Z-V)

| CHART F | | | |
|---|---|---|---|
| Example | Column A | Column B | Column C |
| 134 | Indole-2-carboxylic acid | N,N'-dimethyl-N-[3-(1-methylethylamino)-2-pyridinyl]-2E-butylenediamine | N,N'-Dimethyl-N-(indolyl-2-carbonyl)-N'-[3-(1-methylethylamino)-2-pyridinyl]-2E-butylenediamine |
| 135 | 5-Methoxyindole-2-carboxylic acid | N,N'-dimethyl-N-[3-(1-methylethylamino)-2-pyridinyl]-2E-butylenediamine | N,N'-Dimethyl-N-(5-methoxyindolyl-2-carbonyl)-N'-[3-(1-methylethylamino)-2-pyridinyl]-2E-butylenediamine |
| 136 | 5-Methoxyindole-2-carboxylic acid | N,N'-dimethyl-N-[3-(1-methylethylamino)-2-pyridinyl]-2Z-butylenediamine | N,N'-dimethyl-N-(5-methoxyindolyl-2-carbonyl)-N'-[3-(1-methylethylamino)-2-pyridinyl]-2Z-butylenediamine |
| 137 | Indole-2-carboxylic acid | N,N'-dimethyl-N-[3-(1-methylethylamino)-2-pyridinyl]-2Z-butylenediamine | N,N'-dimethyl-N-(indolyl-2-carbonyl)-N'-[3-(1-methylethylamino)-2-pyridinyl]-2Z-butylenediamine |
| 138 | Indole-2-carboxylic acid | 2,2,N,N'-tetramethyl-N-[3-(1-methylethylamino)-2-pyridinyl]-1,3-propanediamine | 2,2,N,N'-tetramethyl-N-(indolyl-2-carbonyl)-N'-[3-(1-methylethylamino)-2-pyridinyl]-1,3-propanediamine |
| 139 | Indole-2-carboxylic acid | N,N'-dimethyl-N-[3-(1-methylethylamino)-2-pyridinyl]-3-oxa-1,5-pentanediamine | N,N'-dimethyl-N-(indolyl-2-carbonyl)-N'-[(3-(1-methylethylamino)-2-pyridinyl]-3-oxa-1,5-pentanediamine |
| 140 | Indole-2-carboxylic acid | N,N',N''-trimethyl-N-[3-(1-methylethylamino)-2-pyridinyl]diethylenetriamine | N,N',N''-trimethyl-N-(indolyl-2-carbonyl)-N''-[(3-(1-methylethylamino)-2-pyridinyl]diethylenetriamine |
| 141 | 6-Cyanoindole-2-carboxylic acid | 1-[3-(1-ethylamino)-2-pyridinyl]piperazine | 1-(6-cyanoindolyl-2-carbonyl)-4-[3-(ethylamino)-2-pyridinyl]piperazine |
| 142 | 6-Cyanoindole-2-carboxylic acid | 1-[3-(1-methylethylamino)-2-pyridinyl]piperazine | 1-(6-cyanoindolyl-2-carbonyl)-4-[3-(1-methylethylamino)-2-pyridinyl]piperazine |
| 143 | 6-(1-Pyrrolidinyl)indole-2-carboxylic acid | 1-[3-(methylethylamino)-2-pyridinyl]piperazine | 1-(6-(1-pyrrolidinyl)indolyl-2-carbonyl)-4-[3-(1- |

CHART F

| Example | Column A | Column B | Column C |
|---|---|---|---|
| | | | methylethylamino)-2-pyridinyl]piperazine |
| 144 | 6-(1-Pyrrolidinyl)indole-2-carboxylic acid | 1-[3-(ethylamino)-2-pyridinyl]piperazine | 1-(6-(1-pyrrolidinyl)indolyl-2-carbonyl)-4-[3-(ethylamino)-2-pyridinyl]piperazine |
| 145 | 5-methoxyindole-2-carboxylic acid | 1-[(3-methylamino)-2-pyridinyl]piperazine | 1-(5-methoxyindolyl-2-carbonyl)-4-[3-methylamino-2-pyridinyl]piperazine |
| 146 | 5-methoxyindole-2-carboxylic acid | 1-[(3-propylamino)-2-pyridinyl]piperazine | 1-(5-methoxyindolyl-2-carbonyl)-4-[3-propylamino-2-pyridinyl]piperzine |
| 147 | 5-methoxyindole-2-carboxylic acid | 1-[(3-cyclopropylmethyl amino)-2-pyridinyl]piperazine | 1-(5-methoxyindolyl-2-carbonyl)-4-[3-(cyclopropylmethylamino)-2-pyridinyl]piperazine |
| 148 | 5-methoxyindole-2-carboxylic acid | 1-[3-(1,1-dimethylethyl amino)-2-pyrazinyl]piperazine | 1-(5-methoxyindolyl-2-carbonyl)-4-[3-(1,1-dimethylethylamino)-2-pyrazinyl]piperazine |
| 149 | 6-dimethylaminoindole-2-carboxylic acid | 1-[3-(1,1-dimethylethyl amino)-2-pyrazinyl]piperazine | 1-(6-dimethylaminoindolyl-2-carbonyl)-4-[3-(1,1-dimethylethylamino)-2-pyrazinyl]piperazine |
| 150 | 6-dimethylaminoindole-2-carboxylic acid | 1-[3-(1,1-dimethylethylamino)-2-pyridinyl]piperazine | 1-[(6-dimethylaminoindolyl)-2-carbonyl]-4-[3-(1,1-dimethylethylamino)-2-pyridinyl]piperazine |
| 151 | 5-nitroindole-2-carboxylic acid | 1-[3-(1,1-dimethylethylamino)-2-pyridinyl]piperazine | 1-[5-nitroindolyl-2-carbonyl]-4-[3-(1,1-dimethylethyl amino)-2-pyridinyl]piperazine |
| 152 | 6-hydroxymethylindole-2-carboxylic acid | 1-[3-(1,1-dimethylethylamino)-2-pyridinyl]piperazine | 1-[(6-hydroxymethylindolyl)-2-carbonyl]-4-[3-(1,1-dimethylethylamino)-2-pyridinyl]piperazine |

TABLE 1

CHART G

The utility of this invention is demonstrated by the ability of the compounds used to inhibit viral reverse transcriptase, an enzyme essential for human immunodeficiency virus replication. This enzyme has characteristics which differentiate it from other known cellular polymerases and it is a unique enzyme which is not found in uninfected cells.

| EXAMPLE | RT %[1] INHIBITION (100 μM) | INHIBITION[2] OF SYNCYTIA FORMATION $ED_{50}$ (μM) | PBL[3] INHIBITION OF VIRAL REPLICATION (p24 & RNA) $ED_{50}$ (μM) |
|---|---|---|---|
| 1 | 60–79 | 10 | 1 |
| 3 | 70–76 | 1–2.5 | 1 |
| 4 | 58 | 2.5 | ≧10 |
| 5 | 39–42 | 2 | NA |
| 10 | 72–87 | 5 | >1 |
| 11 | 95–98 | 0.3–3 | 0.01–0.1 |
| 12 | 64–80 | <0.3 | 5–10 |
| 16 | 85–88 | 1.3 | 0.003 |
| 16A | NA | <0.2 | 0.001 |
| 17 | 96 | ≦0.3 | ≦0.01 |
| 19 | 65–71 | 3 | 0.1–1 |
| 20 | 64 | 10 | 1 |
| 21 | 44–74 | 1 | 0.01–1 |
| 22 | 76–82 | <0.3–5 | 0.01 |
| 23 | 92–95 | <0.3 | 0.003–0.01 |
| 24 | 65–70 | 16 | 0.01–0.1 |
| 25 | 96 | ≦0.3–0.4 | 0.003 |
| 26 | 97 | ≦0.3–0.5 | 0.003 |
| 27 | 37–57 | >0.001 | 10 |
| 28 | 70 | >26 | 0.1–1 |
| 29 | 75–83 | 2.8 | 0.1–1 |
| 31 | 65–71 | 3 | 0.1–1 |
| 32 | 96 | <0.3 | 0.003–0.01 |
| 34 | 41 | NA | <10 |
| 35 | 57–70 | NA | NA |
| 36 | 69–84 | NA | 0.01 |
| 37 | 82–95 | 0.3 | 0.1 |
| 38 | 96–98 | NA | <0.001 |
| 42 | 63 | 2 | 10 |
| 44 | 89 | 0.1 | 0.001–0.01 |
| 45 | 83–91 | 0.5 | 0.01–0.1 |
| 46 | 89 | 1 | 0.001–0.01 |
| 47 | 91 | NA | 0.001–0.01 |
| 48 | 63–92 | NA | 0.01–0.1 |
| 49 | 84–94 | NA | ≦0.1 |
| 50 | 84–97 | NA | 0.1 |
| 51 | 55 | NA | NA |
| 52 | 89–94 | NA | 0.1–1 |
| 53 | 82–94 | NA | 0.001–0.01 |
| 54 | 70–80 | NA | 0.1 |
| 55 | 66–79 | NA | 0.1–1 |
| 56 | 79–93 | NA | 0.1–1 |

TABLE 1-continued

CHART G
The utility of this invention is demonstrated by the ability of the compounds used to inhibit viral reverse transcriptase, an enzyme essential for human immunodeficiency virus replication. This enzyme has characteristics which differentiate it from other known cellular polymerases and it is a unique enzyme which is not found in uninfected cells.

| EX-AMPLE | RT %[1] INHIBITION (100 μM) | INHIBITION[2] OF SYNCYTIA FORMATION $ED_{50}$ (μM) | PBL[3] INHIBITION OF VIRAL REPLICATION (p24 & RNA) $ED_{50}$ (μM) |
|---|---|---|---|
| 57 | 52–65 | NA | NA |
| 58 | 94–98 | NA | <0.1 |
| 59 | 61–75 | NA | NA |
| 60 | 89–92 | NA | 0.1–1 |
| 61 | 91 | NA | 1 |
| 62 | 64–78 | NA | 1–10 |
| 63 | 82–88 | NA | 1 |
| 64 | 88–94 | NA | ≦1 |
| 65 | 81–93 | NA | ≦0.001 |
| 66 | 68–79 | >280 | 1–10 |
| 67 | 60–84 | NA | NA |
| 68 | 78–95 | NA | NA |
| 69 | 95 | NA | 0.1 |
| 70 | 83–91 | 2 | ≧1 |
| 71 | 88–95 | NA | 0.01–0.1 |
| 72 | 43–66 | NA | <0.01 |
| 73 | 94–95 | NA | <0.001 |
| 74 | 82–84 | NA | 0.01–0.1 |
| 75 | 77 | NA | 0.01–0.1 |
| 76 | 65–76 | NA | 0.1–1 |
| 78 | 74 | NA | NA |
| 80 | 61–70 | NA | NA |
| 81 | 90–98 | 0.9 | <0.001 |
| 82 | 87–93 | 10 | 0.01–0.1 |
| 83 | 97–98 | <0.3 | <0.001 |
| 84 | 97 | NA | <0.001 |
| 85 | 93–96 | <0.2 | 0.001–0.01 |
| 86 | 78–96 | <0.2 | 0.001–0.01 |
| 87 | 96–98 | NA | 0.01 |
| 88 | 56–88 | NA | 0.1 |
| 89 | 61–74 | NA | 0.1 |
| 90 | 96 | NA | <0.001 |
| 91 | 85–91 | NA | 0.1 |
| 92 | 94 | NA | 0.1–1 |
| 93 | 87 | NA | NA |
| 94 | 85 | NA | 0.01–0.1 |
| 95 | 81–93 | NA | <0.001 |
| 97 | 52–80 | NA | ≦0.01 |
| 99 | 93–95 | NA | 0.001–0.01 |
| 100 | 81–82 | NA | NA |
| 101 | 93–96 | NA | 0.01 |
| 102 | 48 | NA | 10 |
| 103 | 72 | NA | <0.01 |
| 104 | 92–96 | NA | 0.01 |
| 105 | 82–96 | NA | ≦0.001 |
| 106 | 76–81 | NA | ≦0.001 |
| 107 | 77–87 | NA | NA |
| 108 | 77–89 | NA | NA |
| 109 | 56–82 | NA | NA |
| 111 | 86–92 | NA | NA |
| 112 | 74–82 | NA | NA |
| 113 | 92–96 | NA | NA |
| 116 | 45–52 | NA | <10 |
| 117 | 92 | NA | NA |
| 119 | 53–58 | NA | NA |
| 120 | 87–90 | NA | NA |
| 121 | 64–70 | NA | NA |
| 122 | 84 | NA | NA |
| 123 | 47–60 | NA | NA |
| 124 | 95 | NA | >0.1 |
| 128 | 89–98 | NA | NA |
| 129 | 68–84 | NA | NA |
| 130 | 48–59 | NA | NA |
| 131 | 85–97 | NA | NA |
| 132 | 95–98 | NA | 0.001–0.01 |
| 133 | 76–84 | 1 | 0.01 |

NA = not available.

[1] Viral reverse transcriptase is found in extracts from bacterial clones prepared according to the procedure described by Larder, B., Purifoy D., Powell, K. and Darby, G., AIDS virus reverse transcriptase defined by high level expression in *Escherichia coli.*, EMBO J. 6, 3133–3137 (1987). Inhibition of this enzyme is determined in a cell free assay which measures the level of radioactive precursors incorporated into DNA. Extracts prepared according to the procedure of Kleid, D. G., et al., Science, 1125–1129 (1981) are incubated in a mixture of inhibitor, 20 mM dithiothreitol, 60 mM sodium chloride, 0.05% NP-40, 10 mM magnesium chloride, 50 mM Tris pH 8.3, 10 μM [$^{35}$S]-labeled deoxynucleoside-5'-triphosphate, 10 μg/ml RNA template (poly rC or poly rG) and 5 μg/ml DNA primer (oligo dG or oligo dT) for 15 minutes at 37°. Incorporation of radio labeled precursor is determined by harvesting the trichloroacetic acid precipitated reaction mixtures on glass fiber filters, drying, and determining counts. The results of various assays are combined and reported as % inhibition at a 100 μM dose in Table I.

[2] The utility of this invention is further demonstrated by the ability of various compounds used to inhibit HIV-induced syncytia formation in a tissue culture assay using MT-2 cells infected with HIV-1. This test is described by Nara et al., Quantitative infectivity assay for HIV-1 and -2, Nature 332, 469–470 (1988), as well as in AIDS RESEARCH AND HUMAN RETROVIRUSES, vol. 4, No. 6, pages 449–455 (1988), Mary Ann Liebent, Inc., Publishers, and in an article by Mariano Busso, et al., entitled "Nucleotide Dimers Suppress HIV Expression In Vitro". The results ($ED_{50}$ means the concentration, in μM of drug, required to inhibit syncytia formation to the extent of 50%) of various assay are combined and reported in Table I. In comparison, the known commercial compound, AZT, exhibited similar anti-HIV potency in this assay with 100 percent and 50 percent reductions in syncytia formation at concentrations of approximately 1 μM and 0.5 μM, respectively.

[3] The utility of the compounds of the invention is further demonstrated by the activity of this compound in the inhibition of HIV infection in primary peripheral blood lymphocytes (primary PBL assay). The primary PBL assay offers the following advantages:
(a) The assays are performed with primary human lymphocytes. Thereby, undesired testing of transformed cell lines is avoided in which host cell and virus may have undergone processes of mutual adaptation. Performance of cell culture in serum containing media closely mimics the in vivo situation.
(b) The primary PBL assay distinguishes between true antiviral effect which is due to the drug and cytostatic/cytotoxic reactions. (c) Viral replication is precisely followed by kinetic measurement of viral nucleic acids and proteins. (d) Nucleic acids (total HIV-RNA intra- and extracellular) and protein (secreted p24) are measured in parallel which permits one to differentiate between the compound's effect on virus replication and on the expression of viral proteins. This leads to additional information regarding the efficacy of the test compound. (e) Tolerance of the cell culture against low amounts of organic solvents also permits the investigation of hydrophobic substances. (f) The dose of the drug causing half maximal suppression of virus replication is determined. (g) The screening system is standardized and automated to a high degree.

The primary PBL assay uses the following procedure:

Effects of the compounds of the invention on cell proliferation are determined by lymphocyte proliferation assays. Starting with a 100 micromolar solution, the compound is serially diluted 10 fold. One tenth of the concentration of a compound causing half maximal inhibition of cellular proliferation is employed for all subsequent testing.

Peripheral human lymphocytes are isolated by density gradient centrifugation. After stimulation by mitogen the cells are infected with a standardized preparation of HIV.

Subsequently, the infected cells are cultured in the presence of the drug for four days. Individual cultures are established to measure viral replication three and four days following infection. Untreated cells and AZT-treated cells are included as controls in parallel with the drugs under investigation.

The amount of viral core protein p24 synthesized and release by the infected cells is determined in the supernatant by the capture-ELISA technique on days three and four. By comparing with a standard preparation, the amount of protein produced by the virus infected cells is quantified.

The total amount of viral RNA synthesized by the infected lymphocytes is determined by a special nucleic acid hybridization on days three and four of culture. By including a standard preparation of HIV-RNA the amount of synthesized RNA is quantified.

If a drug shows antiviral effects in the primary assay, all steps of the primary assay are repeated. In addition, viability of HIV-infected cells is determined in parallel with assays for viral p24 and RNA. In order to evaluate the half maximal antiviral effect of the drug, a concentration dependency of the drug action is measured.

Numerous examples of the compounds of the invention are assayed according to this procedure. The anti-HIV activity, as measured by the inhibition of the release of core p24 protein in HIV infected human lymphocytes, is used to calculate $ED_{50}$-antiviral (the concentration required to give a 50% reduction in p24 synthesis). The results are shown in Table I.

We claim:

1. A diaromatic substituted compound of formula (III)

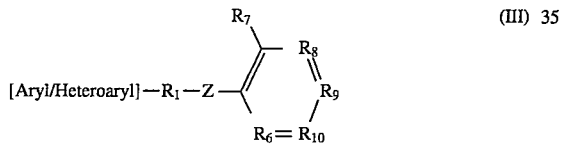
(III)

where $R_1$ is —$CH_2$— or —CO—;
where Z is

(Z-III)

where $n_{12}$ is 1 and $n_{13}$ is 1,

(Z-V)

where $Y_3$ is —$N(Y_{3-1})$— where $Y_{3-1}$ is $C_1$–$C_4$ alkyl and $n_{12}$ and $n_{13}$ are as defined above;

where $R_6$ is —N=;
where $R_7$ is —$N(R_{7-5})(R_{7-6})$ where $R_{7-5}$ is
  $C_1$–$C_6$ alkyl,
  —$CH_2$—cyclopropyl,
  —$CH_2$—$CH_2F$, and where $R_{7-6}$ is —H;
where $R_8$ is —$CR_{8-1}$= where $R_{8-1}$ is —H or —F;
where $R_9$ is —$CR_{9-1}$= where $R_{9-1}$ is —H or —F;
where $R_{10}$ is —$CR_{10-1}$= where $R_{10-1}$ is —H or —F;
where Aryl/Heteroaryl is a substituent selected from the group of substituents of formula (7)

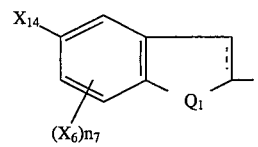
(7)

where ⁓ is a double bond;
where $Q_1$ is —$NX_{11}$— where $X_{11}$ is —H;
where $X_{14}$ is —H,
  —O—$CH_2$—ϕ,
  —O—$CH_2$—$COOR_{14-10}$ where $R_{14-10}$ is
    —H,
    $C_1$–$C_4$ alkyl,
  —$CH_2$—ϕ,
  $C_1$–$C_6$ alkyl,
  —F, —Cl, Br,
  —O—$SO_2$—$X_{14-11}$ where $X_{14-11}$ is $C_1$–$C_4$ alkyl,
  —$NO_2$, —$NH_2$, —$N_3$,
  —NH—$SO_2$—$X_{14-1}$ where $X_{14-1}$ is $C_1$–$C_6$ alkyl,
  —N=$C(X_{14-4})$—$N(X_{14-7})(X_{14-8})$ where
    (a) $X_{14-4}$ is —H or $C_1$–$C_4$ alkyl and where $X_{14-7}$ and $X_{14-8}$ are the same or different and are $C_1$–$C_6$ alkyl,
  —$N(X_{14-2})$—CO—$X_{14-9}$ where $X_{14-2}$ is —H or $C_1$–$C_4$ alkyl and where $X_{14-9}$ is
    —H,
    $C_1$–$C_4$ alkyl or
    —ϕ where $X_{14-2}$ is defined above;
where $n_7$ is 0 or 1;
where $X_6$ is —H,
  —OH,
  —O—$CH_2$—ϕ,
  —CHO,
  $C_1$–$C_3$ alkoxy,
  —O—$SO_2$—$X_{6-12}$ where $X_{6-12}$ is $C_1$–$C_4$ alkyl,
  —C≡N,
  —O—$(CH_2)_{n3}$—$N(X_{6-3})(X_{6-4})$ where $n_3$ is 2 thru 5, where $X_{6-3}$ is —H or where $X_{6-3}$ and $X_{6-4}$ are taken together with the attached nitrogen atom to form a heterocyclic ring selected from the group consisting of 1-pyrrolidinyl, 1-piperidinyl, 1-piperazinyl, N-morpholinyl or 1-aziridinyl,
  —$(CH_2)_{n24}$—OH, where $n_{24}$ is 1,
  —NH—$SO_2$—$X_{6-7}$ where $X_{6-7}$ is $C_1$–$C_4$ alkyl, enantiomers, pharmaceutically acceptable salts, hydrates and solvates thereof.

2. A diaromatic substituted compound (III) according to claim 1 where $R_1$ is —CO—.

3. A diaromatic substituted compound (III) according to claim 1 where Z is

(Z-III)

4. A diaromatic substituted compound (III) according to claim 1 where $R_7$ is —$N(R_{7-5})(R_{7-6})$ where $R_{7-5}$ is $C_1$–$C_4$ alkyl.

5. A diaromatic substituted compound (III) according to claim 4 where $C_1$–$C_4$ alkyl is —$CH_2$—$CH_3$, —$CH(CH_3)_2$ or —$C(CH_3)_3$.

6. A diaromatic substituted compound (III) according to claim 1 which is
1-[indolyl-2-carbonyl]-4-[3-(ethylamino)-2-pyridinyl]piperazine,
1-[indolyl-2-carbonyl]-4-[3-(1-methylethylamino)-2-pyridinyl]piperazine, 1-[indolyl-2-carbonyl]-4-[3-(N,N-diethylamino)-2-pyridinyl]piperazine,
1-[indolyl-2-methyl]-4-[3-(ethylamino)-2-pyridinyl]piperazine,
1-[5-fluoroindolyl-2-carbonyl]-4-[3-(propylamino)-2-pyridinyl]piperazine,
1-[5-chloroindoyl-2-carbonyl]-4-[3-(ethylamino)-2-pyridinyl]piprazine,
1-[5-fluoroindolyl-2-carbonyl]-4-[3-(ethylamino)-2-pyridinyl]piperazine,
1-[5-ethylindolyl-2-carbonyl]-4-[3-(ethylamino)-2-pyridinyl]piperazine,
1-[5-fluoroindolyl-2-carbonyl]-4-[3-(1-methylethylamino)-2-pyridinyl]-piperazine,
1-[indolyl-2-carbonyl]-4-[3-(cyclopropylmethylamino)-2-pyridinyl]piperazine,
1-[5-fluoroindolyl-2-methyl]-4-[3-(1-methylethylamino)-2-pyridinyl]piperazine,
1-[5-benzyloxyindolyl-2-carbonyl]-4-(3-ethylamino-2-pyridinyl)piperazine,
1-[5-benzyloxyindolyl-2-carbonyl]-4-[3-(1-methylethyl)amino-2-pyridinyl]-piperazine,
1-[indolyl-2-methyl]-4-[3-(1-methylethylamino)-2-pyridinyl]piperazine,
1-[indolyl-2-carbonyl]-4-[3-(1,1-dimethylethylamino)-2-pyridinyl]piperazine,
1-[5-fluoroindolyl-2-carbonyl]-4-[3-(1,1-dimethylethylamino)-2-pyridinyl]piperazine,
1-[5-(ethoxycarbonylmethoxy)indolyl-2-carbonyl]-4-[3-(1-methylethylamino)-2-pyridinyl]piperazine,
1-(5-fluoroindolyl-2-carbonyl)-4-[3-methylamino-2-pyridinyl]piperazine,
1-(indolyl-2-carbonyl)-4-[3-(methylamino)-2-pyridinyl]piperazine,
1-[5-(benzyloxycarbonylmethoxy)indolyl-2-carbonyl]-4-[3-(1-methylethylamino)-2-pyridinyl]piperazine,
1-[5-(carboxymethoxy)indolyl-2-carbonyl]-4-[3-(1-methylethylamino)-2-pyridinyl]piperazine,
1-[(5N-(N',N'-dimethylaminomethylene)aminoindolyl)carbonyl]-4-(3-(1-methylethylamino)-2-pyridinyl)piperazine,
1-[6-methoxyindolyl-2-carbonyl]-4-[3-(1-methylethylamino)-2-pyridinyl]piperazine,
1-[4-methoxyindolyl-2-carbonyl]-4-[3-(1-methylethylamino)-2-pyridinyl]piperazine,
1-[5-methylindolyl-2-carbonyl]-4-[3-(1-methylethylamino)-2-pyridinyl]piperazine,
1-[5-fluoro-6-methoxyindolyl-2-carbonyl]-4-[3-(1-methylethylamino)-2-pyridinyl]piperazine,
1-[5-bromoindolyl-2-carbonyl]-4-[3-(1-methylethylamino)-2-pyridinyl]piperazine,
1-[5-bromo-6-methoxyindolyl-2-carbonyl]-4-[3-(1-methylethylamino)-2-pyridinyl]piperazine,
1-[indolyl-2-carbonyl]-4-[3-(1-methylpropyl)amino-2-pyridinyl]piperazine,
1-[indolyl-2-carbonyl]-4-[3-(1-ethylpropyl)amino-2-pyridinyl]piperazine,
1-[5-aminoindolyl-2-carbonyl]-4-[3-(1-methylethylamino)-2-pyridinyl]piperazine,
1-[5-fluoroindolyl-2-carbonyl]-4-[3-(2',2'-dimethylpropylamino)-2-pyridinyl]piperazine,
1-[5-nitroindolyl-2-carbonyl]-4-[3-(1-methylethylamino)-2-pyridinyl]piperazine,
1-[5-acetamidoindolyl-2-carbonyl]-4-[3-(1-methylethylamino)-2-pyridinyl]piperazine,
1-[5-methanesulfonamidoindolyl-2-carbonyl]-4-[3-(1-methylethylamino)-2-pyridinyl]piperazine,
1-[6-formylindoyl-2-carbonyl]-4-[3-(1-methylethylamino)-2-pyridinyl]piperazine,
1-[5-azido-2-indolycarbonyl]-4-[3-(1-methylethylamino)-2-pyridinyl]piperazine,
1-[indolyl-2-carbonyl]-4-[3-(2-fluoroethylamino)-2-pyridinyl]piperazine,
1-[6-hydroxymethylindolyl-2-carbonyl]-4-[3-(1-methylethylamino)-2-pyridinyl]piperazine,
1-[6-hydroxymethylindolyl-2-carbonyl]-4-[3-(ethylamino)-2-pyridinyl]piperazine,
1-(indolyl-2-carbonyl)-4-(N-methyl-N-(3-(1-methylethylamino)-2-pyridinyl)amino)piperidine,
1-(6-cyanoindolyl-2-carbonyl)-4-[3-(ethylamino)-2-pyridinyl]piperazine,
1-(6-cyanoindolyl-2-carbonyl)-4-[3-(1-methylethylamino)-2-pyridinyl]piperazine,
1-[5-nitroindolyl-2-carbonyl]-4-[3-(1,1-dimethylethylamino)-2-pyridinyl]piperazine,
1-[(5-(N',N'-dimethylaminomethylene)aminoindolyl-2-carbonyl]-4-[3-(1,1-dimethylethylamino)-2-pyridinyl]piperazine.

7. A diaromatic substituted compound (III) according to claim 6 which is
1-[indolyl-2-carbonyl]-4-[3-(ethylamino)-2-pyridinyl]piperazine,
1-[indolyl-2-carbonyl]-4-[3-(1-methylethylamino)-2-pyridinyl]piperazine,
1-[5-fluoroindolyl-2-carbonyl]-4-[3-(ethylamino)-2-pyridinyl]piperazine,
1-[5-fluoroindolyl-2-carbonyl]-4-[3-(1-methylethylamino)-2-pyridinyl]piperazine,
1-[5-fluoroindolyl-2-methyl]-4-[3-(1-methylethylamino)-2-pyridinyl]piperazine,
1-[indolyl-2-carbonyl]-4-[3-(1,1-dimethylethylamino)-2-pyridinyl]piperazine,
1-[5-fluoroindolyl-2-carbonyl]-4-[3-(1,1-dimethylethylamino)-2-pyridinyl]piperazine,
1-[5-(carboxymethoxy)indolyl-2-carbonyl]-4-[3-(1-methylethyl- amino)-2-pyridinyl]piperazine,
1-[(5N-(N',N'-dimethylaminomethylene)aminoindolyl)carbonyl]-4-(3-(1-methylethylamino)-2-pyridinyl)piperazine,
1-[indolyl-2-carbonyl]-4-[3-(1-ethylpropyl)amino-2-pyridinyl]piperazine and
1-[5-methanesulfonamidoindolyl-2-carbonyl]-4-[3-(1-methylethylamino)-2-pyridinyl]piperazine.

8. A diaromatic substituted compound (III) according to claim 6 which is 1-[5-methanesulfonamidoindolyl-2-carbonyl]-4-[3-(1-methylethylamino)-2-pyridinyl]piperazine.

9. A diaromatic substituted compounds (III) according to claim 1 where the pharmaceutically acceptable salt is an acid addition salt.

10. A diaromatic substituted compounds (III) according to claim 9 where the acid addition salt is selected from the group consisting of methanesulfonic, hydrochloric, hydrobromic, sulfuric, phosphoric, nitric, benzoic, citric, tartaric, fumaric, maleic, p-toluenesulfonic, benzenesulfonic, $CH_3$—$(CH_2)_n$—COOH where n is 0 thru 4 and HOOC—$(CH_2)_n$—COOH where n is as defined above.

11. A diaromatic substituted compound (III) according to claim 8 which is 1-[5-methanesulfonamidoindolyl-2-carbonyl]-4-[3-(1-methylethylamino)-2-pyridinyl]piperazine monomethanesulfonate salt.

* * * * *